(12) United States Patent
Feingold et al.

(10) Patent No.: US 11,938,192 B2
(45) Date of Patent: Mar. 26, 2024

(54) DOSAGE REGIMES FOR THE ADMINISTRATION OF AN ANTI-CD19 ADC

(71) Applicants: ADC THERAPEUTICS SA, Epalinges (CH); MEDIMMUNE LIMITED, Cambridge (GB)

(72) Inventors: Jay Marshall Feingold, Murray Hill, NJ (US); David Rodney Ungar, Murray Hill, NJ (US)

(73) Assignees: MEDIMMUNE LIMITED, Cambridge (GB); ADC THERAPEUTICS SA, Epalinges (CH)

( * ) Notice: Subject to any disclaimer, the term of this patent is extended or adjusted under 35 U.S.C. 154(b) by 0 days.

(21) Appl. No.: 17/699,065

(22) Filed: Mar. 18, 2022

(65) Prior Publication Data

US 2022/0280651 A1 Sep. 8, 2022

Related U.S. Application Data

(63) Continuation of application No. 16/622,649, filed as application No. PCT/EP2018/065873 on Jun. 14, 2018, now Pat. No. 11,318,211.

(30) Foreign Application Priority Data

| Jun. 14, 2017 | (GB) | 1709440 |
| Jun. 14, 2017 | (GB) | 1709444 |
| Jun. 30, 2017 | (GB) | 1710494 |
| Jun. 30, 2017 | (GB) | 1710495 |
| Dec. 8, 2017 | (GB) | 1720542 |
| Dec. 8, 2017 | (GB) | 1720543 |
| Feb. 20, 2018 | (GB) | 1802679 |
| May 23, 2018 | (GB) | 1808473 |

(51) Int. Cl.

| A61K 47/68 | (2017.01) |
| A61K 31/5517 | (2006.01) |
| A61P 35/02 | (2006.01) |
| C07K 16/28 | (2006.01) |
| A61K 9/00 | (2006.01) |
| A61K 31/519 | (2006.01) |
| A61K 31/573 | (2006.01) |
| A61K 31/7068 | (2006.01) |
| A61K 39/00 | (2006.01) |

(52) U.S. Cl.
CPC ...... A61K 47/6803 (2017.08); A61K 31/5517 (2013.01); A61K 47/6849 (2017.08); A61K 47/6867 (2017.08); A61P 35/02 (2018.01); C07K 16/2827 (2013.01); A61K 9/0019 (2013.01); A61K 9/0053 (2013.01); A61K 31/519 (2013.01); A61K 31/573 (2013.01); A61K 31/7068 (2013.01); A61K 2039/505 (2013.01); A61K 2039/542 (2013.01); A61K 2039/545 (2013.01); C07K 16/2887 (2013.01)

(58) Field of Classification Search
CPC ............ A61K 47/6803; A61K 31/5517; A61K 47/6849; A61K 47/6867; A61K 9/0019; A61K 9/0053; A61K 31/519; A61K 31/573; A61K 31/7068; A61K 2039/505; A61K 2039/542; A61K 2039/545; A61K 45/06; A61K 2300/00; A61P 35/02; A61P 39/00; A61P 35/00; C07K 16/2827; C07K 16/2887; C07K 2317/24; C07K 16/2803
See application file for complete search history.

(56) References Cited

U.S. PATENT DOCUMENTS

| 3,361,742 A | 1/1968 | Julius et al. |
| 3,523,941 A | 8/1970 | Leimgruber et al. |
| 3,524,849 A | 8/1970 | Batcho et al. |
| 3,794,644 A | 2/1974 | Karlyone et al. |
| 4,185,016 A | 1/1980 | Takanabe et al. |
| 4,239,683 A | 12/1980 | Takanabe et al. |
| 4,309,437 A | 1/1982 | Ueda et al. |
| 4,353,827 A | 10/1982 | Hunkeler et al. |
| 4,382,032 A | 5/1983 | Hunkeler et al. |
| 4,386,028 A | 5/1983 | Hunkeler et al. |
| 4,405,516 A | 9/1983 | Hunkeler et al. |
| 4,405,517 A | 9/1983 | Hunkeler et al. |
| 4,407,752 A | 10/1983 | Hunkeler et al. |
| 4,427,587 A | 1/1984 | Kaneko et al. |
| 4,427,588 A | 1/1984 | Kaneko et al. |
| 4,701,325 A | 10/1987 | Ueda et al. |

(Continued)

FOREIGN PATENT DOCUMENTS

| EP | 0522868 | 1/1993 |
| EP | 0875569 | 11/1998 |

(Continued)

OTHER PUBLICATIONS

Brad S. Kahl. et al., A phase 1 dose-escalation study to evaluate the tolerability, safety, pharmacokinetics, and antitumor activity of ADCT-402 in patients with relapsed or refractory B-cell lineage non-Hodgkin lymphoma (B-NHL), Jun. 3-7, 2016, ASCO Annual Meeting (Year: 2016).*

(Continued)

*Primary Examiner* — Hong Sang

(74) *Attorney, Agent, or Firm* — Casimir Jones SC; Lisa Mueller

(57) ABSTRACT

The present disclosure relates to the treatment of pathological conditions, such as cancer, with Antibody Drug Conjugates (ADCs). In particular, the present disclosure relates to administration of ADCs which bind to CD19 (CD19-ADCs).

19 Claims, 5 Drawing Sheets

Specification includes a Sequence Listing.

(56) References Cited

U.S. PATENT DOCUMENTS

| | | |
|---|---|---|
| 4,816,567 A | 3/1989 | Cabilly et al. |
| 4,923,984 A | 5/1990 | Matsumura et al. |
| 5,362,852 A | 11/1994 | Geoghegan |
| 5,418,241 A | 5/1995 | Jegham et al. |
| 5,440,021 A | 8/1995 | Chuntharapai et al. |
| 5,583,024 A | 12/1996 | McElroy et al. |
| 5,621,002 A | 4/1997 | Bosslet et al. |
| 5,644,033 A | 7/1997 | Seon |
| 5,674,713 A | 10/1997 | McElroy et al. |
| 5,700,670 A | 12/1997 | Yamagishi et al. |
| 5,773,223 A | 6/1998 | Shyamala et al. |
| 5,792,616 A | 8/1998 | Persico et al. |
| 5,854,399 A | 12/1998 | Salomon et al. |
| 5,869,445 A | 2/1999 | Cheever et al. |
| 5,976,551 A | 11/1999 | Mottez et al. |
| 6,011,146 A | 1/2000 | Mottez et al. |
| 6,153,408 A | 11/2000 | Abastado et al. |
| 6,165,476 A | 12/2000 | Strom et al. |
| 6,214,345 B1 | 4/2001 | Firestone et al. |
| 6,218,519 B1 | 4/2001 | Kenten et al. |
| 6,268,488 B1 | 7/2001 | Barbas, III et al. |
| 6,362,331 B1 | 3/2002 | Kamal et al. |
| 6,518,404 B1 | 2/2003 | Li et al. |
| 6,534,482 B1 | 3/2003 | Fikes et al. |
| 6,555,339 B1 | 4/2003 | Liaw et al. |
| 6,562,806 B1 | 5/2003 | Thurston et al. |
| 6,602,677 B1 | 8/2003 | Wood et al. |
| 6,608,192 B1 | 8/2003 | Thurston et al. |
| 6,660,742 B2 | 12/2003 | Lee |
| 6,660,856 B2 | 12/2003 | Wang |
| 6,677,435 B2 | 1/2004 | Barbas, III et al. |
| 6,747,144 B1 | 6/2004 | Thurston et al. |
| 6,759,509 B1 | 7/2004 | King et al. |
| 6,835,807 B1 | 12/2004 | Sasaki et al. |
| 6,884,799 B2 | 4/2005 | Kamal et al. |
| 6,909,006 B1 | 6/2005 | Thurston et al. |
| 7,049,311 B1 | 5/2006 | Thurston et al. |
| 7,067,511 B2 | 6/2006 | Thurston et al. |
| 7,223,837 B2 | 5/2007 | De Groot et al. |
| 7,244,724 B2 | 7/2007 | Liu et al. |
| 7,265,105 B2 | 9/2007 | Thurston et al. |
| 7,375,078 B2 | 5/2008 | Feng |
| 7,407,951 B2 | 8/2008 | Thurston et al. |
| 7,429,658 B2 | 9/2008 | Howard et al. |
| 7,498,298 B2 | 3/2009 | Doronina et al. |
| 7,511,032 B2 | 3/2009 | Liu et al. |
| 7,521,541 B2 | 4/2009 | Eigenbrot et al. |
| 7,528,126 B2 | 5/2009 | Howard et al. |
| 7,557,099 B2 | 7/2009 | Howard et al. |
| 7,612,062 B2 | 11/2009 | Gregson et al. |
| 7,704,924 B2 | 4/2010 | Thurston et al. |
| 7,723,485 B2 | 5/2010 | Junutula et al. |
| 7,741,319 B2 | 6/2010 | Howard et al. |
| 8,034,808 B2 | 11/2011 | Delavault et al. |
| 8,163,736 B2 | 4/2012 | Gauzy et al. |
| 8,487,092 B2 | 7/2013 | Howard et al. |
| 8,501,934 B2 | 8/2013 | Howard et al. |
| 8,592,576 B2 | 11/2013 | Howard et al. |
| 8,609,089 B2 | 12/2013 | Langermann et al. |
| 8,633,185 B2 | 1/2014 | Howard et al. |
| 8,637,664 B2 | 1/2014 | Howard et al. |
| 8,697,688 B2 | 4/2014 | Howard et al. |
| 8,735,553 B1 | 5/2014 | Li et al. |
| 8,829,184 B2 | 9/2014 | Howard et al. |
| 8,940,733 B2 | 1/2015 | Howard et al. |
| 9,321,774 B2 | 4/2016 | Howard et al. |
| 9,376,440 B2 | 6/2016 | Howard et al. |
| 9,399,641 B2 | 7/2016 | Howard et al. |
| 9,624,227 B2 | 4/2017 | Howard et al. |
| 9,834,606 B2 | 12/2017 | Li et al. |
| 9,931,414 B2 * | 4/2018 | Van Berkel ............ A61P 35/00 |
| 2001/0055751 A1 | 12/2001 | Reiter et al. |
| 2002/0034749 A1 | 3/2002 | Billing-Medel et al. |
| 2002/0042366 A1 | 4/2002 | Thompson et al. |
| 2002/0150573 A1 | 10/2002 | Nussenzweig |
| 2002/0193567 A1 | 12/2002 | Jacobs et al. |
| 2003/0060612 A1 | 3/2003 | Goddard et al. |
| 2003/0062401 A1 | 4/2003 | Hasz et al. |
| 2003/0064397 A1 | 4/2003 | Spancake et al. |
| 2003/0065143 A1 | 4/2003 | Eaton et al. |
| 2003/0091580 A1 | 5/2003 | Mitcham et al. |
| 2003/0096743 A1 | 5/2003 | Senter et al. |
| 2003/0096961 A1 | 5/2003 | Baker et al. |
| 2003/0105292 A1 | 6/2003 | Liaw et al. |
| 2003/0109676 A1 | 6/2003 | Li et al. |
| 2003/0118592 A1 | 6/2003 | Ledbetter et al. |
| 2003/0119121 A1 | 6/2003 | Baker et al. |
| 2003/0119122 A1 | 6/2003 | Baker et al. |
| 2003/0119125 A1 | 6/2003 | Baker et al. |
| 2003/0119126 A1 | 6/2003 | Baker et al. |
| 2003/0119128 A1 | 6/2003 | Baker et al. |
| 2003/0119129 A1 | 6/2003 | Baker et al. |
| 2003/0119130 A1 | 6/2003 | Baker et al. |
| 2003/0119131 A1 | 6/2003 | Baker et al. |
| 2003/0124140 A1 | 7/2003 | Bangur et al. |
| 2003/0124579 A1 | 7/2003 | Mack et al. |
| 2003/0129192 A1 | 7/2003 | Chenault et al. |
| 2003/0130189 A1 | 7/2003 | Senter et al. |
| 2003/0134790 A1 | 7/2003 | Langenfeld |
| 2003/0143557 A1 | 7/2003 | Penner |
| 2003/0157089 A1 | 8/2003 | Xu et al. |
| 2003/0165504 A1 | 9/2003 | Retter et al. |
| 2003/0185830 A1 | 10/2003 | Xu et al. |
| 2003/0186372 A1 | 10/2003 | Baker et al. |
| 2003/0186373 A1 | 10/2003 | Baker et al. |
| 2003/0194704 A1 | 10/2003 | Penn et al. |
| 2003/0195196 A1 | 10/2003 | Thurston et al. |
| 2003/0206918 A1 | 11/2003 | Fanger et al. |
| 2003/0219806 A1 | 11/2003 | Glucksmann et al. |
| 2003/0224411 A1 | 12/2003 | Stanton et al. |
| 2003/0224454 A1 | 12/2003 | Ryseck et al. |
| 2003/0228319 A1 | 12/2003 | Frantz et al. |
| 2003/0232056 A1 | 12/2003 | Fanger et al. |
| 2003/0232350 A1 | 12/2003 | Afar et al. |
| 2004/0001827 A1 | 1/2004 | Dennis |
| 2004/0005320 A1 | 1/2004 | Thompson et al. |
| 2004/0005538 A1 | 1/2004 | Chen et al. |
| 2004/0005563 A1 | 1/2004 | Mack et al. |
| 2004/0005598 A1 | 1/2004 | Devaux et al. |
| 2004/0018194 A1 | 1/2004 | Francisco et al. |
| 2004/0018553 A1 | 1/2004 | Billing-Medel et al. |
| 2004/0022727 A1 | 2/2004 | Stanton et al. |
| 2004/0044179 A1 | 3/2004 | Baker et al. |
| 2004/0044180 A1 | 3/2004 | Baker et al. |
| 2004/0052793 A1 | 3/2004 | Carter et al. |
| 2004/0101874 A1 | 5/2004 | Ghosh et al. |
| 2004/0101899 A1 | 5/2004 | Dillon et al. |
| 2004/0121940 A1 | 6/2004 | De Groot et al. |
| 2004/0138269 A1 | 7/2004 | Sun et al. |
| 2004/0197325 A1 | 10/2004 | Law et al. |
| 2004/0198722 A1 | 10/2004 | Thurston et al. |
| 2004/0249130 A1 | 12/2004 | Stanton et al. |
| 2005/0271615 A1 | 12/2005 | Shabat et al. |
| 2006/0116422 A1 | 6/2006 | De Groot et al. |
| 2007/0072846 A1 | 3/2007 | Vishnuvajjala et al. |
| 2007/0185336 A1 | 8/2007 | Rossen et al. |
| 2007/0191349 A1 | 8/2007 | Howard et al. |
| 2007/0232592 A1 | 10/2007 | Delavault et al. |
| 2007/0249591 A1 | 10/2007 | Howard et al. |
| 2008/0090812 A1 | 4/2008 | Pepper et al. |
| 2008/0092940 A1 | 4/2008 | Nakajima |
| 2008/0112961 A1 | 5/2008 | Stavenhagen et al. |
| 2008/0206239 A1 | 8/2008 | Jones et al. |
| 2008/0213289 A1 | 9/2008 | Francisco et al. |
| 2008/0214525 A1 | 9/2008 | Howard et al. |
| 2009/0036431 A1 | 2/2009 | Gauzy et al. |
| 2009/0148942 A1 | 6/2009 | McDonagh et al. |
| 2009/0149449 A1 | 6/2009 | Liu et al. |
| 2009/0304710 A1 | 12/2009 | Park et al. |
| 2010/0047257 A1 | 2/2010 | Blanc et al. |
| 2010/0113425 A1 | 5/2010 | Howard et al. |
| 2010/0203007 A1 | 8/2010 | Li et al. |
| 2011/0070227 A1 | 3/2011 | Novotney-Barry et al. |
| 2011/0160192 A1 | 6/2011 | Howard et al. |

(56) References Cited

U.S. PATENT DOCUMENTS

| | | |
|---|---|---|
| 2011/0196148 A1 | 8/2011 | Howard et al. |
| 2011/0201803 A1 | 8/2011 | Howard et al. |
| 2011/0256157 A1 | 10/2011 | Howard et al. |
| 2013/0028917 A1 | 1/2013 | Howard et al. |
| 2013/0028919 A1 | 1/2013 | Howard et al. |
| 2013/0266595 A1 | 10/2013 | Flygare et al. |
| 2014/0066435 A1 | 3/2014 | Howard et al. |
| 2014/0120118 A1 | 5/2014 | Howard |
| 2014/0127239 A1 | 5/2014 | Howard |
| 2014/0234346 A1 | 8/2014 | Howard |
| 2014/0235840 A1 | 8/2014 | Khanzhin et al. |
| 2014/0274907 A1 | 9/2014 | Howard et al. |
| 2014/0275522 A1 | 9/2014 | Howard et al. |
| 2014/0294868 A1 | 10/2014 | Howard et al. |
| 2016/0074527 A1 | 7/2016 | Flygare et al. |
| 2016/0304607 A1 | 10/2016 | Sadineni et al. |

FOREIGN PATENT DOCUMENTS

| | | |
|---|---|---|
| EP | 1295944 | 3/2003 |
| EP | 1347046 | 9/2003 |
| EP | 1394274 | 3/2004 |
| EP | 1439393 | 7/2004 |
| EP | 1813614 | 8/2007 |
| EP | 2019104 | 1/2009 |
| EP | 2298817 | 3/2011 |
| EP | 2524929 | 11/2012 |
| EP | 2550975 | 1/2013 |
| EP | 2528625 | 7/2013 |
| FR | 2027356 | 12/1969 |
| FR | 2586683 | 3/1987 |
| GB | 1299198 | 12/1972 |
| GB | 2053894 | 2/1981 |
| JP | 5382792 | 7/1978 |
| JP | 57131791 | 8/1982 |
| JP | 58180487 | 10/1983 |
| JP | 05003790 | 1/1993 |
| JP | 2004113151 | 4/2004 |
| JP | 2017512801 A | 5/2017 |
| WO | WO 199102536 | 3/1991 |
| WO | WO 199207574 | 5/1992 |
| WO | WO 199217497 | 10/1992 |
| WO | WO 199219620 | 11/1992 |
| WO | WO 199318045 | 9/1993 |
| WO | WO 199410312 | 5/1994 |
| WO | WO 199428931 | 12/1994 |
| WO | WO 199504718 | 2/1995 |
| WO | WO 199630514 | 10/1996 |
| WO | WO 199707198 | 2/1997 |
| WO | WO 199744452 | 11/1997 |
| WO | WO 199813059 | 4/1998 |
| WO | WO 199837193 | 8/1998 |
| WO | WO 199840403 | 9/1998 |
| WO | WO 199851805 | 11/1998 |
| WO | WO 199851824 | 11/1998 |
| WO | WO 199928468 | 6/1999 |
| WO | WO 199946284 | 9/1999 |
| WO | WO 199958658 | 11/1999 |
| WO | WO 200003291 | 1/2000 |
| WO | WO 200012506 | 3/2000 |
| WO | WO 200012507 | 3/2000 |
| WO | WO 200012508 | 3/2000 |
| WO | WO 200012509 | 3/2000 |
| WO | WO 200014228 | 3/2000 |
| WO | WO 200020579 | 4/2000 |
| WO | WO 200022129 | 4/2000 |
| WO | WO 200032752 | 6/2000 |
| WO | WO 200036107 | 6/2000 |
| WO | WO 200040614 | 7/2000 |
| WO | WO 200044899 | 8/2000 |
| WO | WO 200012130 | 9/2000 |
| WO | WO 200053216 | 9/2000 |
| WO | WO 200055351 | 9/2000 |
| WO | WO 200075655 | 12/2000 |
| WO | WO 200100244 | 1/2001 |
| WO | WO 200116104 | 3/2001 |
| WO | WO 200116318 | 3/2001 |
| WO | WO 200138490 | 5/2001 |
| WO | WO 200140269 | 6/2001 |
| WO | WO 200140309 | 6/2001 |
| WO | WO 200141787 | 6/2001 |
| WO | WO 200145746 | 6/2001 |
| WO | WO 200146232 | 6/2001 |
| WO | WO 200146261 | 6/2001 |
| WO | WO 200148204 | 7/2001 |
| WO | WO 200153463 | 7/2001 |
| WO | WO 200157188 | 8/2001 |
| WO | WO 200162794 | 8/2001 |
| WO | WO 200166689 | 9/2001 |
| WO | WO 200172830 | 10/2001 |
| WO | WO 200172962 | 10/2001 |
| WO | WO 200175177 | 10/2001 |
| WO | WO 200177172 | 10/2001 |
| WO | WO 200188133 | 11/2001 |
| WO | WO 200190304 | 11/2001 |
| WO | WO 200194641 | 12/2001 |
| WO | WO 200198351 | 12/2001 |
| WO | WO 200202587 | 1/2002 |
| WO | WO 200202624 | 1/2002 |
| WO | WO 200202634 | 1/2002 |
| WO | WO 200206317 | 1/2002 |
| WO | WO 200206339 | 1/2002 |
| WO | WO 200210187 | 2/2002 |
| WO | WO 200210382 | 2/2002 |
| WO | WO 200212341 | 2/2002 |
| WO | WO 200213847 | 2/2002 |
| WO | WO 200214503 | 2/2002 |
| WO | WO 200216413 | 2/2002 |
| WO | WO 200222153 | 3/2002 |
| WO | WO 200222636 | 3/2002 |
| WO | WO 200222660 | 3/2002 |
| WO | WO 200222808 | 3/2002 |
| WO | WO 200224909 | 3/2002 |
| WO | WO 200226822 | 4/2002 |
| WO | WO 200230268 | 4/2002 |
| WO | WO 200238766 | 5/2002 |
| WO | WO 200254940 | 7/2002 |
| WO | WO 200259377 | 8/2002 |
| WO | WO 200260317 | 8/2002 |
| WO | WO 200261087 | 8/2002 |
| WO | WO 200264798 | 8/2002 |
| WO | WO 200271928 | 9/2002 |
| WO | WO 200272596 | 9/2002 |
| WO | WO 200278524 | 10/2002 |
| WO | WO 200281646 | 10/2002 |
| WO | WO 200283866 | 10/2002 |
| WO | WO 200286443 | 10/2002 |
| WO | WO 200288170 | 11/2002 |
| WO | WO 200288172 | 11/2002 |
| WO | WO 200289747 | 11/2002 |
| WO | WO 200292836 | 11/2002 |
| WO | WO 200294852 | 11/2002 |
| WO | WO 200298358 | 12/2002 |
| WO | WO 200299074 | 12/2002 |
| WO | WO 200299122 | 12/2002 |
| WO | WO 2002101075 | 12/2002 |
| WO | WO 2002102235 | 12/2002 |
| WO | WO 200216429 | 1/2003 |
| WO | WO 2003000842 | 1/2003 |
| WO | WO 2003002717 | 1/2003 |
| WO | WO 2003003906 | 1/2003 |
| WO | WO 2003003984 | 1/2003 |
| WO | WO 2003004529 | 1/2003 |
| WO | WO 2003004989 | 1/2003 |
| WO | WO 2003008537 | 1/2003 |
| WO | WO 2003009814 | 2/2003 |
| WO | WO 2003014294 | 2/2003 |
| WO | WO 2003016475 | 2/2003 |
| WO | WO 2003016494 | 2/2003 |
| WO | WO 2003018621 | 3/2003 |
| WO | WO 2003022995 | 3/2003 |
| WO | WO 2003023013 | 3/2003 |
| WO | WO 2003024392 | 3/2003 |
| WO | WO 2003025138 | 3/2003 |

(56) References Cited

FOREIGN PATENT DOCUMENTS

| | | |
|---|---|---|
| WO | WO 2003025148 | 3/2003 |
| WO | WO 2003025228 | 3/2003 |
| WO | WO 2003026493 | 4/2003 |
| WO | WO 2003026577 | 4/2003 |
| WO | WO 2003029262 | 4/2003 |
| WO | WO 2003029277 | 4/2003 |
| WO | WO 2003029421 | 4/2003 |
| WO | WO 2003034984 | 5/2003 |
| WO | WO 2003035846 | 5/2003 |
| WO | WO 2003042661 | 5/2003 |
| WO | WO 2003043583 | 5/2003 |
| WO | WO 2003045422 | 6/2003 |
| WO | WO 2003048202 | 6/2003 |
| WO | WO 2003054152 | 7/2003 |
| WO | WO 2003055439 | 7/2003 |
| WO | WO 2003055443 | 7/2003 |
| WO | WO 2003060612 | 7/2003 |
| WO | WO 2003062401 | 7/2003 |
| WO | WO 2003072035 | 9/2003 |
| WO | WO 2003072036 | 9/2003 |
| WO | WO 2003077836 | 9/2003 |
| WO | WO 2003081210 | 10/2003 |
| WO | WO 2003083041 | 10/2003 |
| WO | WO 2003083047 | 10/2003 |
| WO | WO 2003083074 | 10/2003 |
| WO | WO 2003087306 | 10/2003 |
| WO | WO 2003087768 | 10/2003 |
| WO | WO 2003088808 | 10/2003 |
| WO | WO 2003089624 | 10/2003 |
| WO | WO 2003089904 | 10/2003 |
| WO | WO 2003093444 | 11/2003 |
| WO | WO 2003097803 | 11/2003 |
| WO | WO 2003101283 | 12/2003 |
| WO | WO 2003101400 | 12/2003 |
| WO | WO 2003104270 | 12/2003 |
| WO | WO 2003104275 | 12/2003 |
| WO | WO 2003104399 | 12/2003 |
| WO | WO 2003105758 | 12/2003 |
| WO | WO 2004000221 | 12/2003 |
| WO | WO 2004000997 | 12/2003 |
| WO | WO 2004001004 | 12/2003 |
| WO | WO 2004005598 | 1/2004 |
| WO | WO 2004009622 | 1/2004 |
| WO | WO 2004011611 | 2/2004 |
| WO | WO 2004015426 | 2/2004 |
| WO | WO 2004016225 | 2/2004 |
| WO | WO 2004020583 | 3/2004 |
| WO | WO 2004020595 | 3/2004 |
| WO | WO 2004022709 | 3/2004 |
| WO | WO 2004022778 | 3/2004 |
| WO | WO 2004027049 | 4/2004 |
| WO | WO 2004031238 | 4/2004 |
| WO | WO 2004032828 | 4/2004 |
| WO | WO 2004032842 | 4/2004 |
| WO | WO 2004040000 | 5/2004 |
| WO | WO 2004042346 | 5/2004 |
| WO | WO 2004043361 | 5/2004 |
| WO | WO 2004043963 | 5/2004 |
| WO | WO 2004044178 | 5/2004 |
| WO | WO 2004045516 | 6/2004 |
| WO | WO 2004045520 | 6/2004 |
| WO | WO 2004045553 | 6/2004 |
| WO | WO 2004046342 | 6/2004 |
| WO | WO 2004047749 | 6/2004 |
| WO | WO 2004048938 | 6/2004 |
| WO | WO 2004053079 | 6/2004 |
| WO | WO 2004058309 | 7/2004 |
| WO | WO 2004063355 | 7/2004 |
| WO | WO 2004063362 | 7/2004 |
| WO | WO 2004063709 | 7/2004 |
| WO | WO 2004065576 | 8/2004 |
| WO | WO 2004065577 | 8/2004 |
| WO | WO 2004074320 | 9/2004 |
| WO | WO 2005023814 | 3/2005 |
| WO | WO 2005040170 | 5/2005 |
| WO | WO 2005042535 | 5/2005 |
| WO | WO 2005079479 | 9/2005 |
| WO | WO 2005082023 | 9/2005 |
| WO | WO 2005085177 | 9/2005 |
| WO | WO 2005085250 | 9/2005 |
| WO | WO 2005085251 | 9/2005 |
| WO | WO 2005085259 | 9/2005 |
| WO | WO 2005085260 | 9/2005 |
| WO | WO 2005105113 | 11/2005 |
| WO | WO 2005110423 | 11/2005 |
| WO | WO 2006065533 | 6/2006 |
| WO | WO 2006105021 | 10/2006 |
| WO | WO 2006111759 | 10/2006 |
| WO | WO 2007005874 | 1/2007 |
| WO | WO 2007039752 | 4/2007 |
| WO | WO 2007044515 | 4/2007 |
| WO | WO 2007085930 | 8/2007 |
| WO | WO 2008010101 | 1/2008 |
| WO | WO 2008047242 | 4/2008 |
| WO | WO 2008070593 | 6/2008 |
| WO | WO 2009016516 | 2/2009 |
| WO | WO 2009052249 | 4/2009 |
| WO | WO 2009117531 | 9/2009 |
| WO | WO 2010010347 | 1/2010 |
| WO | WO 2010043877 | 4/2010 |
| WO | WO 2010043880 | 4/2010 |
| WO | WO 2010091150 | 8/2010 |
| WO | WO 2010095031 | 8/2010 |
| WO | WO 2011005481 | 1/2011 |
| WO | WO 2011023883 | 3/2011 |
| WO | WO 2011028683 | 3/2011 |
| WO | WO 2011028811 | 3/2011 |
| WO | WO 2011038159 | 3/2011 |
| WO | WO 2011100227 | 8/2011 |
| WO | WO 2011130598 | 10/2011 |
| WO | WO 2011130613 | 10/2011 |
| WO | WO 2011130615 | 10/2011 |
| WO | WO 2011130616 | 10/2011 |
| WO | WO 2011161699 | 12/2011 |
| WO | WO 2012064733 | 5/2012 |
| WO | WO 2012112687 | 8/2012 |
| WO | WO 2012112708 | 8/2012 |
| WO | WO 2012128868 | 9/2012 |
| WO | WO 2012145493 | 10/2012 |
| WO | WO 2013041606 | 3/2013 |
| WO | WO 2013053871 | 4/2013 |
| WO | WO 2013053873 | 4/2013 |
| WO | WO 2013055987 | 4/2013 |
| WO | WO 2013055990 | 4/2013 |
| WO | WO 2013055993 | 4/2013 |
| WO | WO 2013093809 | 6/2013 |
| WO | WO 2013177481 | 11/2013 |
| WO | WO 2014011518 | 1/2014 |
| WO | WO 2014011519 | 1/2014 |
| WO | WO 2014022679 | 2/2014 |
| WO | WO2014057117 A1 * 4/2014 ............. A61P 39/00 |
| WO | WO 2014055648 | 4/2014 |
| WO | WO 2014057072 | 4/2014 |
| WO | WO 2014057073 | 4/2014 |
| WO | WO 2014057074 | 4/2014 |
| WO | WO 2014057117 | 4/2014 |
| WO | WO 2014057118 | 4/2014 |
| WO | WO 2014057122 | 4/2014 |
| WO | WO 2015031693 | 3/2015 |
| WO | WO 2015042246 | 3/2015 |
| WO | 2015052321 A1 | 4/2015 |
| WO | 2015052322 A1 | 4/2015 |
| WO | WO 2015052534 | 4/2015 |
| WO | WO 2015095423 | 6/2015 |
| WO | 2015157297 A | 10/2015 |
| WO | WO 2015153514 | 10/2015 |
| WO | WO2015157297 A1 * 10/2015 ........... A61K 39/395 |
| WO | WO 2016000619 | 1/2016 |
| WO | WO 2016007235 | 1/2016 |
| WO | WO 2016011160 | 1/2016 |
| WO | WO 2016073380 | 5/2016 |
| WO | WO 2016081384 | 5/2016 |
| WO | WO 2016127052 | 8/2016 |
| WO | WO 2016166298 | 10/2016 |

(56) References Cited

FOREIGN PATENT DOCUMENTS

| WO | WO 2016166307 | 10/2016 |
|---|---|---|
| WO | WO 2016179517 | 11/2016 |
| WO | WO 2016189124 | 12/2016 |
| WO | WO 2016196792 | 12/2016 |
| WO | WO 2017004016 | 1/2017 |
| WO | WO 2017130076 | 8/2017 |

OTHER PUBLICATIONS

Wang, K., Wei, G. & Liu, D. CD19: a biomarker for B cell development, lymphoma diagnosis and therapy. Exp Hematol Oncol 1, 36 (2012). (Year: 2012).*
Chalouni C, Doll S. Fate of Antibody-Drug Conjugates in Cancer Cells. J Exp Clin Cancer Res. 2018;37(1):20. Published Feb. 6, 2018. (Year: 2018).*
Adair, J.R. et al., "Antibody-drug conjugates—a perfect synergy," Exp. Opin. Biol. Ther. (2012), pp. 1-16.
Adams et al., "Molecular modelling of a sequence-specific DNA-binding agent based on the pyrrolo[2,1-c][1,4]benzodiazepines," Pharm. Pharmacol. Commun. (1999) 5:555-560.
Aird, R.E. et al., "ABCB1 genetic polymorphism influences the pharmacology of the new pyrrolobenzodiazepine derivative SJG-136," Pharmacogenomics Journal (2008) 8(4):289-296.
Alley, M.C. et al., "SJG-136 (NSC 694501), a novel rationally designed DNA minor groove interstrand cross-linking agent with potent and broad spectrum antitumor activity. Part 2: Efficacy evaluations," Cancer Res. (2004) 64:6700-6706.
Alley, M.C., "Efficacy evaluations of SJG-136 (NSC 694501), a novel pyrrolobenzodiazepine dimer with broad spectrum antitumor activity," Proceedings of the American Association for Cancer Research Annual Meeting (Mar. 2002) 43:63.
Alley, S. C., "Contribution of Linker Stability to the Activities of Anticancer Immunoconjugates" Bioconjugate Chem 2008, 19, 759-765.
Althius, T. H. and Hess, H. J., "Synthesis and Identification of the Major Metabolites of Prazosin Formed in Dog and Rat," J. Medicinal Chem. (1977) 20(1):146-148.
Altuvia et al., "Ranking potential binding peptides to MHC molecules by a computational threading approach." J. Mol. Biol., 249, 244-250 (1995).
Amiel J., et al., "Heterozygous endothelin receptor B {EDNRB} mutations in isolated Hirschsprung disease," Hum. Mol. Genet. 5, 355-357, 1996.
Amir et al., "Self-Immolative Dendrimers," (2003) Angew. Chem. Int. Ed. 42:4494-4499.
Amsberry, et al, "The Lactonization of 2'-Hydroxyhydrocinnamic Acid Amides: A Potential Prodrug for Amines," (1990) J. Org. Chem. 55:5867-5877.
Antonow, D. et al., ""Synthesis of DNA-Interactive Pyrrolo [2,1-c][1,4] benzodiazepines (PBDs)"" Chemical Reviews, 2011, 111(4):2815-2864.
Antonow, D. et al., "Structure-activity relationships of monomeric C2-aryl pyrrolo[2,1-c][1,4]benzodiazepine (PBD) antitumor agents." J Med Chem. Apr. 8, 2010;53(7):2927-41.
Antonow, D. et al., "Parallel synthesis of a novel C2-aryl pyrrolo[2,1-c][1,4]benzodiazepine (PBD) library," J. Comb. Chem. (2007) 9:437-445.
Arai H., et al., ""Molecular cloning of human endothelin receptors and their expressiOn in vascular endothelial cells and smooth muscle cells,"" Jpn. Circ. J. 56, 1303-1307, 1992.
Arai H., et al., "The Human Endotbelin-B Receptor Gene. Structural Organization and Chromosomal Assignment," J. Biol. Chem. 268, 3463-3470, 1993.
Arima et al., "Studies on Tomaymycin, A New Antibiotic. I. Isolation and Properties of Tomaymycin," J. Antibiotics (1972) 25:437-444.
Arnould, S., ""Impact on the cell cycle and involvement of ATM, ATR, chk1 and chk2 kinases in the cytotoxicity of SJG-136, a new pyrrolobenzodiazepine dimer,"" Proceedings of the American Association for Cancer Research Annual Meeting (Mar. 2004) 45:1298, Abstract No. 5618.
Arnould, S., "Time-dependent cytotoxicity induced by SJG-136 (NSC 694501): influence of the rate of interstrand cross-link formation on DNA damage signaling," Mol. Canc. Therap. 5(6):1602-1609 (2006).
Attie T., et al., "Mutation of the endothelin-receptor B gene in Waardenburg-Hirschsprung disease," Hum. Mol. Genet. 4, 2407-2409, 1995.
Aue et al. "Fractionated subcutaneous rituximab is well-tolerated and preserves CD20 expression on tumor cells in patients with chronic lymphocytic leukemia." Haematologica. Feb. 2010;95(2):329-32.
Auricchio A., et al., "Endothelin-B receptor mutations in patients with isolated Hirschsprung disease from a non-inbred population," Hum. Mol. Genet. 5:351-354, 1996.
Axup et al., "Synthesis of site-specific antibody-drug conjugates using unnatural amino acids." Proc Natl Acad Sci U S A. Oct. 2, 2012; 109(40):16101-6.
Bahrenberg et al., ""Reduced Expression of PSCA, a Member of the LY-6 Family of Cell Surface Antigens, in Bladder, Esophagus, and Stomach Tumors,"" Biochem. Biophys. Res. Commun. (2000) 275(3):783-788.
Banker, G.S. et al., "Modern Pharmaceutics", Third edition, Marcel Dekker, New York (1996) 451 and 596.
Barel M., et al., "Evidence for a new transcript of the Epstein-Barr virus/C3d receptor (CR2, CD21) which is due to alternative exon usage," Mol. Immunol. 35, 1025-1031, 1998.
Barella et al., "Sequence variation of a novel heptahelical leucocyte receptor through alternative transcript formation," (1995) Biochem. J. 309:773-779.
Barnett T., et al., "Carcinoembryonic Antigen Family: Characterization of cDNAs Coding for NCA and CEA and Suggestion of Nonrandom Sequence Variation in Their Conserved Loop-Domains," Genomics 3, 59-66, 1988.
Batisse, et al., "A new delivery system for Auristatin in STxB-drug conjugate therapy." European J. Medicinal Chemistry, 2015, 95: 483-491.
Beck et al., "DNA Sequence Analysis of 66 kb of the Human MHC Class II Region Encoding a Cluster of Genes for Antigen Processing," (1992) J. Mol. Biol. 228:433-441.
Beck et al., "Evolutionary Dynamics of Non-coding Sequences Within the Class II Region of the Human MHC," (1996) J. Mol. Biol. 25 255:1-13.
Berge et al., "Pharmaceutical Salts," J. Pharm. Sci. (1977) 66:1-19.
Berry, J. M. et al., "Solid-phase synthesis of DNA-interactive pyrrolo[2,1-c][1,4]benzodiazepines," Tetrahedron Letters (2000) 41:6171-6174.
Blanc et al., "SAR3419: an anti-CD19-Maytansinoid Immunoconjugate for the treatment of B-cell malignancies," Clin Cancer Res., 2011, 17(20):6448-58.
Bloom et al., "Intrachain disulfide bond in the core hinge region of human lgG4." Protein Sci. Feb. 1997; 6(2):407-15.
Blumberg H., et al., ""Interleukin 20: Discovery, Receptor Identification, and Role in Epidermal Function,"" Cell 104, 9-19, 2001.
Borch et al., "Reorienting the immune system in the treatment of cancer by using anti-PD-1 and anti-PD-L1 antibodies." Drug Discov Today. Sep. 2015;20(9):1127-34.
Bose et al., "New Approaches to Pyrrolo[2,1-c][1,4]benzodiazepines: Synthesis, DNA-binding and cytotoxicity of DC-81," Tetrahedron, 48, 751-758 (1992).
Bose, D.S. et al., "Effect of linker length on DNA-binding affinity, cross-linking efficiency and cytotoxicity of C8 linked pyrrolobenzodiazepine dimers," J. Chem. Soc. Chem. Commun. (1992) 20:1518-1520.
Bose, D.S. et al., "Rational Design of a Highly Efficient Irreversible DNA Interstrand Cross-Linking Agent Based on the Pyrrolobenzodiazepine Ring System," J. Am. Chem. Soc., 114, 4939-4941 (1992).
Bourgeois C., et al., "Endothelin-1 and ETA Receptor Expression in Vascular Smooth Muscle Cells from Human Placenta: A New ETA

(56) References Cited

OTHER PUBLICATIONS

Receptor Messenger Ribonucleic Acid Is Generated by Alternative Splicing of Exon 3," J. Clin. Endocrinol. Metab. 82, 3116-3123, 1997.
Brand et al., "Prospect for anti-HER2 receptor therapy in breast cancer." Anticancer Res. Jan.-Feb. 2006;26(1B):463-70.
Brinster et al., "Introits increase transcriptional efficiency in transgenic mice," (1988) Proc. Natl. Acad. Sci. USA 85:836-840.
Buchman et al., "Comparison of Intron-Dependent and Intron-Independent Gene Expression," (1988) Mol. Cell. Biol. 8:4395-4405.
Buhrow, S.A., "LC-MS/MS assay and dog pharmacokinetics of the dimeric pyrrolobenzodiazepine SJG-136 (NSC 694501)," J. Chromat. B: Anal. Tech. Biomed. Life Sci. (2006) 840(1):56-62.
Burke, P.J. et al., "Anti-CD70 antibody-drug conjugates containing pyrrolobenzodiazepine dimers demonstrate robust antitumor activity," AACR National Meeting, Apr. 2012, Chicago, Illinois, Abstract No. 4631.
Burke, P.J. et al., "Novel immunoconjugates comprised of streptonigrin and 17-amino-geldanamycin attached via a dipeptide-p-aminobenzylamine linker system," Bioorg. Med. Chem. Lett., Apr. 2009, 19(10):2650-2653.
Burton, "Immunoglobulin G: functional sites." Mol Immunol. Mar. 1985; 22(3):161-206.
Calcutt, M.W., "Determination of chemically reduced pyrrolobenzodiazepine SJG-136 in human plasma by HPLC-MS/MS: application to an anticancer phase I dose escalation study," J. Mass Spectrom. (2008) 43(1):42-52.
Carl et al., "A Novel Connector Linkage Applicable in Prodrug Design," (1981) J. Med. Chem. 24:479-480.
Carlsson et al., "Protein Thiolation and Reversible Protein-Protein Conjugation," (1978) Biochem. J. 173:723-737.
Carter, P., "Potent antibody therapeutics by design," (2006) Nature Reviews Immunology 6:343-357.
Casset et al., "A peptide mimetic of an anti-CD4 monoclonal antibody by rational design." Biochem Biophys Res Commun. Jul. 18, 2003; 307(1):198-205.
CellTiter-Glo Luminescent Cell Viability Assay, Promega Corp. Technical Bulletin TB288, dated Jan. 13, 2012 (14 pages).
Chakravarty et al., "Plasmin-Activated Prodrugs for Cancer Chemotherapy. 2. Synthesis and Biological Activity of Peptidyl Derivatives of Doxorubicin," (1983) J. Med. Chern. 26:638-644.
Chan, J. and Watt, V.M., "eek and erk, new members of the eph subclass of receptor protein-tyrosine kinases," Oncogene 6 (6), 1057-1061 (1991).
Chang et al., "Molecular cloning of mesothelin, a differentiation antigen present on mesothelium, mesotheliomas, and ovarian cancers," Proc. Natl. Acad. Sci. U.S.A. 93 (1):136-140 (1996).
Chen et al., "Charge-based analysis of antibodies with engineered cysteines: From multiple peaks to a single main peak" mAbs 1:6, 563-571; Nov./Dec. 2009.
Chen, Z. et al., "A novel approach to the synthesis of cytotoxic C2-C3 unsaturated pyrrolo[2,1-c][1,4]benzodiazepines (PBDs) with conjugated acrylyl C2-substituents." Biorg. Med. Chem. Lett. (2004) 14:1547-1549.
Cheung, A., "Direct liquid chromatography determination of the reactive imine SJG-136 (NSC 694501)," J. Chromat. B: Anal. Techn. Biomed. Life Sci. (2005) 822(1-2):10-20.
Child et al., "Translational Control by an Upstream Open Reading Frame in the HER-2/neu Transcript," (1999) J. Bioi. Chern. 274: 24335-24341.
Cho et al., "Structure of the extracellular region of HER2 alone and in complex with the Herceptin Fab," Nature 421, 756-760, 2003.
Ciccodocolae al., ""Molecular characterization of a gene of the 'EGF family' expressed in undifferentiated human NTERA2 teratocarcinoma cells,"" EMBO J. 8 (7):1987-1991 (1989).
Cipolla, L., "Pyrrolo[2,1-c][1,4]benzodiazepine as a scaffold for the design and synthesis of anti-tumour drugs," Anti-Cancer Agents in Medicinal Chemistry (Jan. 2009) 9(1):1-31.
Clackson et al., "Making antibody fragments using phage display libraries," (1991) Nature, 352:624-628.
Clark H.F., et al., "The Secreted Protein Discovery Initiative (SPDI], a Large-Scale Effort to Identify Novel Human Secreted and Transmembrane Proteins: A Bioinformatics Assessment," Genome Res. 13, 2265-2270, 2003.
Clingen, P.H., "The role of nucleotide excision repair and homologous recomination in the sensitivity of mammalian cells to the minor groove crosslinking pyrrolo[2,1-c][1,4]benzodiazepine dimer SJG-136 (NSC694501)," Proceedings of the American Association for Cancer Research Annual Meeting (Jul. 2003) 44:524.
Clingen, P.H., "the XPF-ERCC1 endonuclease and homologous recombination contribute to the repair of minor groove DNA interstrand crosslinks in mammalian cells produced by the pyrrolo[2,1-c][1,4]benzodiazepine dimer SJG-136," Nucl. Acids Res. (2005) 33(10):3283-3291.
Clinical Trial, "Translational research: 4 ways to fix the clinical trial." 2011, http://www.nature.com/news/2011/110928/full/477526a.html.
ClinicalTrials.gov Identifier: NCT01239134, 2010, Trial of TRX518 (Anti-GITR mAb) in Stage III or IV Malignant Melanoma or Other Solid Tumors (TRX518-001). [online] [Retrieved Sep. 3, 2019] Retrieved from the internet <URL:https://clinicaltrials.gov/ct2/show/NCT01239134?term=NCT01239134&draw=2&rank=1>.
ClinicalTrials.gov Identifier: NCT02028403, 2015, [online] [Retrieved Aug. 29, 2019] Retrieved from the internet <URL:https://clinicaltrials.gov/ct2/show/NCT02028403>.
ClinicalTrials.gov Identifier: NCT02132754, 2014, Study of MK-4166 and MK-4166 in Combination With Pembrolizumab (MK-3475) in Participants With Advanced Solid Tumors (MK-4166-001). [online] [Retrieved Aug. 29, 2019] Retrieved from the internet <URL:https://clinicaltrials.gov/ct2/show/NCT02132754?term=NCT02132754&draw=2&rank=1>.
ClinicalTrials.gov Identifier: NCT02221960, 2014, A Phase 1 Study to Evaluate MEDI6383 Alone and in Combination With MEDI4736 in Adult Subjects With Select Advanced Solid Tumors. [online] [Retrieved Aug. 28, 2019] Retrieved from the internet <URL:https://clinicaltrials.gov/ct2/show/NCT02221960?term=NCT02221960&draw=2&rank=1>.
ClinicalTrials.gov Identifier: NCT02271945, 2014 A Study in Adult Subjects With Select Advanced Solid Tumors. [online] [Retrieved Aug. 27, 2019] Retrieved from the internet <URL: https://clinicaltrials.gov/ct2/show/NCT02271945?term=NCT02271945&draw=2&rank=1>.
ClinicalTrials.gov Identifier: NCT02298946, 2014, AMP-224, a PD-1 Inhibitor, With Stereotactic Body Radiation Therapy in Metastatic Colorectal Cancer [online] [Retrieved Aug. 28, 2019] Retrieved from the internet <URL: https://clinicaltrials.gov/ct2/show/NCT02298946?term=NCT02298946&draw=2&rank=1>.
ClinicalTrials.gov Identifier: NCT02315066, 2014, Study Of OX40 Agonist PF-04518600 Alone And In Combination With 4-1BB Agonist PF-05082566 [online] [Retrieved Sep. 3, 2019] Retrieved from the internet <URL: https://clinicaltrials.gov/ct2/show/NCT02315066?term=NCT02315066&draw=2&rank=1>.
ClinicalTrials.gov Identifier: NCT02318394, 2014, A Phase 1 Study of MEDI0562 in Adult Subjects With Selected Advanced Solid Tumors [online] [Retrieved Aug. 28, 2019] Retrieved from the internet <URL: https://clinicaltrials.gov/ct2/show/NCT02318394?term=NCT02318394&draw=2&rank=1>.
ClinicalTrials.gov Identifier: NCT02528357, 2015, GSK3174998 Alone or With Pembrolizumab in Subjects With Advanced Solid Tumors (ENGAGE-1) [online] [Retrieved Aug. 28, 2019] Retrieved from the internet <URL:https://clinicaltrials.gov/ct2/show/NCT02528357?term=NCT02528357&draw=2&rank=1>.
ClinicalTrials.gov Identifier: NCT02553499, 2015, Study of MK-1248 With and Without Pembrolizumab (MK-3475) for Participants With Advanced Solid Tumors (MK-1248-001) [online] [Retrieved Aug. 27, 2019] Retrieved from the internet <URL: https://clinicaltrials.gov/ct2/show/NCT02553499?term=NCT02553499&draw=2&rank=1>.
ClinicalTrials.gov Identifier: NCT02583165, 2015, Safety/Efficacy of MEDI-551 in Combination With Immunomodulating Therapies in Subjects With Aggressive B-cell Lymphomas. [online] [Retrieved

(56) References Cited

OTHER PUBLICATIONS

Aug. 27, 2019] Retrieved from the internet <URL: https://clinicaltrials.gov/ct2/show/NCT02583165?term=NCT02583165&draw=2&rank=1>.

ClinicalTrials.gov Identifier: NCT02598960, 2015, An Investigational Immuno-therapy Study of Experimental Medication BMS-986156, Given by Itself or in Combination With Nivolumab in Patients With Solid Cancers or Cancers That Have Spread. [online] [Retrieved Aug. 28, 2019] Retrieved from the internet <URL: https://clinicaltrials.gov/ct2/show/NCT02598960?term=NCT02598960&draw=2&rank=1>.

ClinicalTrials.gov Identifier: NCT02628574, 2015, Phase 1 Open-label Study of TRX518 Monotherapy and TRX518 in Combination With Gemcitabine, Pembrolizumab, or Nivolumab. [online] [Retrieved Sep. 3, 2019] Retrieved from the internet <URL: https://clinicaltrials.gov/ct2/show/NCT02628574?term=NCT02628574&draw=2&rank=1>.

ClinicalTrials.gov Identifier: NCT02669017, Study of ADCT-402 in Patients With Relapsed or Refractory B-cell Lineage Non Hodgkin Lymphoma (B-NHL) 2016 [online] Retrieved Dec. 17, 2020, Retrieved from the internet: <https://clinicaltrials.gov/ct2/show/results/NCT02669017?term=NCT02669017&draw=2&rank=1>.

ClinicalTrials.gov Identifier: NCT02923349, 2016, A Phase 1/2, Open-Label, Dose-Escalation, Safety Study of INCAGN01949 in Subjects With Advanced or Metastatic Solid Tumors. [online][Retrieved Aug. 28, 2019] Retrieved from the internet <URL: https://clinicaltrials.gov/ct2/show/NCT02923349?term=NCT02923349&draw=2&rank=1>.

ClinicalTrials.gov Identifier: NCT03209973, 2017, A Study of Tislelizumab as Monotherapy in Relapsed or Refractory Classical Hodgkin Lymphoma. [online] [Retrieved Aug. 28, 2019] Retrieved from the internet <URL: https://clinicaltrials.gov/ct2/show/NCT03209973?term=NCT03209973&draw=2&rank=1>.

ClinicalTrials.gov Identifier: NCT03277352, 2017, INCAGN01876 in Combination With Immune Therapies in Subjects With Advanced or Metastatic Malignancies. [online] [Retrieved Aug. 27, 2019] Retrieved from the internet <URL: https://clinicaltrials.gov/ct2/show/NCT03277352?term=NCT03277352&draw=2&rank=1>.

ClinicalTrials.gov Identifier: NCT02013804, 2013, A Phase 1 Multicenter Open-label Study to Evaluate the Safety Tolerability and PK of MEDI0680 (AMP-514) in Subjects With Advanced Malignancies. [online] [Retrieved Sep. 3, 2019] Retrieved from the internet <URL: https://clinicaltrials.gov/ct2/show/NCT02013804?term=NCT02013804&draw=2&rank=1>.

Coiffier et al., "A phase II, single-arm, multicentre study of coltuximab ravtansine (SAR3419) and rituximab in patients with relapsed or refractory diffuse large B-cell lymphoma." Br J Haematol. Jun. 2016;173(5):722-30.

Collins, "Generation and initial analysis of more than 15,000 full-length human and mouse eDNA sequences," Proc. Natl. Acad. Sci. U.S.A. 99 (26):16899-16903 (2002).

Cooper, N. et al., "Synthesis of novel PBDs as anti-tumour agents," Chem. Commun. (2002) 16:1764-1765.

Cooper, N., "Design, Synthesis and Evaluation of Novel C2-Aryl Pyrrolobenzodiazepines as Potential Anticancer Agents," Thesis submitted to School of Pharmacy, University of London, Dated Oct. 5, 2006.

Corey E. Quinn Je, Buhler KR, et al., "LuCap35: a new model of prostate cancer progression to androgen independence." The Prostate 2003;55:239-46.

Courtney, S. M. et al., "A new convenient procedure for the synthesis of pyrrolo[2,1-c][1,4]benzodiazepines", Tetrahedron Letters, vol. 34, No. 33, 5327-28 (1993).

Coussens L., et al., "Tyrosine Kinase Receptor with Extensive Homology to EGF Receptor Shares Chromosomal Location With neu Oncogene," Science (1985) 230(4730):1132-1139.

Cragg et al., "The alternative transcript of CD79b is overexpressed in B-CLL and inhibits signaling for apoptosis," Blood (2002) 100 (9):3068-3076.

Cree et al., "Methotrexate chemosensitivity by ATP luminescence in human leukemia cell lines and in breast cancer primary cultures: comparison of the TCA-100 assay with a clonogenic assay," (1995) AntiCancer Drugs 6:398-404.

Crouch et al., "The use• of ATP bioluminescence as a measure of cell proliferation and cytotoxicity," (1993) J. Immunol. Meth. 160:81-88.

Dall'Acqua, W. F. et al., "Antibody humanization by framework shuffling" Methods, 36, 43-60 (2005).

Dattolo, G. et al., "Polycondensed nitrogen heterocycles. IX. 5,6-dihydro-7H-pyrrolo[1,2-d][1,4]benzodiazepin-6-one," J. Heterocyclic. Chem. (1980) 17:701-703.

Davis et al., "Identification of a family of Fe receptor homo logs with preferential B cell expression," (2001) Proc. Natl. Acad. Sci. USA 98(17):9772-9777.

De Groot et al., ""Cascade-Release Dendrimers"" Liberate All End Groups upon a Single Triggering Event in the Dendritic Core, (2003) Angew. Chem. Int. Ed. 42:4490-4494.

De Groot et al., "Elongated Multiple Electronic Cascade and Cyclization Spacer Systems in Activatible Anticancer Prodrug for Enhanced Drug Release," (2001) J. Org. Chem. 66:8815-8830.

De Pascalis et al., "Grafting of "abbreviated" complementarity-determining regions containing specificity-determining residues essential for ligand contact to engineer a less immunogenic humanized monoclonal antibody." J Immunol. Sep. 15, 2002;169(6):3076-84.

Dennis et al., (2002) "Albumin Binding As A General Strategy For Improving The Pharmacokinetics Of Proteins" J Biol Chem. 277:35035-35043.

Dijke, P., et al., "Characterization of Type I Receptors for Transforming Growth Factor-beta and Activin," Science 264 (5155):101-104 (1994).

Dobner et al., "Differentiation-specific expression of a novel G protein-coupled receptor from Burkitt's lymphoma," (1992) Eur. J. Immunol. 22:2795-2799.

Dong, Q. et al., "Reductive cleavage of TROC groups under neutral conditions with cadmium-lead couple," Tetrahedron Lett. (1995) 36(32):5681-5682.

Dono et al., "Isolation and Characterization of the CRI PTO Autosomal Gene and Its X-linked Related Sequence," Am. J. Hum. Genet. 49:555-565, 1991.

Dornan et al., "Therapeutic potential of an anti-CD79b antibody-drug conjugate, anti-CD79b-vc-MMAE, for the treatment of non-Hodgkin lymphoma," (2009) Blood 114(13):2721-2729.

Dorner & Goldenberg, "Targeting CD22 as a strategy for treating systemic autoimmune diseases." Ther Clin Risk Manag. Oct. 2007;3(5):953-9.

Doronina et al., "Enhanced Activity of Monomethylauristatin F through Monoclonal Antibody Delivery: Effects of Linker Technology on Efficacy and Toxicity," (2006) Bioconj. Chem. 17:114-124.

Doronina, S.O. et al., "Development of potent monoclonal antibody auristatin conjugates for cancer therapy," Nature Biotech. (2003) 21:778-784.

Dorwald, F.Z., Side Reactions in Organic Synthesis: a Guide to Successful Synthesis Design, Weinheim: Wiley-VCH Verlag GmbH & Co., KGaA (2005) Preface.

Doyle, M., "Response of *Staphylococcus aureus* to subinhibitory concentrations of a sequence-selective, DNA minor groove cross-linking pyrrolobenzodiazepine dimer," J. Antimicrob. Chemo., Aug. 2009, 64(5):949-959.

Dubowchik et al, "Cathepsin B-sensitive dipeptide prodrugs. 1. A model study of structural requirements for efficient release of doxorubicin." Bioorg Med Chem Lett. Dec. 1, 1998; 8(23):3341-6.

Dubowchik et al, "Cathepsin B-sensitive dipeptide prodrugs. 2. Models of anticancer drugs paclitaxel (Taxol), mitomycin C and doxorubicin." Bioorganic & Medicinal Chemistry Letters, 8:3347-3352, (1998).

Dubowchik et al., "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity," Bioconjugate Chem. (2002) 13, 855-869.

Dubowchik, et al., "Monomethoxytrityl (MMT) as a Versatile Amino Protecting Group for Complex Prodrugs of Anticancer

(56) References Cited

OTHER PUBLICATIONS

Compounds Sensitive to Strong Acids, Bases and Nucleophiles," (1997) Tetrahedron Letters. 38:5257-5260.
Dumoutier L., et al., "Cutting Edge: STAT Activation By IL-19, IL-20 and mda-7 Through IL-20 Receptor Complexes of Two Types," J. Immunol. 167, 3545-3549, 2001.
Dupont, C. et al., "Synthesis of rhazinilam analogue acting as an inhibitor of tubulin assembly," Tetrahedron Lett. (2000) 41:5853-5856.
Ehsani A., et al., "Characterization of a New Allele of the Human ERBB2 Gene by Allele-Specific Competition Hybridization," (1993) Genomics 15, 426-429.
Elshourbagy N.A., et al., "Molecular Characterization and Regulation of the Human Endothelin Receptors," J. Biol. Chem. 268, 3873-3879, 1993.
Erickson et al., "Antibody-Maytansinoid Conjugates Are Activated in Targeted Cancer Cells by Lysosomal Degradation and Linker-Dependent Intracellular Processing," (2006) Cancer Res. 66(8): 4426-4433.
Farmer, J.D. et al., "Synthesis and DNA crosslinking ability of a dimeric anthramycin analog," Tetrahedron Letters (1988) 29(40):5105-5108, Abstract only.
Farmer, J.D. et al., "DNA binding properties of a new class of linked anthramycin analogs," Chemical Abstracts, Abstract No. 239940r, vol. 114, No. 25, 25 899-903 (1991).
Feild, J.A., et al., "Cloning and Functional Characterization of a Sodium-Dependent Phosphate Transporter Expressed in Human Lung and Small Intestine," (1999) Biochem. Biophys. Res. Commun. 258 (3):578-582.
Fey, T. et al., "Silica-supported TEMPO catalyst: synthesis and application in the anelli oxidation of alcohols," J. Org. Chem. (2001) 66:8154-8159.
Fields, G. and Noble, R. (1990) "Solid phase peptide synthesis utilizing 9-fluoroenylmethoxycarbonyl amino acids", Int. J. Peptide Protein Res. 35:161-214.
Firsching, A. et al., "Antiproliferative and angiostatic activity of suramin analogues," Cancer Res. (1995) 55:4957-4961.
Flanagan et al., "The ephrins and Eph receptors in neural development," Annu. Rev. Neurosci. 21:309-345 (1998).
Foloppe, M.P. et al., "DNA-binding properties of pyrrolo[2,1-c][1,4]benzodiazephine N10-C11 amidines," Eur. J. Med. Chem., 31, 407-410 (1996).
Fox et al., "cDNA cloning and tissue distribution of five human EPH-like receptor protein-tyrosine kinases," Oncogene 10 (5):897-905 (1995).
Frey F, et al. Abstract 7002. "Optimizing chimeric antigen receptor (CAR) T cell therapy for adult patients with relapsed or refractory (r/r) acute lymphoblastic leukemia (ALL)." DOI: 10.1200/JCO.2016.34.15_suppl.7002 Journal of Clinical Oncology 34, No. 15_suppl (May 20, 2016) 7002-7002.
Fuchs S., et al., "Functional Characterization of Three Mutations of the Endothelin B Receptor Gene in Patients with Hirschsprung's Disease: Evidence for Selective Loss of Gi Coupling," Mol. Med. 7, 115-124, 2001.
Fujimoto et al., "CD19 regulates B lymphocyte responses to transmembrane signals." Semin Immunol. Aug. 1998;10(4):267-77.
Fujisaku et al., "Genomic Organization and Polymorphisms of the Human C3d/Epstein-Barr Virus Receptor," (1989) J. Biol. Chem. 264 (4):2118-2125.
Fujisawa Pharmaceutical Co. Ltd., "Benzodiazepine derivatives," SciFinder Scholar, 2-3 (2002).
Fujisawa Pharmaceutical Co., Ltd., Abstract No. 139983k,"Benzodiazepine derivatives", Chemical Abstracts, vol. 99, No. 17, 603 (1983).
Fujisawa Pharmaceutical Co., Ltd., Abstract No. 72145x,"Benzodiazepine derivatives", Chemical Abstracts, vol. 98, No. 9, 638 (1983).
Fukuyama, T. et al., "Total Synthesis of (+)-Porothramycin B," Tetrahedron Letters, vol. 34, 16, 2577-2580 (1993).

Gallmeier, E., "Targeted disruption of FANCC and FANCG in human cancer provides a preclinical model for specific therapeutic options," Gastroenterology (2006) 130(7):2145-2154.
Gary S.C., et al., "cDNA cloning chromosomal localization, and expression analysis of human BEHAB/brevican, a brain specific proteoglycan regulated during cortical development and in glioma," Gene 256, 139-147, 2000.
Gaugitsch, H.W., et al., "A novel transiently expressed, integral membrane protein linked to cell activation. Molecular cloning via the rapid degradation signal AUUUA.," (1992) J. Biol. Chem. 267 (16):11267-11273.
Gavezzotti A., "Are crystal structures predictable?" Acc. Chem. Res. (1994) 27:309-314.
Geiser et al "Automation of solid-phase peptide synthesis" in Macromolecular Sequencing and Synthesis, Alan R. Liss, Inc., 1988, pp. 199-218.
Genbank accession No. X58957.1 (2008).
Genbank accession No. 11038674 (2013).
Genbank accession No. AAAL07473.1 (2001).
Genbank accession No. AAC51773.1 (2010).
Genbank accession No. AAD22635.1 (1999).
Genbank accession No. AAF25807.1 (2010).
Genbank accession No. AB040878 (2001).
Genbank accession No. AF116456 (1999).
Genbank accession No. AF125304.1 (1999).
Genbank accession No. AF177937.1 (2000).
Genbank accession No. AF179274 (2001).
Genbank accession No. AF229053 (2000).
Genbank accession No. AF343662 (2001).
Genbank accession No. AF343663 (2001).
Genbank accession No. AF343664 (2001).
Genbank accession No. AF343665 (2001).
Genbank accession No. AF361486 (2003).
Genbank accession No. AF369794 (2001).
Genbank accession No. AF397453 (2001).
Genbank accession No. AF414120.1 (2001).
Genbank accession No. AF455138 (2003).
Genbank accession No. AJ297436 (2008).
Genbank accession No. AK026467 (2006).
Genbank accession No. AK089756 (2010).
Genbank accession No. AK090423 (2006).
Genbank accession No. AK090475 (2006).
Genbank accession No. AL834187 (2008).
Genbank accession No. AX092328 (2001).
Genbank accession No. AY158090 (2003).
Genbank accession No. AY260763 (2003).
Genbank accession No. AY275463 (2003).
Genbank accession No. AY358085 (2003).
Genbank accession No. AY358628 (2003).
Genbank accession No. AY358907 (2003).
Genbank accession No. AY506558 (2004).
Genbank Accession No. BAB15489.1 (2006).
Genbank accession No. BC017023 (2006).
Genbank accession No. CAA41728.1 (2008).
Genbank accession No. CAA53576.1 (2008).
Genbank accession No. CAA76847.1 (2001).
Genbank accession No. CAF85723 (2004).
Genbank accession No. CQ782436 (2004).
Genbank accession No. M11730 (1995).
Genbank accession No. M18728 (1995).
Genbank accession No. M26004 (1993).
Genbank accession No. NM_000626 (2013).
Genbank accession No. NM_001203 (2013).
Genbank accession No. NM_003212 (2013).
Genbank accession No. NM_003486 (2013).
Genbank accession No. NM_004442 (2013).
Genbank accession No. NM_005823 (2013).
Genbank accession No. NM_006424 (2013).
Genbank accession No. NM_012449 (2013).
Genbank accession No. NM_017636 (2013).
Genbank accession No. NM_030764 (2013).
Genbank Accession No. NP_001171569 (2019).
Genbank accession No. NP_001194 (2013).

(56) References Cited

OTHER PUBLICATIONS

Genbank accession No. NP_001707.1 (2013).
Genbank accession No. NP_001773.1 (2013).
Genbank accession No. NP_001774.10 (2013).
Genbank accession No. NP_002552.2 (2013).
Genbank accession No. NP_003203 (2013).
Genbank accession No. NP_005573.1 (2007).
Genbank accession No. NP_112571.1 (2007).
Genbank accession No. U64863.10 (2005).
Genbank accession No. X75962.1 (2008).
Geoghegan & Stroh, "Site-Directed Conjugation of Nonpeptide Groups to Peptides and Proteins via Periodate Oxidation of a 2-Amino Alcohol. Application to Modification at N-Terminal Serine," (1992) Bioconjugate Chem. 3:138-146.
Getz et al., "A Comparison between the Sulfhydryl Reductants Tris(2-carboxyethyl)phosphine and Dithiothreitol for Use in Protein Biochemistry," (1999) Anal. Biochem. vol. 273:73-80.
Glynne-Jones et al., "Tenb2, A Proteogl Ycan Identified In Prostate Cancer That Is Associated With Disease Progression And Androgen Independence," (2001) Int J Cancer. Oct. 15; 94(2): 178-184.
Gomez et al., "Effect of temperature, pH, dissolved oxygen, and hydrolysate on the formation of triple light chain antibodies in cell culture." Biotechnol Prog. Sep.-Oct. 2010; 26(5):1438-45.
Gomez et al., "Triple light chain antibodies: factors that influence its formation in cell culture." Biotechnol Bioeng. Mar. 1, 2010; 105(4):748-60.
Gonzalez et al. "Abstract 3204: INCAGN01949: an anti-OX40 agonist antibody with the potential to enhance tumor-specific T-Cells responsiveness, while selectively depleting intratumoral regulatory T Cells." 2016, DOI: 10.1158/1538-7445.
Gordon et al., "Somatic hypermutation of the B cell receptor genes B29 (Igβ, CD79b) and mb1 (Igα, CD79a)," PNAS, 2003, vol. 100, No. 7, 4126-4131.
Greene & Wuts, Protective Groups in Organic Synthesis, John Wiley & Sons, 2nd ed., Ch 7, 315-345 (1991).
Greene, et al., Protective Groups in Organic Synthesis, John Wiley & Sons (1999) 3rd Edition, 23-200.
Greene, et al., Protective Groups in Organic Synthesis, John Wiley & Sons (1999) 3rd Edition, 503-549.
Gregson, S. et al., "Synthesis of a novel C2/C2'-exo unsaturated pyrrolobenzodiazepine cross-linking agent with remarkable DNA binding affinity and cytotoxicity," Chemical Communications, 797-798 (1999).
Gregson, S.J. et al., "Effect of C2/C3-endo unsaturation on the cytotoxicity and DNA-binding reactivity of pyrrolo-[2,1-c][1,4]-benzodiazepines," Bioorg. Med. Chem. Lett. (2000) 10(16):1849-1851.
Gregson, S.J. et al., "Linker length modulates DNA cross-linking reactivity and cytotoxic potency of C8/C8' ether-linked C2-exo-unsaturated pyrrolo[2,1-c][1,4]benzodiazepine (PBD) dimers," J. Med. Chem. (2004) 1161-1174.
Gregson, S.J. et al., "Synthesis of the first example of a C2-C3/C2'-C3'-endo unsaturated pyrrolo[2,1-c][1,4]benzodiazepine dimer," Biorg. Med. Chem. Lett. (2001) 11:2859-2862.
Gregson, S.J. et al., "Synthesis of the first examples of A-C8/C-C2 amide-linked pyrrolo[2,1-c][1,4]benzodiazepine dimers," Biorg. Med. Chem. Lett. (2003) 13:2277-2280.
Gregson, S.J. et al., "Design, Synthesis and Evaluation of a Novel Pyrrolobenzodiazepine DNA-Interactive Agent with Highly Efficient Cross-Linking Ability and Potent Cytotoxicity", J. Med. Chem., 44: 737-748 (2001).
Gregson, S.J. et al., "Effect of C2-exo Unsaturation on the Cytotoxicity and DNA-Binding Reactivity of Pyrrolo[2,1-c][1,4]benzodiazepines", Bioorganic & Medicinal Chemistry Letters, 10: 1845-1847 (2000).
Gu Z., et al., "Prostate stem cell antigen (PSCA) expression increases with high gleason score, advanced stage and bone metastasis in prostate cancer," Oncogene 19, 1288-1296, 2000.

Guichard, S.M., "Influence of P-glycoprotein expression on in vitro cytotoxicity and in vivo antitumour activity of the novel pyrrolobenzodiazepine dimer SJG-136," Eur. J. Cancer (2005) 41(12):1811-1818.
Guiotto, A. et al., "Synthesis of novel C7-aryl substituted pyrrolo[2,1-c][1,4]benzodiazepines (PBDs) via Pro-N10-troc protection and suzuki coupling," Bioorganic & Medicinal Chemistry Letters, 8, No. 21, 3017-3018 (1998).
Guselnikov et al., "A family of highly diverse human and mouse genes structurally links leukocyte FcR, gp42 and PECAM-1," Immunogenetics 54 (2):87-95 (2002).
Ha et al., "Molecular Cloning And Expression Pattern Of A Human Gene Homologous To The Murine mb-1 Gene," (1992) J. Immunol. 148(5):1526-1531.
Hadjivassileva, T., "Antibacterial activity of pyrrolobenzodiazepine dimers, a novel group of DNA-binding compounds," Abstracts of the Interscience Conference on Antimicrobial Agents and Chemotherapy (Oct.-Nov. 2004) 44:202.
Hadjivassileva, T., "Interactions of pyrrolobenzodiazepine dimers and duplex DNA from methicillin-resistant *Staphylococcus aureus*," Int. J. Antimicrob. Agents (2007) 29(6):672-678.
Hadjivassileva, T., "Pyrrolobenzodiazepine dimers: novel sequence-selective, DNA-interactive, cross-linking agents with activity against Gram-positive bacteria," J. Antimicrob. Chemo. (2005) 56(3):513-518.
Haendler B., et al., "Molecular Cloning of Human Endothelin (ET) Receptors ETA and ETB," J. Cardiovasc. Pharmacal. 20, s1-S4, 1992.
Hamaguchi, A., "DNA cross-linking and in vivo antitumour activity of the extended pyrrolo[2,1-c][1,4]benzodiazepine dimer SG2057 (DRG-16)," EJC Supplements (Nov. 2006) 4(12):96.
Hamann P. "Monoclonal antibody-drug conjugates," (2005) Expert Opin. Ther. Patents 15(9):1087-1103.
Hamblett et al., "Effects of Drug Loading on the Antitumor Activity of a Monoclonal Antibody Drug Conjugate," (2004) Clin. Cancer Res. 10:7063-7070.
Handbook of Food Additives, 2nd Ed. (eds. M. Ash and I. Ash), Synapse Information Resources, Inc., Endicott, New York, USA (2001).
Handbook of Pharmaceutical Excipients, 2nd edition, 1994, Edited by Ainley Wade and Paul J. Weller.
Hara et al., "DC 102, a new glycosidic pyrrolo(1,4)benzodiazepine antibiotic produced by *Streptomyces* sp.", J. Antibiotics, 41, 702-704 (1988).
Hartley, "The development of pyrrolobenzodiazepines as antitumour agents", Expert Opinion on Investigational Drugs, Ashley Publications Ltd., vol. 28, No. 6, Jan. 1, 2011, pp. 733-744.
Hartley, J.A. et al., "SG2285, a novel C2-aryl-substituted pyrrolobenzodiazepine dimer prodrug that cross-links DNA and exerts highly potent antitumor activity," Cancer Res., Sep. 2010, 70(17):6849-6858.
Hartley, J.A. et al., "SJG-136 (NSC 694501), a novel rationally designed DNA minor groove interstrand cross-linking agent with potent and broad spectrum antitumor activity. Part 1: Cellular pharmacology, in vitro and initial in vivo antitumor activity," Cancer Res. (2004) 64:6693-6699.
Hartley, J.A., "In vitro antitumor activity and in vivo DNA interstrand crosslinking by the novel pyrrolobenzodiazepine dimer SJG-136 (NSC 694501)," Proceedings of the American Association for Cancer Research Annual Meeting (Mar. 2002) 43:489.
Hartley, J.A., "SJG-136 (NSC-D694501)—a novel DNA sequence specific minor groove crosslinking agent with significant antitumor activity," Proceedings of the American Association for Cancer Research Annual Meeting (Mar. 2000) 41:425.
Hasegawa et al., "CD19 can regulate B lymphocyte signal transduction independent of complement activation." J Immunol. Sep. 15, 2001;167(6):3190-200.
Hashimoto et al., "Chromosomal localization, genomic structure, and allelic polymorphism of the human CD79a (Ig-alpha/mb-1) gene," (1994) Immunogenetics 40(4):287-295.
Hay et al., "A 2-Nitroimidazole Carbamate Prodrug Of 5-Amin0-1-(Chloromethyl)-3-[(5,6,7-Trimethoxyindol-2-Yl)Carbonyl]-1,2-

(56) References Cited

OTHER PUBLICATIONS

Dihydr0-3h-Benz[E]Indole (Amino-Seco-Cbi-Tmi) For Use With Adept And Gdept," (1999) Bioorg. Med. Chem. Lett. 9:2237-2242.
Herdwijn et al., "Synthesis of trans(+)6-phenoxyacetamido-1-methylene-3,3-dicarboxymethyl-1-carbapenam," Canadian Journal of Chemistry. 1982, 60, 2903-2907.
Hermanson, G.T., "Heterobifunctional Cross-linkers," (1996) Bioconjugate Techniques; Academic Press: New York, p. 228-286.
Hezareh et al., "Effector function activities of a panel of mutants of a broadly neutralizing antibody against human immunodeficiency virus type 1." J Virol. Dec. 2001;75(24):12161-8.
Hochhauser, D., "Phase I study of sequence-selective minor groove DNA binding agent SJG-136 in patients with advanced solid tumors," Clin. Cancer Res., Mar. 2009, 15(6):2140-2147.
Hochlowski, J. et al., "Abbeymycin, a new anthramycin-type antibiotic produced by a streptomycete," J. Antibiotics, 40, 145-148 (1987).
Hoelzer, "Targeted therapy with monoclonal antibodies in acute lymphoblastic leukemia." Curr Opin Oncol. Nov. 2013;25(6):701-6.
Hofstra R.M.W., et al., "A homozygous mUtation in the endothelin-3 gene associated with a combined Waardenburg type 2 and Hirschsprung phenotype (Shah-Waardenburg syndrome)" Nat. Genet. 12, 445-447, 1996.
Hofstra R.M.W., et al., "Mutations in Hirschsprung Disease: When Does a Mutation Contribute to the Phenotype," Eur. J. Hum. Genet. 5, 180-185, 1997.
Horie et al., "Identification and Characterization of TMEFF2, a Novel Survival Factor for Hippocampal and Mesencephalic Neurons," (2000) Genomics 67: 146-152.
Horwood et al., "Bruton's tyrosine kinase is required for TLR2 and TLR4-induced TNF, but not IL-6, production." J Immunol. Mar. 15, 2006;176(6):3635-41.
Howard, et al., "Design, synthesis and biological evaluation of ZC-423, a novel C2-aryl substituted pyrrolobenzodiazepine (PBD) dimer," Clinical Cancer Research (2005) 11(23):9015S-9016S (A205).
Howard, P.W. et al., "Synthesis of a novel C2/C2'-aryl-substituted pyrrolo[2,1-c][1,4]benzodiazepine dimer prodrug with improved water solubility and reduced DNA reaction rate," Bioorg. Med. Chem., Sep. 2009, In Press, 4 pages now: Sep. 2009, 19:6463-6466.
Howard, P.W. et al., "The design, synthesis and biological evaluation of a set of C2-aryl substituted pyrrolo[2,1-c][1,4]benzodiazepine dimers," EJC Supplements (2006) 4(12):95—Poster Abstract 301.
Howard, P.W., "Design, synthesis and biological evaluation of novel C2-aryl-substituted pyrrolo[2,1-c][1,4]benzodiazepine monomers," Proceedings of the American Association for Cancer Research Annual Meeting (Apr. 2006) 47:132.
Hubert, R.S., et al., "STEAP: A prostate-specific cell-surface antigen highly expressed in human prostate tumors," (1999) Proc. Natl. Acad. Sci. U.S.A. 96 (25):14523-14528.
Humphreys et al., "Formation of dimeric Fabs in *Escherichia coli*: effect of hinge size and isotype, presence of interchain disulphide bond, Fab' expression levels, tail piece sequences and growth conditions." J Immunol Methods. Dec. 1, 1997; 209(2):193-202.
Hurley, L. and Needham-Vandevanter, D., "Covalent Binding of Antitumor Antibiotics in the Minor Groove of DNA. Mechanism of Action of CC-1065 and the yrrolo(1,4)benzodiazepines," Acc. Chem. Res., 19, 230-237 (1986).
Ide et al., "Cloning of human bone morphogenetic protein type IB receptor (BMPRIB) and its expression in prostate cancer in comparison with other BMPRs," Oncogene (1997) 14, 1377-1382.
Iida, H. et al. "Design and synthesis of pyrrolo[2,1-c][1,4]benzodiazepine (PBD)-polyaminoalkyl conjugates by the use of SNA4 reaction 2-nitro-5-fluorobenzoate precursor as key reaction," Heterocycles (2004) 62:693-711.
Illidge & Morschhauser, "Radioimmunotherapy in follicular lymphoma." Best Pract Res Clin Haematol. Jun. 2011;24(2):279-93.
International Search Report and Written Opinion for Application No. PCT/EP2013/071346 dated Feb. 5, 2014 (13 pages).
International Search Report and Written Opinion for Application No. PCT/EP2016/058370 dated Jun. 23, 2016 (15 pages).
International Search Report and Written Opinion for Application No. PCT/GB2014/053053 dated Feb. 2, 2015 (6 pages).
International Search Report and Written Opinion for Application No. PCT/EP2018/060215 dated Oct. 9, 2018 (28 pages).
International Search Report and Written Opinion for Application No. PCT/EP2018/065873 dated Oct. 18, 2018 (11 pages).
Itoh et al., "Application of Inverse Substrates to Trypsin-Catalyzed Peptide Synthesis" Bioorg. Chem., 24(1): 59-68 (1996).
Janjigian, Y.Y., "A phase I trial of SJG-136 (NSC#694501) in advanced solid tumors," Cancer Chemotherapy and Pharmacology, Aug. 2009, 65(5):833-838.
Jeffrey et al., "Development and properties of beta-glucuronide linkers for monoclonal antibody-drug conjugates." Bioconjugate Chemistry, 5, 2006, 17, 831-840. (Abstract).
Jeffrey, S.C., "Design, synthesis, and in vitro evaluation of dipeptide-based antibody minor groove binder conjugates," J. Med. Chem. (2005) 48(5):1344-1358.
Jespers, L. S., "Guiding the Selection of Human Antibodies from Phage Display Repertoires to a Single Epitope of an Antigen" Nature Biotech., 12, 899-903 (1994).
Jia, L., "Interspecies differences in pharmacokinetics and time-dissociated toxicokinetics of SJG-136," Proceedings of the American Association for Cancer Research Annual Meeting (Mar. 2004) 45:487.
Jia, L., "Use of the comet assay as a surrogate biomarker for the in vivo measurement of DNA damage to lymphocytes," Proceedings of the American Association for Cancer Research Annual Meeting (Mar. 2004) 45:452-453.
Jiang et al., "A novel antibody-drug conjugate anti-CD19(Fab)-LDM in the treatment of B-cell non-Hodgkin lymphoma xenografts with enhanced anticancer activity." J Drug Target. 2016;24(1):47-57.
Johnson & Goldin, "The clinical impact of screening and other experimental tumor studies." Cancer Treat Rev. Mar. 1975; 2(1):1-31.
Jones et al., "Releasable Luciferin—Transporter Conjugates: Tools for the Real-Time Analysis of Cellular Uptake and Release," J. Am. Chem. Soc., 2006, 128, 6526-6527.
Jonsson et al., "Human class II DNA and DOB genes display low sequence variability," (1989) Immunogenetics 29(6):411-413.
Jordan, V.C., ""Tamoxifen: a most unlikely pioneering medicine,"" Nature Reviews: Drug Discovery (2003) 2:205-213.
Junutula et al., "Rapid identification of reactive cysteine residues for site-specific labeling of antibody-Fabs," (2008) Jour of Immun. Methods 332:41-52.
Junutula, et al., "Site-specific conjugation of a cytotoxic drug to an antibody improves the therapeutic index," 2008b Nature Biotech., 26(8):925-932.
Kabat et al., Sequences of proteins of immunological interest, 5 ed. (NIH National Technical Information Service, 1991).
Kamal et al., "Synthesis and DNA-binding affinity of A-C8/C-C2 alkoxyamido-linked pyrrolo[2,1-c][1,4]benzodiazepine dimers" Biorg. Med. Chem. Lett. (2003) 13(22): 3955-3958.
Kamal, A. et al., "Design, synthesis and evaluation of new noncross-linking pyrrolobenzodiazepine dimers with efficient DNA binding ability and potent antitumor activity," J. Med. Chem. (2002) 45:4679-4688.
Kamal, A., "Development of pyrrolo[2,1-c][1,4]benzodiazepine beta-galactoside prodrugs for selective therapy of cancer by ADEPT and PMT," Chemmedchem (2008) 3:794-802.
Kamal, A., "Remarkable DNA binding affinity and potential anticancer activity of pyrrolo[2,1-c][1,4]benzodiazepine-naphthalamide conjugates linked through piperazine side-armed alkane spacers," Bioorg. Med. Chem. (2008) 16(15):7218-7224.
Kamal, A., "Remarkable enhancement in the DNA-binding ability of C2-fluoro substituted pyrrolo[2,1-c][1,4]benzodiazepines and their anticancer potential," Bioorg. Med. Chem., Jan. 2009, 17(4):1557-1572.
Kamal, A., "Synthesis of fluorinated analogues of SJG-136 and their DNA-binding potential," Bioorg. Med. Chem. Lett (2004) 14(22):5699-5702.

(56) References Cited

OTHER PUBLICATIONS

Kamal, A., et al., "An Efficient Synthesis of Pyrrolo[2,1-c][1,4] Benzodiazepine Antibiotics via Reductive Cyclization," Bioorg. Med. Chem. Ltrs, 7, No. 14, 1825-1828 (1997).
Kamal, A., et al., "Synthesis of Pyrrolo [2,1-c][1,4]-Benzodiazepene Antibiotics: Oxidation of Cyclic Secondary Amine with TPAP", Tetrahedron, v. 53, No. 9, 3223-3230 (1997).
Kamal, et al., "Synthesis of pyrrolo[2,1-c][1,4]benzodiazepines via reductive cyclization of w-azido carbonyl compounds by TMSI: an efficient preparation of antibiotic DC-81 and its dimers," Biorg. Med. Chem. Lett. (2000) 10:2311-2313.
Kaneko, T. et al., "Bicyclic and tricyclic analogues of anthramycin," J. Med. Chem. (1985) 28:388-392.
Kang, G.-D. et al., "Synthesis of a novel C2-aryl substituted 1,2-unsaturated pyrrolobenzodiazepine," Chem. Commun. (2003) 1680-1689.
Kantarjian et al., "Inotuzumab Ozogamicin versus Standard Therapy for Acute Lymphoblastic Leukemia." 2016,N Engl J Med 2016; 375:740-753.
Kasahara et al., "Nucleotide sequence of a chimpanzee DOB eDNA clone," (1989) Immunogenetics 30(1):66-68.
King et al., "Facile synthesis of maleimide bifunctional Jinkers," (2002) Tetrahedron Letters 43:1987-1990.
Kingsbury et al., "A Novel Peptide Delivery System Involving Peptidase Activated Prodrugs as Antimicrobial Agents. Synthesis and Biological Activity of Peptidyl Derivatives of 5 Fluorouracil," (1984) J. Med. Chem. 27:1447-1451.
Kohn, K., "Anthramycin," Antibiotics III, Springer-Verlag, NY, 3-11 (1975).
Kojima et al., "Molecular Cloning and Expression of Megakaryocyte Potentiating Factor eDNA," The Journal of Biological Chemistry, vol. 270, No. 37, Issue of Sep. 15, pp. 21984-21990, 1995.
Konishi, M. et al., "Chicamycin, a new antitumor antibiotic II. Structure determination of chicamycins A and B," J. Antibiotics, 37, 200-206 (1984).
Kovtun et al., "Antibody-Drug Conjugates Designed to Eradicate Tumors with Homogeneous and Heterogeneous Expression of the Target Antigen," (2006) Cancer Res. 66(6):3214-3121.
Kuhns J.J., et al., "Poor Binding of a HER-2/neu Epitope (GP2) to HLA-A2.1 Is due to a Lack of Interactions with the Center of the Peptide," J. Biol. Chem. 274, 36422-36427, 1999.
Kunimoto et al., "Mazethramycin, a new member of anthramycin group antibiotics," J. Antibiotics, 33, 665-667 (1980).
Kurebayashi et al., "Isolation and characterization of a new human breast cancer cell line, KPL-4, expressing the Erb B family receptors and interleukin.6," (1999) Brit. Jour. Cancer 79(5-6):707-717.
Lambert J., "Drug-conjugated monoclonal antibodies for the treatment of cancer," (2005) Current Opin. In Pharmacal. 5:543-549.
Langley, D.R. and Thurston, D.E., "A versatile and efficient synthesis of carbinolamine-containing pyrrolo[1,4]benzodiazepines via the cyclization of N-92-aminobenzoyl)pyrrolidine-2-carboxaldehyde diethyl thioacetals: total synthesis of prothracarcin," J. Org. Chem., 52, 91-97 (1987).
Langlois, N. et al., "Synthesis and cytotoxicity on sensitive and doxorubicin-resistant cell lines of new pyrrolo[2,1-c][1,4]benzodiazepines related to anthramycin," J. Med. Chem. (2001) 44:3754-3757.
Larhammar et al., "Sequence of Gene and eDNA Encoding Murine Major Histocompatibility Complex Class II Gene AP2*," (1985) J. Biol. Chem. 260(26):14111-14119.
Launay et al., "TRPM4 Is a Ca2+-Activated Nonselective Cation Channel Mediating Cell Membrane Depolarization," Cell 109 (3):397-407 (2002).
Law et al., "Lymphocyte Activation Antigen CD70 Expressed by Renal Cell Carcinoma Is a Potential Therapeutic Target for Anti-CD70 Antibody-Drug Conjugates," (2006) Cancer Res. 66(4):2328-2337.
Lazar et al., "A molecular immunology approach to antibody humanization and functional optimization" Molecular Immunology, 2007, 44(8), 1986-1998.
Le et al., "Primary structure and expression of a naturally truncated human P2X ATP receptor subunit from brain and immune system," (1997) FEBS Lett. 418(1-2):195-199.
Leber, J.D. et al., "A revised structure for sibiromycin," J. Am. Chem. Soc., 110, 2992-2993 (1988).
Leimgruber, W. et al., "Isolation and characterization of anthramycin, a new antitumor antibiotic," J. Am. Chem. Soc., 87, 5791-5793 (1965).
Leimgruber, W. et al., "The structure of anthramycin," J. Am. Chem. Soc., 87, 5793-5795 (1965).
Leimgruber, W. et al., "Total synthesis of anthramycin," J. Am. Chem. Soc., 90, 5641-5643 (1968).
Leonard et al., "Epratuzumab, a humanized anti-CD22 antibody, in aggressive non-Hodgkin's lymphoma: phase I/II clinical trial results." Clin Cancer Res. Aug. 15, 2004;10(16):5327-34.
Levenson et al., "MCF-7: The First Hormone-responsive Breast Cancer Cell Line," (1997) Cancer Res. 57(15):3071-3078.
Lewis Phillips et al., "Targeting HER2-Positive Breast Cancer with Trastuzumab-DM1, an Antibody-Cytotoxic Drug Conjugate," Cancer Res, 2008, 68: (22).
Li et al., "A Mini-Review for Cancer Immunotherapy: Molecular Understanding of PD-1/PD-L1 Pathway & Translational Blockade of Immune Checkpoints." Int J Mol Sci. Jul. 18, 2016;17(7):1151.
Liang et al., "The Gene for a Novel Transmembrane Protein Containing Epidermal Growth Factor and Follistatin Domains Is Frequently Hypermethylated in Human Tumor Cells," (2000) Cancer Res. 60:4907-4912.
Lonberg, "Fully Human antibodies from transgenic mouse and phage display platforms" Curr. Opinion, 20(4), 450-459 (2008).
Lown et al., "Molecular Mechanism of Binding of Pyrrolo(1,4)benzodiazepine antitumour agents to deoxyribonucleic acid-anthramycin and tomaymycin," Biochem. Pharmacol. (1979), 28 (13), 2017-2026.
Manfre et al., "Syntheses of Proline Analogues as Potential Mechanism-Based Inhibitors of Proline Dehydrogenase: 4-Methylene-L-, (E)- and (Z)-4-(Fluoromethylene)-L-, cis- and trans-5-Ethynyl-(±)-, and cis- and trans-5-Vinyl-L-proline," J. Org. Chem. 1992, 57, 2060-2065.
Marin, D., "Voltammetric studies of the interaction of pyrrolo[2,1-c][1,4]benzodiazepine (PBD) monomers and dimers with DNA," J. Electroanal. Chem. (2006) 593(1-2):241-246.
Marks et al., "By-passing Immunization, Human Antibodies from V-gene Libraries Displayed on Phage," (1991) J. Mol. Biol., 222:581-597.
Martin, C. et al., "Sequence-selective interaction of the minor-groove interstrand cross-linking agent SJG-136 with naked and cellular DNA: footprinting and enzyme inhibition studies," Biochem. (2005) 44(11):4135-4147.
Mastroberardino et al., "Amino-acid transport by heterodimers of 4F2hc/CD98 and members of a permease family," Nature 395 (6699):288-291 (1998).
Mavromatis & Cheson, "Novel therapies for chronic lymphocytic leukemia." Blood Rev. Jun. 2004; 18(2):137-48.
McDonagh, "Engineered antibody-drug conjugates with defined sites and stoichiometries of drug attachment," (2006) Protein Eng. Design & Sel. 19(7): 299-307.
Mendoza et al., "Inhibition of Ligand-mediated HER2 Activation in Androgen-independent Prostate Cancer," (2002) Cancer Res. 62:5485-5488.
Micallef et al., "Epratuzumab with rituximab, cyclophosphamide, doxorubicin, vincristine, and prednisone chemotherapy in patients with previously untreated diffuse large B-cell lymphoma." Blood. Oct. 13, 2011; 118(15):4053-61.
Miller et al., "Design, Construction, and In Vitro Analyses of Multivalent Antibodies," (2003) Jour. of Immunology 170:4854-4861.
Miller et al., "IRTAs: a new family of immunoglobulinlike receptors differentially expressed in B cells," Blood 99 (8):2662-2669 (2002).
Miura et al., "Molecular cloning of a human RP105 homologue and chromosomal localization of the mouse and human RP105 genes (Ly64 and LY64)." Genomics. Dec. 15, 1996; 38(3):299-304.
Miura et al., "RPIOS Is Associated With MD-1 and Transmits an Activation Signal in Human B Cells," (1998) Blood 92:2815-2822.

(56) References Cited

OTHER PUBLICATIONS

Moore M., et al., "Molecular cloning of the eDNA encoding the Epstein-Barr virus/C3d receptor (complement receptor type 2) of human B lymphocytes," Proc. Natl. Acad. Sci. U.S.A. 84, 9194-9198, 1987.
Mori, M. et al., "Total syntheses of prothracarcin and tomaymycin by use of palladium catalyzed carbonylation," Tetrahedron (1986) 42(14):3793-3806.
Morrison et al., "Chimeric human antibody molecules: Mouse antigen-binding domains with human constant region domains," (1984) Proc. Natl. Acad. Sci. USA, 81:6851-6855.
Mountzouris, J.A. et al., "Comparison of a DSB-120 DNA interstrand cross-linked adduct with the corresponding bis-Tomamycin adduct," J. Med. Chem. (1994) 37:3132-3140.
Muller et al., "Cloning and sequencing of the eDNA encoding the human homologue of the murine immunoglobulin-associated protein B29," (1992) Eur. J. Immunol. 22 (6): 1621-1625.
Mungall A.J., et al., "The DNA sequence and analysis of human chromosome 6," Nature 425, 805-811, 2003.
Nagasaka, T. et al., "Stereoselective Synthesis of Tilivalline," Tetrahedron Letters, 30:14, 1871-1872 (1989).
Nagase T., et al., "Prediction of the Coding Sequences of Unidentified Human Genes. XVII. The Complete Sequences of 100 New eDNA Clones from Brain Which Code for Large Proteins in vitro," (2000) DNA Res. 7 (2):143-150.
Nakamuta M., et al., "Cloning and Sequence Analysis of a cDNA Encoding Human Non-Selective Type of Endothelin Receptor," Biochem. Biophys. Res. Commun. 177, 34-39, 1991.
Nakayama et al., "Altered Gene Expression upon BCR Cross-Linking in Burkitt's Lymphoma B Cell Line," (2000) Biochem. Biophys. Res. Commun. 277(1):124-127.
Narayanaswamy, M., "A novel HPLC/MS assay to measure DNA interstrand cross-linking efficacy in oligonucleotides of varying sequence," EJC Supplements (Nov. 2006) 4(12):92-93.
Narayanaswamy, M., "An assay combining high-performance liquid chromatography and mass spectrometry to measure DNA interstrand cross-linking efficiency in oligonucleotides of varying sequences," Anal. Biochem. (2008) 374(1):173-181.
Narayanaswamy, M., "Use of HPLC-MS to characterize novel mono and intrastrand cross-linked DNA adducts formed by the sequence-selective DNA-interactive agent SJG-136," Proceedings of the American Association for Cancer Research Annual Meeting (Apr. 2007) 48:760-761.
Narukawa, Y., "General and efficient synthesis of 2-alkylcarbapenems synthesis of dethia carba analogs of clinically useful carbapenems via palladium-catalyzed cross-coupling reaction," Tetrahedron (1997) 53:539-556.
Naruse et al., "The HLA-DOB gene displays limited polymorphism with only one amino acid substitution," (2002) Tissue Antigens 59:512-519.
Neuberger and Williams, "The intron requirement for immunoglobulin gene expression is dependent upon the promoter," (1988) Nucleic Acids Res. 16:6713-6724.
Nicolaou et al., "Calicheamicin θ: A Rationally Designed Molecule with Extremely Potent and Selective DNA Cleaving Properties and Apoptosis Inducing Activity," Angew Chem. Intl. Ed. Engl. (1994) 33:183-186.
Nilius et al., "Voltage Dependence of the Ca2+-activated Cation Channel TRPM4," The Journal of Biological Chemistry, vol. 278, No. 33, Issue of Aug. 15, pp. 30813-30820, 2003.
Nitschke, "The role of CD22 and other inhibitory co-receptors in B-cell activation." Curr Opin Immunol. Jun. 2005;17(3):290-7.
O'Neil, Chemical Abstract No. 171573p, "The synthesis of Functionalized Pyrrolo-[2,1-c][1,4]-Benzodiazepines", Chemical Abstracts, vol. 126, No. 13, 618 (1997).
O'Neil, I.A., et al., "The Synthesis of Functionalized Pyrrolo-[2,1-c][1,4]-Benzodiazepines," Synlett, 75-78 (1997).
Ogawa Y., et al., "Molecular cloning of a non-isopeptide-selective human endothelin receptor," Biochem. Biophys. Res. Commun. 178, 248-255, 1991.
Okamoto Y., et al. "Palmitoylation of Human Endothelin B," Biol. Chem. 272, 21589-21596, 1997.
O'Neil, I.A. et al., "DPPE: A Convenient Replacement for Triphenylphosphine in the Staudinger and Mitsunobu Reactions", Tetrahedron Letters, vol. 39, No. 42, 7787-7790 (1998).
Pardoll, "The blockade of immune checkpoints in cancer immunotherapy." Nat Rev Cancer. Mar. 22, 2012;12(4):252-64.
Parrish-Novak J., et al., "Interleukins 19, 20, and 24 Signal through Two Distinct Receptor Complexes," J. Biol. Chem. 277, 47517-47523, 2002.
Paul, Fundamental Immunology, 3rd Edition, pp. 292-295.
Payne, G. "Progress in immunoconjugate cancer therapeutics," (2003) Cancer Cell 3:207-212.
Peggs et al., "Cancer immunotherapy: co-stimulatory agonists and co-inhibitory antagonists." Clinical and Experimental Immunology 2009, 157: 9-19.
Pepper, C., "Fludarabine-mediated suppression of the excision repair enzyme ERCC1 contributes to the cytotoxic synergy with the DNA minor groove crosslinking agent SJG-136 (NSC 694501) in chronic lymphocytic leukaemia cells," Br. J. Cancer (2007) 97(2):253-259.
Pepper, C.J. et al., "The novel sequence-specific DNA cross-linking agent SJG-136 (NSC 694501) has potent and selective in vitro cytotoxicity in human B-cell chronic lymphocytic leukemia cells with evidence of a p53-independent mechanism of cell kill," Cancer Res. (2004) 64:6750-6755.
Pezzuto et al., "CD19 Monoclonal Antibody HD37 Inhibits Anti-Immunoglobulin-Induced B Cell Activation and Proliferation." The Journal of Immunology May 1, 1987, 138(9): 2793-2799.
Phillips et al., "Targeting HER2-Positive Breast Cancer with Trastuzumab-DM1, an Antibody-Cytotoxic Drug Conjugate," (2008) Cancer Res. 68(22):9280-9290.
Pingault V., et al., "SOX10 mutations in chronic intestinal pseudo-obstruction suggest a complex physiopathological mechanism," (2002) Hum. Genet. 111, 198-206.
Pletnev S., et al., "Characterization of the Recombinant Extracellular Domains of Human Interleukin-20 Receptors and Their Complexe with Interleukin-19 and Interleukin-20," (2003) Biochemistry 42:12617-12624.
Porkaa et al., "Cloning and Characterization of a Novel Six-Transmembrane Protein STEAP2, Expressed in Normal and Malignant Prostate," Lab. Invest. 82 (11):1573-1582 (2002).
Prasad et al., "Human LAT1, a Subunit of System L Amino Acid Transporter: Molecular Cloning and Transport Function," Biochem. Biophys. Res. Commun. 255 (2), 283-288 (1999).
Preud'Homme et al., "Structure and expression of the mb-1 transcript in human lymphoid cells," (1992) Clin. Exp. Immunol. 90(1):141-146.
Puffenberger E.G., et al., "A Missense Mutation of the Endothelin-B Receptor Gene in Multigenic Hirschsprung's Disease," Cell 79, 1257-1266, 1994.
Puzanov, I., "Phase I and pharmacokinetic trial of SJG-136 administered on a daily x5 schedule," EJC Supplements (Nov. 2006) 4(12):93.
Quintas-Cardama, A., "Sequencing of subcloned PCR products facilitates earlier detetction of BCR-ABL1 and other mutants compared to direct sequencing of the ABL1 kinase domain," Leukemia (2008) 22(4):877-878.
Rahman et al. "Antistaphylococcal activity of DNA-interactive pyrrolobenzodiazepine (PBD) dimers and PBD-biaryl conjugates." J Antimicrob Chemother. Jul. 2012; 67(7):1683-96.
Rahman, K.M., "Effect of microwave irradiation on covalent ligand-DNA interactions," Chem. Commun. (Cambridge, UK), Apr. 2009, 20:2875-2877.
Rahman, K.M., "Rules of DNA adduct formation for pyrrolobenzodiazepine (PBD) dimers," Proceedings of the American Association for Cancer Research Annual Meeting (Apr. 2010) 51:851.
Rahman, K.M., "The pyrrolobenzodiazepine dimer SJG-136 forms sequence-dependent intrastrand DNA cross-lins and monoalkylated adducts in addition to interstrand cross-links," J. Am. Chem. Soc., Sep. 2009, 131(38):13756-13766.

(56) References Cited

OTHER PUBLICATIONS

Rajaiya et al., "Induction of immunoglobulin heavy-chain transcription through the transcription factor Bright requires TFII-I." Mol. Cell. Biol. 26: 4758-4768(2006.

Rao et al., "Influence of diet on mammary cancer in transgenic mice bearing an oncogene expressed in mammary tissue," (1997) Breast Cancer Res. and Treatment 45:149-158.

Reid, J.M., "LC-MS/MS assay and rat pharmacokinetics and metabolism of the dimeric pyrrolobenzodiazepine SJG-136," Proceedings of the American Association for Cancer Research Annual Meeting (Mar. 2004) 45:1248.

Reiter R.E., et al., "Prostate stem cell antigen: A cell surface marker overexpressed in prostate cancer," Proc. Natl. Acad. Sci. U.S.A. 95, 1735-1740, 1998.

Remmers et al., "Conformations of complexes between pyrrolo[1,4]benzodiazepines and DNA segments," J Med Chem. Dec. 1986;29(12):2492-2503.

Rich, I.N., "Validation and development of a predictive paradigm for hemotoxicology using a multifunctional bioluminescence colony-forming proliferation assay," Toxicological Sci. (2005) 87(2):427-441.

Rodrigues et al., "Synthesis and beta-lactamase-mediated activation of a cephalosporin-taxol prodrug," (1995) Chemistry Biology 2:223-227.

Rodriguez et al., "Tyrosine residues in phospholipase Cgamma 2 essential for the enzyme function in B-cell signaling." J Biol Chem. Dec. 21, 2001;276(51):47982-92.

Ross et al., "Prostate Stem Cell Antigen as Therapy Target: Tissue Expression and in Vivo Efficacy of an Immunoconjugate," (2002) Cancer Res. 62:2546-2553.

Rudikoff et al., Single amino acid substitution altering antigen-binding specificity. Proc Natl Acad Sci U S A. Mar. 1982; 79(6):1979-83.

Sagnou, M.J. et al., "Design and Synthesis of Novel Pyrrolobenzodiazepine (PDB) Prodrugs for ADEPT and GDEPT," Bioorganic & Medicinal Chemistry Letters, 10, 2083-2086 (2000).

Sakaguchi et al., "8 lymphocyte lineage-restricted expression of mb-1, a gene with CD3-like structural properties," (1988) EMBO J. 7(11):3457-3464.

Sakamoto A, Yanagisawa M., et al., "Cloning and functional expression of human cDNA for the ETB endothelin receptor," Biochem. Biophys. Res. Commun. 178, 656-663, 1991.

Sanderson et al., "In vivo Drug-Linker Stability of an Anti-CD30 Dipeptide-Linked Auristatin Immunoconjugate," (2005) Clin. Cancer Res. 11:843-852.

Scholler et al., "Soluble member(s) of the mesothelin/ megakaryocyte potentiating factor family are detectable in sera from patients with ovarian carcinoma," Proc. Natl. Acad. Sci. USA vol. 96, pp. 11531-11536, Sep. 1999.

Schroder and Lubke, The Peptides, vol. 1. pp. 76-136 (1965) Academic Press.

Schweikart, K., "In vitro myelosuppression of SJG-136, a pyrrolobenzodiazepine dimer: comparison to bizelesin," Proceedings of the American Association for Cancer Research Annual Meeting (Mar. 2004) 45:486.

Segawa et al., "Growth-related Renal Type II Na/Pi Cotransporter," The Journal of Biolocjcal Chemistry, vol. 277. No. 22, Issue of May 31, pp. 19665-19672, 2002.

Semba K., et al., "A v-erbB-related protooncogene, c-erbB-2, is distinct from the c-erbB-1 /epidermal growth factor-receptor gene and is amplified in a human salivary gland adenocarcinoma," 15 Proc. Natl. Acad. Sci. U.S.A 82, 6497-6501, 1985.

Servenius et al., "Class II Genes of the Human Major Histocompatibility Complex, THE DOBeta Gene is a Divergent Member of the Class II P Gene Family," (1987) J. Biol. Chem. 262:8759-8766.

Shamis et al., "Bioactivation of Self-Immolative Dendritic Prodrugs by Catalytic Antibody 38C2," (2004) J. Am. Chem. Soc. 126:1726-1731.

Sharkey et al., "Epratuzumab-SN-38: A new Antibody-Drug Conjugate for the Therapy of Hematologic Malignancies." Mol Cancer Ther 2012, 11:224-34.

Sheikh F., et al., "Cutting Edge: IL-26 Signals through a Novel Receptor Complex Composed of IL-20 Receptor 1 and IL-10 Receptor 21," (2004) J.Immunol, 172, 2006-2010.

Shen et al., "Conjugation site modulates the in vivo stability and therapeutic activity of antibody-drug conjugates," (2012) Nature Biotech., 30(2):184-191.

Shimizu, K et al., "Prothracarcin, a Novel Antitumor Antibiotic," J. Antibiotics, 35, 972-978 (1982).

Sinha S.K., et al., "Characterization of the EBV /C3d Receptor on the Human Jurkat T Cell Line: Evidence for a Novel Transcript," (1993) J. Immunol. 150, 5311-5320.

Smellie, M. et al., "Cellular pharmacology of novel C8-linked anthramycin-based sequence-selective DNA minor groove cross-linking agents," Br. J. Cancer (1994) 70:48-53.

Smellie, M. et al., "Sequence selective recognition of duplex DNA through covalent interstrand cross-linking," Biochem. (2003) 42:8232-8239.

Smith, P. K. et al., "Measurement of protein using bicinchoninic acid." Anal Biochem. Oct. 1985; 150(1):76-85.

Souillac, P. et al., "Characterization of delivery systems, differential scanning calorimetry," Encyclopedia of Controlled Drug Delivery (1999) 212-227 (pp. 217-218).

Steinfeld et al. "Epratuzumab (humanised anti-CD22 antibody) in primary Sjögren's syndrome: an open-label phase I/II study." Arthritis Res Ther. 2006; 8(4):R129.

Stimmel et al., "Site-specific conjugation on serine right-arrow cysteine variant monoclonal antibodies." J Biol Chem. Sep. 29, 2000; 275(39):30445-50.

Storm et al., "Effect of Small Changes in Orientation on Reaction Rate," (1972) J. Amer. Chem. Soc. 94:5815-5825.

Strausberg et al., "Generation and initial analysis of more than 15,000 full-length human and mouse Edna sequences," (2002) Proc. Natl. Acad. Sci USA 99:16899-16903.

Strop et al., "Location matters: site of conjugation modulates stability and pharmacokinetics of antibody drug conjugates." Chem Biol. Feb. 21, 2013; 20(2):161-7.

Study tudy of Epratuzumab versus Placebo in Subjects with Moderate to Severe General Systemic Lupus Erythematosus (EMBODY 1), [online] ClinicalTrials Identifier: NCT01262365, 2015 [Retrieved Aug. 27, 2019] Retrieved from the internet <URL: https://clinicaltrials.gov/ct2/show/NCT01262365?term=NCT01262365&draw=2&rank=1>.

Suggitt, M., "The hollow fibre model-facilitating anti-cancer preclinical pharmacodynamics and improving animal welfare," Int. J. Oncol. (2006) 29(6):1493-1499.

Suggs, J.W. et al., "Synthesis and structure of anthramycin analogs via hydride reduction of dilactams," Tetrahedron Letters, 26, No. 40, 4871-4874 (1985).

Sukumar et al., "Characterization of MK-4166, a Clinical Agonistic." Cancer Res. Aug. 15, 2017; 77(16).

Sun et al., "Enabling ScFvs as Multi-Drug Carriers: A Dendritic Approach," (2003) Bioorganic & Medicinal Chemistry 11:1761-1768.

Sun et al., "Syntheses of Dendritic Linkers Containing Chlorambucil Residues for the Preparation of Antibody-Multidrug Immunoconjugates," (2002) Bioorganic & Medicinal Chemistry Letters 12:2213-2215.

Sutherland, M.S.K. et al., "SGN-CD33A: a novel CD33-directed antibody-drug conjugate, utilizing pyrrolobenzodiazepine dimers, demonstrates preclinical anti-tumor activity against multi-drug resistant human AML," American Society of Hematology (Dec. 8-12, 2012) Atlanta, Georgia, Abstract No. 3589.

Svensson P.J., et al., "Phenotypic variation in a family with mutations in two Hirschsprung-related genes (RET and endothelin receptor B)," Hum. Genet. 103, 145-148, 1998.

Swiercz J.M., et al., "Plexin-81 /RhoGEF-mediated Rho A activation involves the receptor tyrosine kinase ErbB-2," J. Cell Biol. 165, 869-880, 2004.

(56) References Cited

OTHER PUBLICATIONS

Syrigos and Epenetos, "Antibody Directed Enzyme Prodrug Therapy (ADEPT): A Review of the Experimental and Clinical Considerations," (1999) Anticancer Research 19:605-614.
Takeuchi, T. et al., "Neothramycins A and B, New Antitumor Antibiotics," J. Antibiotics, 29, 93-96 (1976).
Taskin et al., "High efficacy and safety profile of fractionated doses of Mylotarg as induction therapy in patients with relapsed acute myeloblastic leukemia: a prospective study of the alfa group." Leukemia. Jan. 2007;21(1):66-71.
Tawaragi Y., et al., "Primary structure of nonspecific crossreacting antigen (NCA), a member of carcinoembryonic antigen (CEA) gene family, deduced from cDNA sequence," Biochem. Biophys. Res. Commun. 150, 89-96, 1988.
Tedder et al., "The CD19/CD21 signal transduction complex of B lymphocytes." Immunol Today. Sep. 1994;15(9):437-42.
Tercel, M. et al., "Unsymmetrical DNA cross-linking agents: combination of the CBI and PBD pharmacophores," J. Med. Chem. (2003) 46:2132-2151.
Thompson J.S., et al., "BAFF-R, a Newly Identified TNF Receptor That Specifically Interacts with BAFF," Science 293 (5537), 2108-2111 (2001).
Thurston, D. E., "Advances in the study of Pyrrolo[2,1-c][1,4] benzodiazepine (PBD) Antitumour Antibiotics", Molecular Aspects of Anticancer Drug-DNA Interaction, Neidle, S. and Waring, M.J., Eds.; Macmillan Press Ltd, 1:54-88 (1993).
Thurston, D.E. and Bose, D.S., "Synthesis of DNA-Interactive Pyrrolo[2,1-c][1,4]benzodiazepines," Chem. Rev., 94:433-465 (1994).
Thurston, D.E. and Thompson, A.S., "The molecular recognition of DNA," Chem. Brit., 26, 767-772 (1990).
Thurston, D.E et al., "Effect of A-ring modifications on the DNA-binding behavior and cytotoxicity of pyrrolo[2,1-c][1,4]benzodiazepines", Journal of Medicinal Chemistry, 42:1951-1964 (1999).
Thurston, D.E. et al., "Synthesis of Sequence-selective C8-linked Pyrrolo [2,1-c][1,4]-Benzodiazepine DNA Interstrand Cross-linking Agent," J. Org. Chem., 61:8141-8147 (1996).
Thurston, D.E. et al., "Synthesis of a novel GC-specific covalent-binding DNA affinity-cleavage agent based on pyrrolobenzodiazepines (PBDs)," Chemical Communications, 563-565 (1996).
Thurston, D.E., "Nucleic acid targeting: therapeutic strategies for the 21st century," Brit. J. Cancer (1999) 80(1):65-85.
Tiberghien, A.C. et al., "Application of the stille coupling reaction to the synthesis of C2-substituted endo-exo unsaturated pyrrolo[2,1-c][1,4]benzodiazepines (PBDs)," Biorg. Med. Chem. Lett. (2004) 14:5041-5044.
Tiberghien, A.C., "Application of the stille coupling reaction to the synthesis of C2- substituted endo-exo unsaturated pyrrolo[2,1-c][1,4]benzodiazepines (PBDs)," Bioorg. Med. Chem. Lett. (2008) 18(6):2073-2077.
Tigue et al., "MEDI1873, a potent, stabilized hexameric agonist of human GITR with regulatory T-cell targeting potential." Oncoimmunology 2017; 6(3):e1280645.
Toki et al., "Protease-Mediated Fragmentation of p-Amidobenzyl Ethers: A New Strategy for the Activation of Anticancer Prodrugs," (2002) J. Org. Chem. 67:1866-1872.
Tonnelle et al., "DO Beta a new chain gene in HLA-D with a distinct regulation of expression," (1985) EMBO J. 4(11):2839-2847.
Touchman et al., "The Genomic Region Encompassing the Nephropathic Cystinosis Gene (CTNS): Complete Sequencing of a 200-kb Segment and Discovery of a Novel Gene within the Common Cystinosis-Causing Deletion," (2000) Genome Res. 10:165-173.
Tozuka et al., "Studies on tomaymycin. II. Total synthesis of the antitumor antibiotics, E-and Z-tomaymycins," J. Antibiotics (Tokyo) (1983) 36:276-282.
Trail et al., "Monoclonal antibody drug immunoconjugates for targeted treatment of cancer," (2003) Cancer Immunol. Immunother. 52:328-337.
Tsunakawa, M. et al., "Porothramycin, a new antibiotic of the anthramycin group: Production, isolation, structure and biological activity," J. Antibiotics, 41:1366-1373 (1988).
Tsutsumi M., et al., "Novel endothelin B receptor transcripts with the potential of generating a new receptor," Gene 228, 43-49, 1999.
Uchida et al., "A Novel Epidermal Growth Factor-like Molecule Containing Two Follistatin Modules Stimulates Tyrosine Phosphorylation of erbB-4 in MKN28 Gastric Cancer Cells," (1999) Biochem. Biophys. Res. Commun. 266:593-602.
Umezawa, H. et al., "Mazethramycins," SciFinder Scholar, 2-3 (2002).
Umezawa, H. et al., Chemical Abstract No. 4427a, "Mazethramycins" Chemical Abstracts, vol. 90, No. 1, 428 (1979).
Uniprot/Swiss-Prot accession No. P15391.
Uniprot/Swiss-Prot accession No. P16410.3 (2019).
Uniprot/Swiss-Prot accession No. P43489.1 (2019).
Uniprot/Swiss-Prot accession No. Q06187.3 (2020).
Uniprot/Swiss-Prot accession No. Q15116.3 (2019).
Uniprot/Swiss-Prot accession No. Q9NZQ7.1 (2019).
Uniprot/Swiss-Prot accession No. Q9Y5U5 (2019).
Verheij J.B., et al., "ABCD Syndrome Is Caused by a Homozygous Mutation in the EDNRB Gene," Am. J. Med. 15 Genet. 108, 223-225, 2002.
Vippagunta, S.R. et al., "Crystalline solids," Adv. Drug Delivery Rev. (2001) 48:3-26.
Von Hoegen et al., "Identification of a human protein homologous to the mouse Lyb-2 B cell differentiation antigen and sequence of the corresponding cDNA," (1990) J. Immunol. 144(12):4870-4877.
Wallace & Goldenberg, "Epratuzumab for systemic lupus erythematosus." Lupus. Apr. 2013; 22(4):400-5.
Wallace et al., "Efficacy and safety of epratuzumab in patients with moderate/severe flaring systemic lupus erythematosus: results from two randomized, double-blind, placebo-controlled, multicentre studies (Alleviate) and follow-up." Rheumatology, vol. 52, Issue 7, Jul. 2013, pp. 1313-1322.
Wallace et al., "Efficacy and safety of epratuzumab in patients with moderate/severe active systemic lupus erythematosus: results from EMBLEM, a phase llb, randomised, double-blind, placebo-controlled, multicentre study." Ann Rheum Dis. Jan. 2014;73(1):183-90.
Wang, J.H., "Determination of antitumor agent AJG-136 in human serum by HPLC with tandem mass spectrometric detection (HPLC-MS/MS)," Abstracts of Papers American Chemical Society (Mar. 13, 2005) 229(1):U119.
Webster et al., "Mammary tumorigenesis and metastasis in transgenic mice," (1994) Semin. Cancer Biol. 5:69-76.
Weidner-Wells, M.A. et al., "Photochemical approach to the synthesis of the pyrrolo[1,4]benzodiazepine antibiotics," J. Org. Chem. (1989) 54:5746-5758.
Weinberg et al. "Anti-OX40 (CD134) Administration to Nonhuman Primates: Immunostimulatory Effects andToxicokinetic Study." j. Immunother 2006, 29: 575-585.
Weis J.J., et al., "Identification of a partial eDNA clone for the C3d/Epstein-Barr virus receptor of human B lymphocytes: Homology with the receptor for fragments C3b and C4b of the third and fourth components of complement," Proc. Natl. Acad. Sci. U.S.A. 83, 5639-5643, 1986.
Weis J.J., et al., "Structure of the human b lymphocyte receptor for c3d and the epstein-barr virus and relatedness to other members of the family of c3/c4 binding proteins," J. Exp. Med. 167, 1047-1066, 1988.
Wells, G. et al., "Design, synthesis and biophysical and biological evaluation of a series of pyrrolobenzodiazepine-poly(N-methylpyrrole) conjugates," J. Med. Chem. (2006) 49:5442-5461.
Wikipedia, "How many types of cancer are there?", 2012, 3 pages; http://wiki.answers.com/Q/How-many-different-types_of_cancer_are_there.
Wikipedia, "Management of Cancer," 2012, 1 page; http://en.wikipedia.org/wiki/Management of cancer.
Wilkinson, G.P., "Pharmacokinetics and intracellular pharmacological characteristics of the novel pyrrolobenzodiazepine (PBD) dimer SJG-136," Proceedings of the American Association for Cancer Research Annual Meeting (Jul. 2003) 44:320.

(56) References Cited

OTHER PUBLICATIONS

Wilkinson, G.P., "Pharmacokinetics, metabolism and glutathione reactivity of SJG-136," Br. J. Cancer (2003) 88(Supp. 1): S29.

Wilkinson, G.P., "Preliminary pharmacokinetic and bioanalytical studies of SJG-136 (NSC 694501), a sequence-selective pyrrolobenzodiazepine dimer DNA-cross-linking agent," Investigational New Drugs (2004) 22(3):231-240.

Wilson et al., "eDNA Cloning of the B Cell Membrane Protein CD22: A Mediator of B-B Cell Interactions," (1991) J. Exp. Med. 173:137-146.

Wilson, S.C. et al., "Design and Synthesis of a Novel Epoxide-Containing Pyrrolo[2,1-c][1,4]benzodiazepine (PBD) via a New Cyclization Procedure," Tetrahedron Letters, 36, No. 35, 6333-6336 (1995).

Wilson, S.C. et al., "Design, Synthesis, and Evaluation of a Novel Sequence-Selective Epoxide-Containing DNA Cross-Linking Agent Based on the Pyrrolo[2,1-c][1,4]benzodiazepine System", J. Med. Chem. 42: 4028-4041 (1999).

Wines et al., "The IgG Fc contains distinct Fc receptor (FcR) binding sites: the leukocyte receptors Fc gamma RI and Fc gamma RIIa bind to a region in the Fc distinct from that recognized by neonatal FcR and protein A." J Immunol. May 15, 2000; 164(10):5313-8.

Wolff, M.E., Burger's Medicinal Chemistry, 4th Edition, Part I, Wiley: New York (1979) 336-337.

Wolff, M.E., Burger's Medicinal Chemistry, 5th Edition, Part I, John Wiley & Sons (1995) 975-977.

Workman, P. et al., "United Kingdom Co-ordinating Committee on Cancer Research (UKCCCR) guidelines for the welfare of animals in experimental neoplasia (second edition)," Br. J. Cancer (1998) 77(1):1-10.

Wu et al., "Arming antibodies: prospects and challenges for immunoconjugates," (2005) Nature Biotech. 23(9):1137-1145.

Xie et al., "In vivo behaviour of antibody-drug conjugates for the targeted treatment of cancer," (2006) Expert. Opin Biol. Ther. 6(3):281-291.

Xie, G. et al., "Bisindolylmaleimides linked to DNA minor groove binding lexitropsins: synthesis, inhibitory activity against topoisomerasel, and biological evaluation," J. Med. Chem. (1996) 39:1049-1055.

Xu et al., "Molecular Cloning, Functional Characterization, Tissue Distribution, and Chromosomal Localization of a Human, Small Intestinal Sodium-Phosphate (Na + −Pi) Transporter (SLC34A2)," Genomics 62 (2):281-284 (1999).

Xu, M.J., et al., "Molecular Cloning and Characterization of SPAP1, an Inhibitory Receptor," (2001) Biochem. Biophys. Res. Commun. 280 (3):768-775.

Xu, X.Z., et al., "Regulation of melastatin, a TRP-related protein, through interaction with a cytoplasmic isoform," Proc. Natl. Acad. Sci. U.S.A. 98 (19):10692-10697 (2001).

Yamaguchi, N., et al., "A Novel Cytokine Exhibiting Megakaryocyte Potentiating Activity from a Human Pancreatic Tumor Cell Line HPC-Y5," Biol. Chem. 269 (2), 805-808 (1994).

Yamamoto T., et al., "Similarity of protein encoded by the human c-erb-B-2 gene to epidermal growth factor receptor," Nature 319, 230-234, 1986.

Yang et al., "BAP-135, a target for Bruton's tyrosine kinase in response to B cell receptor engagement." Proc Natl Acad Sci U S A. Jan. 21, 1997;94(2):604-9.

Yang et al., "Murine Six-Transmembrane Epithelial Antigen of the Prostate, Prostate Stem Cell Antigen, and Prostate-specific Membrane Antigen: Prostate-specific Cell-Surface Antigens Highly Expressed in Prostate Cancer of Transgenic Adenocarcinoma Mouse Prostate Mice," Cancer Research, 61, 5857-5860. Aug. 1, 2001.

Yin & Lloyd, "Molecular Cloning of the CA125 Ovarian Cancer Antigen," J. Biol. Chem. 276 (29):27371-27375 (2001).

Younes et al., "Phase I multidose-escalation study of the anti-CD19 maytansinoid immunoconjugate SAR3419 administered by intravenous infusion every 3 weeks to patients with relapsed/refractory B-cell lymphoma," J Clin Oncol., 2012, 30(22):2776-82.

Yu et al., "Human mb-1 Gene: Complete eDNA Sequence and Its Expression in B Cells Bearing Membrane Ig of Various Isotypes," (1992) J. Immunol. 148(2) 633-637.

Zalevsky et al., "Enhanced antibody half-life improves in vivo activity." Nat Biotechnol. Feb. 2010; 28(2):157-9.

Zammarchi et al., "Pre-Clinical Development of Adct-402, a Novel Pyrrolobenzodiazepine (PBD)-Based Antibody Drug Conjugate (ADC) Targeting CD19-Expressing B-Cell Malignancies," Blood, 2015, 126:1564, Abstract.

Celgene (sponsor); ClinicalTrials.gov Identifier: NCT02733042, 2016, A Study to Determine Dose, Safety, and Efficacy of Durvalumab as Monotherapy and in Combination Therapy in Subjects With Lymphoma or Chronic Lymphocytic Leukemia (Fusion NHL 001). [online] Retrieved from the internet <URL:https://clinicaltrials.gov/ct2/show/NCT02733042?term=NCT02733042&rank=1>.

Kahl, et al., A phase 1 dose-escalation study to evaluate the tolerability, safety, pharmacokinetics, and antitumor activity of ADCT-402 in patients with relapsed or refractory B-cell lineage non-Hodgkin lymphoma (B-NHL), Jun. 3-7, 2016, ASCO Annual Meeting.

Hartley, J., "The development of pyrrolobenzodiazepines as antitumor agents", Expert Opin. Investig. Drugs, 20(6) (2011).

Hartley et al., "Preclinical pharmacology and mechanism of action of SG3199, the pyrrolobenzodiazepine (PBD) dimer warhead component of antibody-drug conjugate (ADC) payload tesirine", Scientific Reports 8:10479 (2018); published online: Jul. 11, 2018.

John Hartley, "Antibody-drug conjugates (ADCs) delivering pyrrolobenzodiazepine (PBD) dimers for cancer therapy," Expert Opinion on Biological Therapy, (2020).

Tourneau et al., "Dose Escalation Methods in Phase I Cancer Clinical Trials," J Natl Cancer Inst., 101(10): 708-720 (2009); PMID: 19436029.

Zammarchi et al., "ADCT-402, a PBD dimer-containing antibody drug conjugate targeting CD19-expressing malignancies," Blood, 131(10):1094-1105 (2018); PMID: 29298756.

Wong, et al., "Estimation of clinical trial success rates and related parameters," Biostatistics, 20(2): 273-286 (2019); PMID: 29394327.

Kahl et al., "A Phase I Study of ADCT-402 (Loncastuximab Tesirine), a Novel Pyrrolobenzodiazepine-Based Antibody-Drug Conjugate, in Relapsed/ Refractory B-Cell Non-Hodgkin Lymphoma," Clin Cancer Res., 25 (23):6986-6994 (2019); PMID: 31685491.

Hamadani et al., "Final results of a phase 1 study of loncastuximab tesirine in relapsed/refractory B-cell non-Hodgkin lymphoma," Blood, 137(19):2634-2645 (2021); PMID: 33211842.

Caimi et al., "Loncastuximab tesirine in relapsed or refractory diffuse large B-cell lymphoma (LOTIS-2): a multicentre, open-label, single-arm, phase 2 trial," Lancet Oncol., S1470-2045(21)00139-X (2021).

Kalakonda et al., "Selinexor in patients with relapsed or refractory diffuse large B-cell lymphoma (SADAL): a single-arm, multinational, multicentre, open-label, phase 2 trial," Lancet Haematol., (7):e511-e522 (2020); PMID: 32589977.

Waight et al., "Structural Basis of Microtubule Destabilization by Potent Auristatin Anti-Mitotics," PLoS One, 11(8) (2016), published Aug. 12, 2016.

Yu, et al. Antibody-drug conjugates in clinical trials for lymphoid malignancies and multiple myeloma, J Hematol. Oncol., 12(1):94 (2019).

\* cited by examiner

SEQUENCES

SEQ ID NO. 1 (RB4v1.0 VH):
QVQLVQPGAEVVKPGASVKLSCKTSGYTFTSNWMHWVKQRPGQGLEWIGEIDPSDSYTN
YNQNFKGKAKLTVDKSTSTAYMEVSSLRSDDTAVYYCARGSNPYYYAMDYWGQGTSVTV
S

SEQ ID NO. 2 (RB4v1.2 VH):
QVQLVQPGAEVVKPGASVKLSCKTSGYTFTSNWMHWVKQAPGQGLEWIGEIDPSDSYTN
YNQNFQGKAKLTVDKSTSTAYMEVSSLRSDDTAVYYCARGSNPYYYAMDYWGQGTSVTV
S

SEQ ID NO. 3 (B43 VH):
QVQLLESGAELVRPGSSVKISCKASGYAFSSYWMNWVKQRPGQGLEWIGQIWPGDGDTN
YNGKFKGKATLTADESSSTAYMQLSSLRSEDSAVYSCARRETTTVGRYYYAMDYWGQGT
TVT

SEQ ID NO. 4 (HD37 VH):
QVQLQQSGAELVRPGSSVKISCKASGYAFSSYWMNWVKQRPGQGLEWIGQIWPGDGDT
NYNGKFKGKATLTADESSSTAYMQLSSLASEDSAVYFCARRETTTVGRYYYAMDYWGQG
TSVTVS

SEQ ID NO. 5 (4G7 VH):
EVQLQQSGPELIKPGASVKMSCKASGYTFTSYVMHWVKQKPGQGLEWIGYINPYNDGTKY
NEKFKGKATLTSDKSSSTAYMELSSLTSEDSAVYYCARGTYYYGSRVFDYWGQGTTLTVS

SEQ ID NO. 6 (FMC63 VH):
EVKLQESGPGLVAPSQSLSVTCTVSGVSLPDYGVSWIRQPPRKGLEWLGVIWGSETTYYN
SALKSRLTIIKDNSKSQVFLKMNSLQTDDTAIYYCAKHYYYGGSYAMDYWGQGTSVTVS

SEQ ID NO.7 (RB4v1.0 VK):
EIVLTQSPAIMSASPGERVTMTCSASSGVNYMHWYQQKPGTSPRRWIYDTSKLASGVPAR
FSGSGSGTSYSLTISSMEPEDAATYYCHQRGSYTFGGGTKLEIK

Figure 1A

SEQ ID NO. 8 (RB4v1.2 VK):
EIVLTQSPAIMSASPGERVTMTCSASSGVNYMHWYQQKPGTSPRRWIYDTSKLASGVPAR
FSGSGSGTSYSLTISSMEPEDAATYYCHQRGSYTFGGGTKLEIK

SEQ ID NO. 9 (B43 VK):
ELVLTQSPASLAVSLGQRATISCKASQSVDYDGDSYLNWYQQIPGQPPKLLIYDASNLVSGI
PPRFSGSGSGTDFTLNIHPVEKVDAATYHCQQSTEDPWTFGGGTKLEIK

SEQ ID NO. 10 (HD37 VK):
DILLTQTPASLAVSLGQRATISCKASQSVDYDGDSYLNWYQQIPGQPPKLLIYDASNLVSGIP
PRFSGSGSGTDFTLNIHPVEKVDAATYHCQQSTEDPWTFGGGTKLEIK

SEQ ID NO. 11 (4G7 VK):
DIVMTQAAPSIPVTPGESVSISCRSSKSLLNSNGNTYLYWFLQRPGQSPQLLIYRMSNLASG
VPDRFSGSGSGTAFTLRISRVEAEDVGVYYCMQHLEYPFTFGAGTKLELK

SEQ ID NO. 12 (FMC63 VK):
DIQMTQTTSSLSASLGDRVTISCRASQDISKYLNWYQQKPDGTVKLLIYHTSRLHSGVPSRF
SGSGSGTDYSLTISNLEQEDIATYFCQQGNTLPYTFGGGTKLEIT

SEQ ID NO. 13 (RB4v1.2-HC):
QVQLVQPGAEVVKPGASVKLSCKTSGYTFTSNWMHWVKQAPGQGLEWIGEIDPSDSYTN
YNQNFQGKAKLTVDKSTSTAYMEVSSLRSDDTAVYYCARGSNPYYYAMDYWGQGTSVTV
SSASTKGPSVFPLAPSSKSTSGGTAALGCLVKDYFPEPVTVSWNSGALTSGVHTFPAVLQS
SGLYSLSSVVTVPSSSLGTQTYICNVNHKPSNTKVDKKVEPKSCDKTHTCPPCPAPELLGG
PSVFLFPPKPKDTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRWQQ
GNVFSCSVMHEALHNHYTQKSLSLSPG

SEQ ID NO. 14 (RB4v1.2-LC):
EIVLTQSPAIMSASPGERVTMTCSASSGVNYMHWYQQKPGTSPRRWIYDTSKLASGVPAR
FSGSGSGTSYSLTISSMEPEDAATYYCHQRGSYTFGGGTKLEIKRTVAAPSVFIFPPSDEQL
KSGTASVVCLLNNFYPREAKVQWKVDNALQSGNSQESVTEQDSKDSTYSLSSTLTLSKAD
YEKHKVYACEVTHQGLSSPVTKSFNRGEC

Figure 1B

SEQUENCE LISTING

```
<160> NUMBER OF SEQ ID NOS: 18

<210> SEQ ID NO 1
<211> LENGTH: 119
<212> TYPE: PRT
<213> ORGANISM: Artificial Sequence
<220> FEATURE:
<223> OTHER INFORMATION: RB4v1.0 VH

<400> SEQUENCE: 1

Gln Val Gln Leu Val Gln Pro Gly Ala Glu Val Val Lys Pro Gly Ala
1               5                   10                  15

Ser Val Lys Leu Ser Cys Lys Thr Ser Gly Tyr Thr Phe Thr Ser Asn
            20                  25                  30

Trp Met His Trp Val Lys Gln Arg Pro Gly Gln Gly Leu Glu Trp Ile
        35                  40                  45

Gly Glu Ile Asp Pro Ser Asp Ser Tyr Thr Asn Tyr Asn Gln Asn Phe
    50                  55                  60

Lys Gly Lys Ala Lys Leu Thr Val Asp Lys Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Arg Gly Ser Asn Pro Tyr Tyr Ala Met Asp Tyr Trp Gly Gln
            100                 105                 110

Gly Thr Ser Val Thr Val Ser
        115

<210> SEQ ID NO 2
<211> LENGTH: 119
<212> TYPE: PRT
<213> ORGANISM: Artificial Sequence
```

```
<220> FEATURE:
<223> OTHER INFORMATION: RB4v1.2 VH

<400> SEQUENCE: 2

Gln Val Gln Leu Val Gln Pro Gly Ala Glu Val Val Lys Pro Gly Ala
1               5                   10                  15

Ser Val Lys Leu Ser Cys Lys Thr Ser Gly Tyr Thr Phe Thr Ser Asn
            20                  25                  30

Trp Met His Trp Val Lys Gln Ala Pro Gly Gln Gly Leu Glu Trp Ile
        35                  40                  45

Gly Glu Ile Asp Pro Ser Asp Ser Tyr Thr Asn Tyr Asn Gln Asn Phe
    50                  55                  60

Gln Gly Lys Ala Lys Leu Thr Val Asp Lys Ser Ser Thr Ala Tyr
65                  70                  75                  80

Met Glu Val Ser Ser Leu Arg Ser Asp Asp Thr Ala Val Tyr Tyr Cys
                85                  90                  95

Ala Arg Gly Ser Asn Pro Tyr Tyr Tyr Ala Met Asp Tyr Trp Gly Gln
            100                 105                 110

Gly Thr Ser Val Thr Val Ser
        115

<210> SEQ ID NO 3
<211> LENGTH: 121
<212> TYPE: PRT
<213> ORGANISM: Artificial Sequence
<220> FEATURE:
<223> OTHER INFORMATION: B43 VH

<400> SEQUENCE: 3

Gln Val Gln Leu Leu Glu Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Thr Ala Tyr
65                  70                  75                  80

Met Gln Leu Ser Ser Leu Arg Ser Glu Asp Ser Ala Val Tyr Ser Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr
        115                 120

<210> SEQ ID NO 4
<211> LENGTH: 123
<212> TYPE: PRT
<213> ORGANISM: Artificial Sequence
<220> FEATURE:
<223> OTHER INFORMATION: HD37 VH

<400> SEQUENCE: 4

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30
```

```
Trp Met Asn Trp Val Lys Gln Arg Pro Gly Gln Gly Leu Glu Trp Ile
         35                  40                  45

Gly Gln Ile Trp Pro Gly Asp Gly Asp Thr Asn Tyr Asn Gly Lys Phe
 50                      55                  60

Lys Gly Lys Ala Thr Leu Thr Ala Asp Glu Ser Ser Ser Thr Ala Tyr
 65                  70                  75                  80

Met Gln Leu Ser Ser Leu Ala Ser Glu Asp Ser Ala Val Tyr Phe Cys
                 85                  90                  95

Ala Arg Arg Glu Thr Thr Thr Val Gly Arg Tyr Tyr Ala Met Asp
                100                 105                 110

Tyr Trp Gly Gln Gly Thr Ser Val Thr Val Ser
        115                 120

<210> SEQ ID NO 5
<211> LENGTH: 120
<212> TYPE: PRT
<213> ORGANISM: Artificial Sequence
<220> FEATURE:
<223> OTHER INFORMATION: 4G7 VH

<400> SEQUENCE: 5

Glu Val Gln Leu Gln Gln Ser Gly Pro Glu Leu Ile Lys Pro Gly Ala
1                5                  10                  15

Ser Val Lys Met Ser Cys Lys Ala Ser Gly Tyr Thr Phe Thr Ser Tyr
                 20                  25                  30

Val Met His Trp Val Lys Gln Lys Pro Gly Gln Gly Leu Glu Trp Ile
         35                  40                  45

Gly Tyr Ile Asn Pro Tyr Asn Asp Gly Thr Lys Tyr Asn Glu Lys Phe
 50                      55                  60

Lys Gly Lys Ala Thr Leu Thr Ser Asp Lys Ser Ser Ser Thr Ala Tyr
 65                  70                  75                  80

Met Glu Leu Ser Ser Leu Thr Ser Glu Asp Ser Ala Val Tyr Tyr Cys
                 85                  90                  95

Ala Arg Gly Thr Tyr Tyr Tyr Gly Ser Arg Val Phe Asp Tyr Trp Gly
                100                 105                 110

Gln Gly Thr Thr Leu Thr Val Ser
        115                 120

<210> SEQ ID NO 6
<211> LENGTH: 119
<212> TYPE: PRT
<213> ORGANISM: Artificial Sequence
<220> FEATURE:
<223> OTHER INFORMATION: FMC63 VH

<400> SEQUENCE: 6

Glu Val Lys Leu Gln Glu Ser Gly Pro Gly Leu Val Ala Pro Ser Gln
1                5                  10                  15

Ser Leu Ser Val Thr Cys Thr Val Ser Gly Val Ser Leu Pro Asp Tyr
                 20                  25                  30

Gly Val Ser Trp Ile Arg Gln Pro Pro Arg Lys Gly Leu Glu Trp Leu
         35                  40                  45

Gly Val Ile Trp Gly Ser Glu Thr Thr Tyr Tyr Asn Ser Ala Leu Lys
 50                      55                  60

Ser Arg Leu Thr Ile Ile Lys Asp Asn Ser Lys Ser Gln Val Phe Leu
 65                  70                  75                  80

Lys Met Asn Ser Leu Gln Thr Asp Asp Thr Ala Ile Tyr Tyr Cys Ala
                 85                  90                  95
```

```
Lys His Tyr Tyr Tyr Gly Gly Ser Tyr Ala Met Asp Tyr Trp Gly Gln
            100                 105                 110

Gly Thr Ser Val Thr Val Ser
        115

<210> SEQ ID NO 7
<211> LENGTH: 104
<212> TYPE: PRT
<213> ORGANISM: Artificial Sequence
<220> FEATURE:
<223> OTHER INFORMATION: RB4v1.0 VK

<400> SEQUENCE: 7

Glu Ile Val Leu Thr Gln Ser Pro Ala Ile Met Ser Ala Ser Pro Gly
1               5                   10                  15

Glu Arg Val Thr Met Thr Cys Ser Ala Ser Ser Gly Val Asn Tyr Met
            20                  25                  30

His Trp Tyr Gln Gln Lys Pro Gly Thr Ser Pro Arg Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Pro Glu
65                  70                  75                  80

Asp Ala Ala Thr Tyr Tyr Cys His Gln Arg Gly Ser Tyr Thr Phe Gly
                85                  90                  95

Gly Gly Thr Lys Leu Glu Ile Lys
            100

<210> SEQ ID NO 8
<211> LENGTH: 104
<212> TYPE: PRT
<213> ORGANISM: Artificial Sequence
<220> FEATURE:
<223> OTHER INFORMATION: RB4v1.2 VK

<400> SEQUENCE: 8

Glu Ile Val Leu Thr Gln Ser Pro Ala Ile Met Ser Ala Ser Pro Gly
1               5                   10                  15

Glu Arg Val Thr Met Thr Cys Ser Ala Ser Ser Gly Val Asn Tyr Met
            20                  25                  30

His Trp Tyr Gln Gln Lys Pro Gly Thr Ser Pro Arg Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Pro Glu
65                  70                  75                  80

Asp Ala Ala Thr Tyr Tyr Cys His Gln Arg Gly Ser Tyr Thr Phe Gly
                85                  90                  95

Gly Gly Thr Lys Leu Glu Ile Lys
            100

<210> SEQ ID NO 9
<211> LENGTH: 111
<212> TYPE: PRT
<213> ORGANISM: Artificial Sequence
<220> FEATURE:
<223> OTHER INFORMATION: B43 VK

<400> SEQUENCE: 9
```

Glu Leu Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65              70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys
            100                 105                 110

<210> SEQ ID NO 10
<211> LENGTH: 111
<212> TYPE: PRT
<213> ORGANISM: Artificial Sequence
<220> FEATURE:
<223> OTHER INFORMATION: HD37 VK

<400> SEQUENCE: 10

Asp Ile Leu Leu Thr Gln Thr Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65              70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys
            100                 105                 110

<210> SEQ ID NO 11
<211> LENGTH: 112
<212> TYPE: PRT
<213> ORGANISM: Artificial Sequence
<220> FEATURE:
<223> OTHER INFORMATION: 4G7 VK

<400> SEQUENCE: 11

Asp Ile Val Met Thr Gln Ala Ala Pro Ser Ile Pro Val Thr Pro Gly
1               5                   10                  15

Glu Ser Val Ser Ile Ser Cys Arg Ser Ser Lys Ser Leu Leu Asn Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65              70                  75                  80

Ser Arg Val Glu Ala Glu Asp Val Gly Val Tyr Tyr Cys Met Gln His
                85                  90                  95

```
Leu Glu Tyr Pro Phe Thr Phe Gly Ala Gly Thr Lys Leu Glu Leu Lys
                100                 105                 110
```

<210> SEQ ID NO 12
<211> LENGTH: 107
<212> TYPE: PRT
<213> ORGANISM: Artificial Sequence
<220> FEATURE:
<223> OTHER INFORMATION: FMC63 VK

<400> SEQUENCE: 12

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
                100                 105
```

<210> SEQ ID NO 13
<211> LENGTH: 449
<212> TYPE: PRT
<213> ORGANISM: Artificial Sequence
<220> FEATURE:
<223> OTHER INFORMATION: RB4v1.2-HC

<400> SEQUENCE: 13

```
Gln Val Gln Leu Val Gln Pro Gly Ala Glu Val Val Lys Pro Gly Ala
1               5                   10                  15

Ser Val Lys Leu Ser Cys Lys Thr Ser Gly Tyr Thr Phe Thr Ser Asn
            20                  25                  30

Trp Met His Trp Val Lys Gln Ala Pro Gly Gln Gly Leu Glu Trp Ile
        35                  40                  45

Gly Glu Ile Asp Pro Ser Asp Ser Tyr Thr Asn Tyr Asn Gln Asn Phe
    50                  55                  60

Gln Gly Lys Ala Lys Leu Thr Val Asp Lys Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Arg Gly Ser Asn Pro Tyr Tyr Ala Met Asp Tyr Trp Gly Gln Gly
                100                 105                 110

Gly Thr Ser Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
```

```
                180              185              190
    Ser Ser Ser Leu Gly Thr Gln Thr Tyr Ile Cys Asn Val Asn His Lys
            195                  200                  205

Pro Ser Asn Thr Lys Val Asp Lys Lys Val Glu Pro Lys Ser Cys Asp
        210                  215                  220

Lys Thr His Thr Cys Pro Pro Cys Pro Ala Pro Glu Leu Leu Gly Gly
    225                  230                  235                  240

Pro Ser Val Phe Leu Phe Pro Pro Lys Pro Lys Asp Thr Leu Met Ile
                    245                  250                  255

Ser Arg Thr Pro Glu Val Thr Cys Val Val Val Asp Val Ser His Glu
                260                  265                  270

Asp Pro Glu Val Lys Phe Asn Trp Tyr Val Asp Gly Val Glu Val His
            275                  280                  285

Asn Ala Lys Thr Lys Pro Arg Glu Glu Gln Tyr Asn Ser Thr Tyr Arg
        290                  295                  300

Val Val Ser Val Leu Thr Val Leu His Gln Asp Trp Leu Asn Gly Lys
    305                  310                  315                  320

Glu Tyr Lys Cys Lys Val Ser Asn Lys Ala Leu Pro Ala Pro Ile Glu
                    325                  330                  335

Lys Thr Ile Ser Lys Ala Lys Gly Gln Pro Arg Glu Pro Gln Val Tyr
                340                  345                  350

Thr Leu Pro Pro Ser Arg Glu Glu Met Thr Lys Asn Gln Val Ser Leu
            355                  360                  365

Thr Cys Leu Val Lys Gly Phe Tyr Pro Ser Asp Ile Ala Val Glu Trp
        370                  375                  380

Glu Ser Asn Gly Gln Pro Glu Asn Asn Tyr Lys Thr Thr Pro Pro Val
    385                  390                  395                  400

Leu Asp Ser Asp Gly Ser Phe Phe Leu Tyr Ser Lys Leu Thr Val Asp
                    405                  410                  415

Lys Ser Arg Trp Gln Gln Gly Asn Val Phe Ser Cys Ser Val Met His
                420                  425                  430

Glu Ala Leu His Asn His Tyr Thr Gln Lys Ser Leu Ser Leu Ser Pro
            435                  440                  445

Gly

<210> SEQ ID NO 14
<211> LENGTH: 211
<212> TYPE: PRT
<213> ORGANISM: Artificial Sequence
<220> FEATURE:
<223> OTHER INFORMATION: RB4v1.2-LC

<400> SEQUENCE: 14

Glu Ile Val Leu Thr Gln Ser Pro Ala Ile Met Ser Ala Ser Pro Gly
    1               5                   10                  15

Glu Arg Val Thr Met Thr Cys Ser Ala Ser Ser Gly Val Asn Tyr Met
                20                  25                  30

His Trp Tyr Gln Gln Lys Pro Gly Thr Ser Pro Arg Arg Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Ser Met Glu Pro Glu
    65                  70                  75                  80

Asp Ala Ala Thr Tyr Tyr Cys His Gln Arg Gly Ser Tyr Thr Phe Gly
                    85                  90                  95
```

```
Gly Gly Thr Lys Leu Glu Ile Lys Arg Thr Val Ala Ala Pro Ser Val
            100                 105                 110

Phe Ile Phe Pro Pro Ser Asp Glu Gln Leu Lys Ser Gly Thr Ala Ser
            115                 120                 125

Val Val Cys Leu Leu Asn Asn Phe Tyr Pro Arg Glu Ala Lys Val Gln
        130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu Cys
    210

<210> SEQ ID NO 15
<211> LENGTH: 121
<212> TYPE: PRT
<213> ORGANISM: Artificial Sequence
<220> FEATURE:
<223> OTHER INFORMATION: VH sequence

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser
        115                 120

<210> SEQ ID NO 16
<211> LENGTH: 108
<212> TYPE: PRT
<213> ORGANISM: Artificial Sequence
<220> FEATURE:
<223> OTHER INFORMATION: VL sequence
```

<400> SEQUENCE: 16

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys
            100                 105

<210> SEQ ID NO 17
<211> LENGTH: 451
<212> TYPE: PRT
<213> ORGANISM: Artificial Sequence
<220> FEATURE:
<223> OTHER INFORMATION: Heavy chain sequence

<400> SEQUENCE: 17

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Ala Glu Pro Lys Ser Cys
    210                 215                 220

Asp Lys Thr His Thr Cys Pro Pro Cys Pro Ala Pro Glu Leu Leu Gly
225                 230                 235                 240

```
Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 18
<211> LENGTH: 213
<212> TYPE: PRT
<213> ORGANISM: Artificial Sequence
<220> FEATURE:
<223> OTHER INFORMATION: Light chain sequence

<400> SEQUENCE: 18

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140
```

-continued

```
Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
            195                 200                 205

Asn Arg Gly Glu Cys
        210
```

DOSAGE REGIMES FOR THE ADMINISTRATION OF AN ANTI-CD19 ADC

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 27308 Byte ASCII (Text) file named "5_Sequence_listing.TXT," created on Dec. 12, 2019.

FIELD

The present disclosure relates to the treatment of pathological conditions, such as cancer, with Antibody Drug Conjugates (ADCs). In particular, the present disclosure relates to administration of ADCs which bind to CD19 (CD19-ADCs).

BACKGROUND

Antibody Therapy

Antibody therapy has been established for the targeted treatment of subjects with cancer, immunological and angiogenic disorders (Carter, P. (2006) Nature Reviews Immunology 6:343-357). The use of antibody-drug conjugates (ADC), i.e. immunoconjugates, for the local delivery of cytotoxic or cytostatic agents, i.e. drugs to kill or inhibit tumour cells in the treatment of cancer, targets delivery of the drug moiety to tumours, and intracellular accumulation therein, whereas systemic administration of these unconjugated drug agents may result in unacceptable levels of toxicity to normal cells (Xie et al (2006) Expert. Opin. Biol. Ther. 6(3):281-291; Kovtun et al (2006) Cancer Res. 66(6): 3214-3121; Law et al (2006) Cancer Res. 66(4):2328-2337; Wu et al (2005) Nature Biotech. 23(9):1137-1145; Lambert J. (2005) Current Opin. in Pharmacol. 5:543-549; Hamann P. (2005) Expert Opin. Ther. Patents 15(9):1087-1103; Payne, G. (2003) Cancer Cell 3:207-212; Trail et al (2003) Cancer Immunol. Immunother. 52:328-337; Syrigos and Epenetos (1999) Anticancer Research 19:605-614).

CD19

CD19 is a 95 kDa membrane receptor that is expressed early in B cell differentiation and continues to be expressed until the B cells are triggered to terminally differentiate (Pezzutto et al. (1987), J. Immunol 138:2793; Tedder et al (1994) Immunol Today 15:437). The CD19 extracellular domain contains two C2-type immunoglobulin (IG)-like domains separated by a smaller disulfide-linked domain. The CD19 cytoplasmic domain is structurally unique, but highly conserved between human, mouse, and guinea pig (Fujimoto et al., (1998) Semin Immunol. 10:267). CD19 is part of a protein complex found on the cell surface of B-lymphocytes. The protein complex includes CD19, CD21 (complement receptor, type 2), CD81 (TAPA-1), and CD225 (Leu-13) (Fujimoto, supra).

CD19 is an important regulator of transmembrane signals in B cells. An increase or decrease in the cell surface density of CD19 affects B cell development and function, resulting in diseases such as autoimmunity or hypogammaglobulinemia. The CD19 complex potentiates the response of B cells to antigen in vivo through cross-linking of two separate signal transduction complexes found on B cell membranes. The two signal transduction complexes, associated with membrane IgM and CD19, activate phospholipase C (PLC) by different mechanisms. CD19 and B cell receptor cross-linking reduces the number of IgM molecules required to activate PLC. CD19 also functions as a specialized adapter protein for the amplification of Arc family kinases (Hasegawa et ah, (2001) J Immunol 167:3190).

CD19 binding has been shown to both enhance and inhibit B-cell activation and proliferation, depending on the amount of cross-linking that occurs (Tedder, 1994, Immunol. Today 15:437). CD19 is expressed on greater than 90% of B-cell lymphomas and has been predicted to affect growth of lymphomas in vitro and in vivo.

Therapeutic Uses of Anti-CD19 ADCs

The efficacy of an Antibody Drug Conjugate comprising an anti-CD19 antibody (an anti-CD19-ADC) in the treatment of, for example, cancer has been disclosed—see, for example, WO2014/057117 and WO2016/166298.

Research continues to further improve the efficacy, tolerability, and clinical utility of anti-CD19 ADCs. To this end, the present authors have identified clinically advantageous dosage regimes for the administration of an anti-CD19 ADC.

SUMMARY

Through treatment of subjects with CD19-ADC, the present authors have developed dosage regimes that allow for improved efficacy, efficiency, and/or tolerability of CD19-ADC treatment. Interesting, it was found that the parameters required for optimal treatment efficacy, efficiency, and/or tolerability differed between indication subsets.

BRIEF DESCRIPTION OF THE FIGURES

Embodiments and experiments illustrating the principles of the disclosure will now be discussed with reference to the accompanying figures.

FIGS. 1A and 1B include amino acid sequences of VH and VL domains, as well as heavy (HC) and light chains (LC), of antibodies described herein.

LYMPHOMAS

Figure 2:
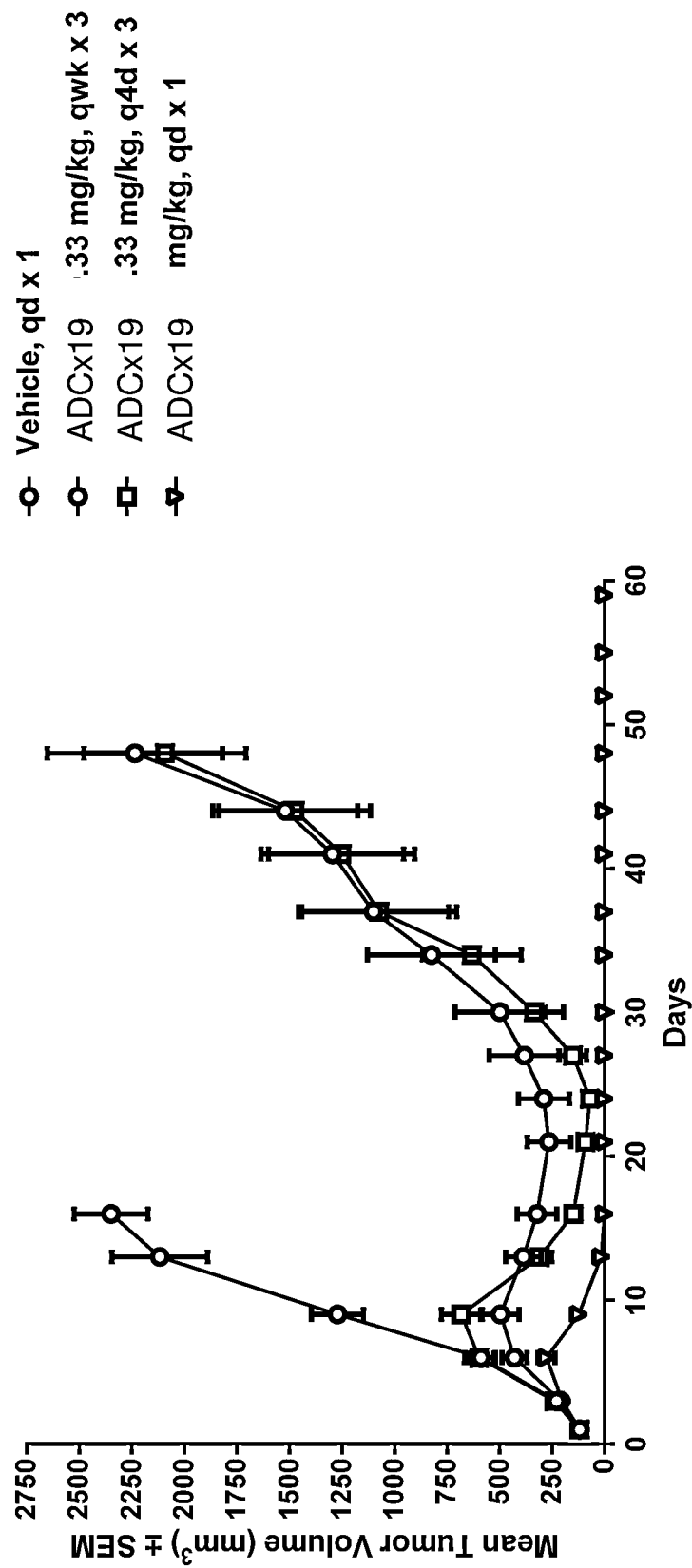
FIG. 2 is a graph showing the efficacy of ADCx19 treatment in a mouse subcutaneous Ramos-e222 xenograft in vivo model.

During treatment of a cohort of subjects with Relapsed or Refractory B-cell Lineage Non-Hodgkin Lymphoma (B-NHL)' using a single dose of CD19-ADC per 3-week treatment cycle, the present authors noted that that repetitive dosing every three weeks is not well tolerated or necessary at doses of 120 μg/kg and higher:

- Of six responding patients treated at 120 μg/kg (four complete remissions, two partial remissions), four required at least one dose delay during treatment (3 to 7 treatment cycles) due to adverse events and two were discontinued from treatment.
- Of three patients treated at 150 μg/kg received 2 to 3 treatment cycles of CD19-ADC before side effects necessitated dose delay. The delay eventually led to removal from the study since the toxicities were slow to resolve.
- Of 6 patients treated at 200 μg/kg, five attained complete response and the other attained partial response. However, all patients had some evidence of toxicity at the end of the second or third treatment cycle.

In addition, pharmacokinetic studies indicate that CD19 ADC is not rapidly cleared from the bloodstream, with trough levels at the end of each 3-week treatment cycle maintained at a relatively high level, or even gradually increasing with each treatment cycle.

Accordingly, the present authors reasoned that tapering the dose of the CD19-ADC and/or increasing the length of each treatment cycle would allow for more effective long term treatment of lymphoma subjects by providing reasonable exposure to CD19-ADC to provide efficacy while maximizing long term tolerability through reducing CD19-ADC accumulation.

Accordingly, part of the subject-matter of the present disclosure concerns the use of CD19-ADCs in tapered and/or elongated dosage regimes for treating proliferative diseases. These tapered and/or elongated regimes are expected to be associated with a range of clinical benefits, including reduced toxicity and side-effects, and the consequent expansion of the population eligible to be treated to include subjects intolerant of the side effects of known dosage regimes.

Preferably, the tapered and/or elongated dosage regimes described here are employed when the proliferative disease is lymphoma. For example, the proliferative disease may be a non-Hodgkin's Lymphoma, such as diffuse large B-cell lymphoma (DLBCL), follicular lymphoma, (FL), Mantle Cell lymphoma (MCL), chronic lymphatic lymphoma (CLL), Waldenstroms Microglobulinemia, Burkitt's lymphoma, and Marginal Zone B-cell lymphoma (MZBL).

In a first aspect the disclosure provides a method of treating a proliferative disease in a subject, said method comprising administering to a subject a CD19-ADC, wherein the CD19-ADC is administered to the subject in a tapered and/or elongated dosage regime.

The CD19-ADC may be ADCx19 as described herein.

The term "tapered dosage regime" is used herein to describe a dosage regime in which the total dose of CD19-ADC administered in the first treatment cycle (from hereon in termed the "starting dose") is greater than the total dose of CD19-ADC administered in one or more subsequent treatment cycle. A tapered dosage regime contrasts with a constant dosing regime in which the starting dose is the same as the total dose administered in each subsequent treatment cycle (see 'Constant' in Table 1, below).

In some cases, the administered dose is only reduced if the subject has attained at least Stable Disease [SD] at the end of the preceding treatment cycle (i.e. SD or better response, such as PR or CR).

Preferably the starting dose is reduced no more than once during the treatment of a subject. In these cases the total dose following dose reduction is from hereon in termed the "reduced dose".

In some cases the dose is reduced following the first treatment cycle. That is, the starting dose is administered in the first treatment cycle and the reduced dose is administered in the second and subsequent treatment cycles. Dosing regime 'Taper 6' in Table 1 is an example of such a dosing regime.

In some cases the dose is reduced following the second treatment cycle. That is, the starting dose is administered in each of the first and second treatment cycles and the reduced dose is administered in each of the third and subsequent treatment cycles. Dosing regime 'Taper 3', 'Taper 4, 'Taper 5', and 'Taper 7' in Table 1 are examples of such a dosing regime.

In some cases the starting dose is at least 120 µg/kg. In some cases the starting dose is at least 150 µg/kg, such as at least 200 µg/kg. In some cases the starting dose is about 120, 150, or 200 µg/kg. In some cases the reduced dose is about 50% of the starting dose. In some cases the reduced dose is about 60 µg/kg. In some cases the reduced dose is about 75 µg/kg. In some cases the starting dose is about 200 µg/kg and the reduced dose is about 60 µg/kg. In some cases the starting dose is about 140 to 160 µg/kg and the reduced dose is about 70 to 80 µg/kg. In some cases the starting dose is about 150 µg/kg and the reduced dose is about 75 µg/kg.

In some cases the length of each treatment cycle is 3 weeks.

In some cases the length of each treatment cycle is 6 weeks.

The term "elongated dosage regime" is used herein to describe a dosage regime in which the length of the first treatment cycle (from hereon in termed the "starting length") is shorter than the length of one or more subsequent treatment cycles. An elongated dosage regime contrasts with a constant dosing regime in which the starting length is the same as the length of each subsequent treatment cycle (see 'Constant' in Table 2, below).

In some cases, the treatment cycle length is only increased if the subject has attained at least Stable Disease [SD] at the end of the preceding treatment cycle.

Preferably the treatment cycle length is increased no more than once during the treatment of a subject. In these cases the treatment cycle length following length increase is from hereon in termed the "increased length".

In some cases the cycle length is increased following the first treatment cycle. That is, the first treatment cycle is the starting length, and each of the second and subsequent treatment cycles is the increased length. Dosing regime tong 4' in Table 2 is an example of such a dosing regime.

In some cases the cycle length is increased following the second treatment cycle. That is, each of the first and second treatment cycles is the starting length, and each of the third and subsequent treatment cycles is the increased length. Dosing regime 'Long 3' in Table 2 is an example of such a dosing regime.

In some cases the starting length is 3 weeks. In some cases the increased length is 6 weeks.

Preferably, in a tapered and elongated dosage regime the starting dose is reduced no more than once and the treatment cycle length is increased no more than once during the treatment of a subject.

In some cases, the administered dose is only reduced and/or the cycle length increased if the subject has attained at least Stable Disease [SD] at the end of the preceding treatment cycle.

In some cases the dose reduction and the length increase is made following the second treatment cycle. That is, each of the first and second treatment cycles have the starting dose and the starting length, and each of the third and subsequent treatment cycles have the reduced dose and increased length.

In some cases the starting dose is at least 120 µg/kg. In some cases the starting dose is at least 150 µg/kg, such as at least 200 µg/kg. In some cases the starting dose is about 120, 150, or 200 µg/kg. In some cases the reduced dose is about 75 µg/kg. In some cases the reduced dose is about 60 µg/kg. In some cases the starting length is 3 weeks and the increased length is 6 weeks. In some cases the starting dose and starting length are respectively about 120 µg/kg and three weeks and the reduced dose and increased length are respectively about 60 µg/kg and six weeks. In some cases the starting dose and starting length are respectively about 150 µg/kg and three weeks and the reduced dose and increased length are respectively about 60 µg/kg and six weeks. In some cases the starting dose and starting length are respectively about 140 to 160 µg/kg and three weeks and the reduced dose and increased length are respectively about 70 to 80 µg/kg and three weeks. In some cases the starting dose and starting length are respectively about 150 µg/kg and three weeks and the reduced dose and increased length are respectively about 75 µg/kg and three weeks.

The subject may be human.

The subject may have cancer, or may have been determined to have cancer. The subject may have, or have been determined to have, a CD19+ cancer or CD19+ tumour-associated non-tumour cells, such as CD19+ infiltrating cells.

Preferably, the tapered and/or elongated dosage regimes described here are employed when the subject has, is suspected of having, or have been diagnosed with a lymphoma. For example, the subject may have, may be suspected or having, or may have been diagnosed with a non-Hodgkin's Lymphoma, such as diffuse large B-cell lymphoma (DLBCL), follicular lymphoma, (FL), Mantle Cell lymphoma (MCL), chronic lymphatic lymphoma (CLL), Waldenstroms Microglobulinemia, Burkitt's lymphoma, and Marginal Zone B-cell lymphoma (MZBL).

In other, less-preferred embodiments, the subject may have, may be suspected or having, or may have been diagnosed with a leukaemia such as Hairy cell leukaemia (HCL), Hairy cell leukaemia variant (HCL-v), and Acute Lymphoblastic Leukaemia (ALL) such as Philadelphia chromosome-positive ALL (Ph+ALL) or Philadelphia chromosome-negative ALL (Ph-ALL).

The proliferative disease may be resistant, relapsed or refractory.

The subject may have, or have been determined to have Relapsed or Refractory B-cell Lineage Non-Hodgkin Lymphoma (B-NHL).

In some cases the subject has been diagnosed as having the proliferative disease prior to the start of treatment with the CD19-ADC.

In some cases the method further comprises administering a second anti-cancer compound in combination with the CD19-ADC.

Specifically envisioned combinations include: CD19-ADC with Ibrutinib, CD19-ADC with Durvalumab, CD19-ADC with rituximab, CD19-ADC with cytarabine, and CD19-ADC with rituximab and cytarabine.

In some cases the tapered and/or elongated dosage regime reduces the treatment toxicity or side-effects as compared to a constant dose level and cycle length regime.

In some cases the tapered and/or elongated dosage regime increases the treatment efficacy as compared to a constant dose level and cycle length regime.

In some cases the CD19-ADC is administered intravenously.

In a second aspect, the present disclosure provides a method of reducing the toxicity and/or side effects associated with administration of a CD19-ADC to a subject, the method comprising administering the CD19-ADC in a tapered and/or elongated dosage regime as defined herein.

In a third aspect, the present disclosure provides a method of increasing the treatment efficacy associated with administration of an CD19-ADC to a subject, the method comprising administering the CD19-ADC in tapered and/or elongated dosage regime as defined herein.

In a fourth aspect, the present disclosure provides a method of selecting a subject for treatment by a tapered and/or elongated dosage regime as described herein, which selection method comprises selecting for treatment subjects that express CD19 in a tissue of interest.

In a fifth aspect the present disclosure provides a packaged pharmaceutical product comprising a CD19-ADC as described herein in combination with a label or insert advising that the CD19-ADC should be administered in a tapered and/or elongated dosage regime.

The disclosure also provides a kit comprising:
 a first medicament comprising a CD19-ADC; and, optionally,
 a package insert or label comprising instructions for administration of the CD19-ADC in tapered and/or elongated dosage regime as described herein.

In a sixth aspect the present disclosure provides a CD19-ADC as defined herein for use in a method of treatment as described herein.

In a seventh aspect the present disclosure provides the use of a CD19-ADC as defined herein in the preparation of a medicament for use in a method of treatment as described herein.

Leukaemias

During treatment of a cohort of human subjects with relapsed or refractory Acute Lymphoblastic Leukemias (ALL) using a single dose of CD19-ADC per 3-week treatment cycle, the present authors noted that for most patients, plasma ADC concentrations when measured were near the lower limit of quantification and pharmokinetic (PK) parameters could not be discerned. In those patients, rapid drug clearance was apparent in the early time course. This observation was coupled with observation that a number of patients who attained complete recovery (CR) showed a slower clearance of ADC from the plasma was evident by treatment cycle 2.

Figure 3:
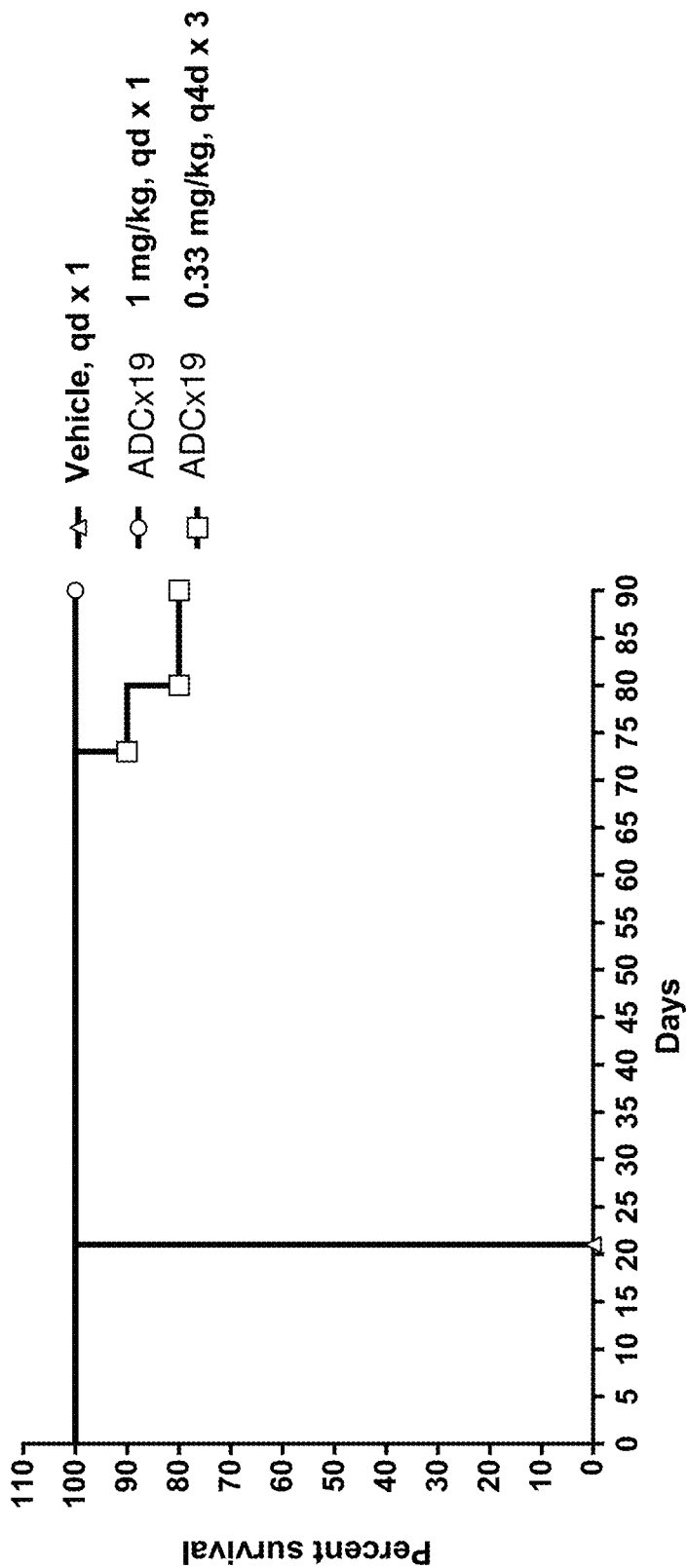
FIG. 3 is a graph showing the efficacy of ADCx19 treatment in a mouse NALM-6 tumour cell inoculation xenograft model.

Accordingly, the present authors sought an altered dosage regime to improve the efficacy of CD19-ADC treatment. Data collected from a number of different mouse xenograft models of CD19+ proliferative disease indicated that administration of CD19-ADC as a single dose on day 1 of the treatment cycle led to effective treatment, with administration of an identical total dose of AD19-ADC as a series of smaller partial doses resulting in higher mortality levels (see FIGS. 2 and 3).

Nonetheless, the present authors reasoned that fractionating the dose of the CD19-ADC and administering it at more regular intervals throughout the treatment cycle would allow for: (1) a more consistent, effective degree of ADC exposure to be maintained throughout the treatment cycle, and (2) the use of higher total doses but with decreased peak levels, thus reducing toxicity associated with peak exposure levels.

Without wishing to be bound by theory, the use of such fractionated dosage regimes is potentially especially advantageous in diseases such as acute leukaemia, where the rapid production of circulating myeloblasts acts as an antigenic sink for the CD19-ADC. This is consistent with the exploration or adoption of fractionated dosage regimes in some other treatments of subjects with leukaemia (Frey F, et al. Abstract 7002. Presented at: ASCO Annual Meeting; Jun. 3-7, 2016; Chicago; Aue G, et al. Haematologica February 2010 95: 329-332; Taksin A, et al. Leukemias (2007) 21, 66-71. Published online 19 Oct. 2006).

Accordingly, part of the subject-matter of the present disclosure concerns the use of CD19-ADCs in fractionated dosage regimes for treating proliferative diseases, in particular leukaemias. These fractionated regimes are expected to be associated with a range of clinical benefits, including improved efficacy, reduced toxicity and side-effects, and the consequent expansion of the population eligible to be treated to include subjects intolerant of the greater side effects of known dosage regimes.

Preferably, the fractionated dosage regimes described here are employed when the proliferative disease is leukaemia, such as Hairy cell leukaemia (HCL), Hairy cell leukaemia variant (HCL-v), and Acute Lymphoblastic Leukaemia (ALL) such as Philadelphia chromosome-positive ALL (Ph+ALL) or Philadelphia chromosome-negative ALL (Ph-ALL).

In an eighth aspect the disclosure provides a method of treating a proliferative disease in a subject, said method comprising administering to a subject a CD19-ADC, wherein the CD19-ADC is administered to the subject in a fractionated dosage regime.

The CD19-ADC may be ADCx19 as described herein.

The term "fractionated dosage regime" is used herein to describe a dosage regime in which the total dose of CD19-ADC administered during the treatment cycle is administered in a series of two or more partial doses during the treatment cycle. The term 'partial dose' is used herein to denote a dose of ADC that is a fraction of the total dose of ADC to be administered in the treatment cycle. The sum of all partial doses delivered in a treatment cycle equals the total dose. A fractionated dosage regime contrasts with a 'single-dose' dosing regime in which the total dose of CD19-ADC administered in the treatment cycle is administered as a single dose at the start of the treatment cycle.

Preferably the total dose of CD19-ADC is administered as partial doses of equal size regularly spaced throughout the treatment cycle. Administration to the subject once per week is particularly preferred. In some cases the total dose of CD19-ADC is administered over a three week treatment cycle in 3 equal partial doses, with a partial dose administered once a week. For example, with administration of a partial dose on days 1, 8, and 15 of a 3-week treatment cycle. Further features of fractionated dosage regimes are discussed herein.

The subject may be human. The subject may have cancer, or may have been determined to have cancer. The subject may have, or have been determined to have, a CD19+ cancer or CD19+ tumour-associated non-tumour cells, such as CD19+ infiltrating cells.

Preferably, the fractionated dosage regimes described here are employed when the subject has, is suspected of having, or have been diagnosed with leukaemia. For example, the subject may have, may be suspected or having, or may have been diagnosed with Hairy cell leukaemia (HCL), Hairy cell leukaemia variant (HCL-v), and Acute Lymphoblastic Leukaemia (ALL) such as Philadelphia chromosome-positive ALL (Ph+ALL) or Philadelphia chromosome-negative ALL (Ph-ALL).

In other, less-preferred embodiments, the subject may have, may be suspected or having, or may have been diagnosed with lymphoma. For example, with a non-Hodgkin's Lymphoma, such as diffuse large B-cell lymphoma (DLBCL), follicular lymphoma, (FL), Mantle Cell lymphoma (MCL), chronic lymphatic lymphoma (CLL), Waldenstroms Microglobulinemia, Burkitt's lymphoma, and Marginal Zone B-cell lymphoma (MZBL).

The proliferative disease may be resistant, relapsed or refractory

The subject may have, or have been determined to have Relapsed or Refractory B-cell Lineage Acute Lymphoblastic Leukemias (B-ALL).

In some cases the subject has been diagnosed as having the proliferative disease prior to the start of treatment with the CD19-ADC.

In some cases the method further comprises administering a second anti-cancer compound in combination with the CD19-ADC.

In some cases the fractional dosage regime reduces the treatment toxicity or side-effects as compared to a single dose per treatment cycle regime.

In some cases the fractional dosage regime increases the treatment efficacy as compared to a single dose per treatment cycle regime.

In some cases the CD19-ADC is administered intravenously.

In a ninth aspect, the present disclosure provides a method of reducing the toxicity and/or side effects associated with administration of a CD19-ADC to a subject, the method comprising administering the CD19-ADC in a fractionated dosage regime as defined herein.

In a tenth aspect, the present disclosure provides a method of increasing the treatment efficacy associated with administration of an CD19-ADC to a subject, the method comprising administering the CD19-ADC in a fractionated dosage regime as defined herein.

In an eleventh aspect, the present disclosure provides a method of selecting a subject for treatment by a fractionated dosage regime as described herein, which selection method comprises selecting for treatment subjects that express CD19 in a tissue of interest.

In a twelfth aspect the present disclosure provides a packaged pharmaceutical product comprising a CD19-ADC as described herein in combination with a label or insert advising that the CD19-ADC should be administered in a fractionated dosage regime.

The disclosure also provides a kit comprising:
   a first medicament comprising a CD19-ADC; and, optionally,
   a package insert or label comprising instructions for administration of the CD19-ADC in a fractionated dosage regime as described herein.

In a thirteenth aspect the present disclosure provides a CD19ADC as defined herein for use in a method of treatment as described herein.

In a fourteenth aspect the present disclosure provides the use of a CD19-ADC as defined herein in the preparation of a medicament for use in a method of treatment as described herein.

DETAILED DISCLOSURE

As described in more detail below, the present authors have reasoned that CD19-ADCs as defined herein, when administered in tapered and/or elongated dosage regimes for the treatment of lymphomas, have improved efficacy and/or reduced toxicity as compared to that observed when an ADC is administered in a regime with constant dosage size and treatment cycle length.

Thus, in a first aspect the disclosure provides a method of treating a proliferative disease in a subject, said method comprising administering to a subject a CD19-ADC, wherein the CD19-ADC is administered to the subject in a tapered and/or elongated dosage regimes.

Further, the present authors have reasoned that CD19-ADCs as defined herein, when administered in a fractionated dosage regime for the treatment of leukaemia, have improved efficacy and/or reduced toxicity as compared to that observed when an equivalent amount of ADC is administered as a single dose.

Thus, in an eighth aspect the disclosure provides a method of treating a proliferative disease in a subject, said method comprising administering to a subject a CD19-ADC, wherein the CD19-ADC is administered to the subject in a fractionated dosage regime.

These findings provides additional utilities for such CD19-ADCs, implying new therapeutic contexts for use, for example in relation to patient groups with heightened sensitivity to CD19-ADC toxicity, or in relation to patient groups requiring larger doses of CD19-ADC for effective treatment.

Anti-CD19 ADCs

As used herein, the term "CD19-ADC" refers to an ADC in which the antibody component is an anti-CD19 antibody. The term "PBD-ADC" refers to an ADC in which the drug component is a pyrrolobenzodiazepine (PBD) warhead. The term "anti-CD19-ADC" refers to an ADC in which the antibody component is an anti-CD19 antibody, and the drug component is a PBD warhead.

The ADC may comprise a conjugate of formula $L\text{-}(D^L)_p$, where $D^L$ is of formula I or II:

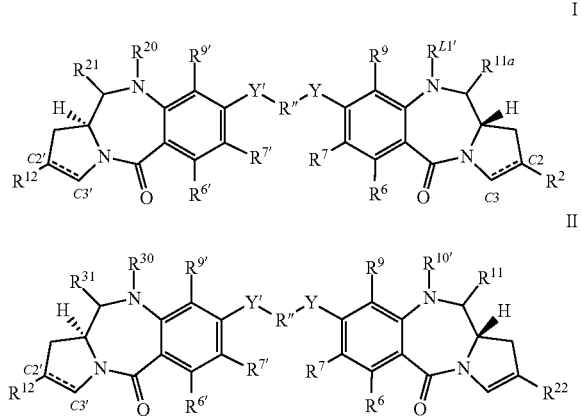

wherein:
L is an antibody (Ab) which is an antibody that binds to CD19;
when there is a double bond present between C2' and C3', $R^{12}$ is selected from the group consisting of:
(ia) $C_{5-10}$ aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{1-3}$ alkylene;
(ib) $C_{1-5}$ saturated aliphatic alkyl;
(ic) $C_{3-6}$ saturated cycloalkyl;

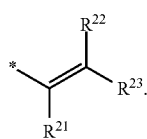
(id)

wherein each of $R^{21}$, $R^{22}$ and $R^{23}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5;

(ie)

wherein one of $R^{25a}$ and $R^{25b}$ is H and the other is selected from: phenyl, which phenyl is optionally substituted by a group selected from halo, methyl, methoxy; pyridyl; and thiophenyl; and

(if)

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;
when there is a single bond present between C2' and C3', $R^{12}$ is

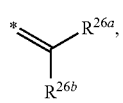

where $R^{26a}$ and $R^{26b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{26a}$ and $R^{26b}$ is H, the other is selected from nitrile and a $C_{1-4}$ alkyl ester;
$R^6$ and $R^9$ are independently selected from H, R, OH, OR, SH, SR, $NH_2$, NHR, NRR', nitro, $Me_3Sn$ and halo;
where R and R' are independently selected from optionally substituted $C_{1-12}$ alkyl, $C_{3-20}$ heterocyclyl and $C_{5-20}$ aryl groups;
$R^7$ is selected from H, R, OH, OR, SH, SR, $NH_2$, NHR, NHRR', nitro, $Me_3Sn$ and halo;
R" is a $C_{3-12}$ alkylene group, which chain may be interrupted by one or more heteroatoms, e.g. O, S, $NR^{N2}$ (where $R^{N2}$ is H or $C_{1-4}$ alkyl), and/or aromatic rings, e.g. benzene or pyridine;
Y and Y' are selected from O, S, or NH;
$R^{6'}$, $R^{7'}$, $R^{9'}$ are selected from the same groups as $R^6$, $R^7$ and $R^9$ respectively;
[Formula I]
$R^{L1'}$ is a linker for connection to the antibody (Ab);
$R^{11a}$ is selected from OH, $OR^A$, where $R^A$ is $C_{1-4}$ alkyl, and $SO_zM$, where z is 2 or 3 and M is a monovalent pharmaceutically acceptable cation;
$R^{20}$ and $R^{21}$ either together form a double bond between the nitrogen and carbon atoms to which they are bound or;
$R^{20}$ is selected from H and $R^C$, where $R^C$ is a capping group;
$R^{21}$ is selected from OH, $OR^A$ and $SO_zM$;
when there is a double bond present between C2 and C3, $R^2$ is selected from the group consisting of:
(ia) $C_{5-10}$ aryl group, optionally substituted by one or more substituents selected from the group comprising:

halo, nitro, cyano, ether, carboxy, ester, $C_{1-7}$ alkyl, $C_{3-7}$ heterocyclyl and bis-oxy-$C_{1-3}$ alkylene;

(ib) $C_{1-5}$ saturated aliphatic alkyl;

(ic) $C_{3-6}$ saturated cycloalkyl;

(id)

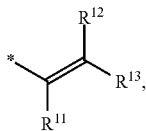

wherein each of $R^{11}$, $R^{12}$ and $R^{13}$ are independently selected from H, $C_{1-3}$ saturated alkyl, $C_{2-3}$ alkenyl, $C_{2-3}$ alkynyl and cyclopropyl, where the total number of carbon atoms in the $R^2$ group is no more than 5;

(ie)

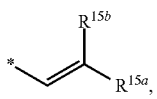

wherein one of $R^{15a}$ and $R^{15b}$ is H and the other is selected from: phenyl, which phenyl is optionally substituted by a group selected from halo, methyl, methoxy; pyridyl; and thiophenyl; and (if)

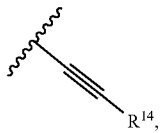

where $R^{14}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

when there is a single bond present between C2 and C3, $R^2$ is

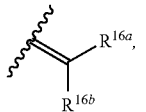

where $R^{16a}$ and $R^{16b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{16a}$ and $R^{16b}$ is H, the other is selected from nitrile and a $C_{1-4}$ alkyl ester;

[Formula II]

$R^{22}$ is of formula IIIa, formula IIIb or formula IIIc:

IIIa (a)

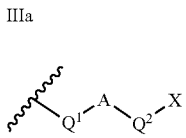

where A is a $C_{5-7}$ aryl group, and either (i) $Q^1$ is a single bond, and $Q^2$ is selected from a single bond and —Z—$(CH_2)_n$—, where Z is selected from a single bond, O, S and NH and n is from 1 to 3; or (ii) a1 is —CH=CH—, and $Q^2$ is a single bond;

IIIb (b)

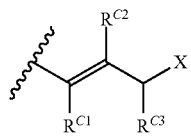

where;

$R^{C1}$, $R^{C2}$ and $R^{C3}$ are independently selected from H and unsubstituted $C_{1-2}$ alkyl;

IIIc (c)

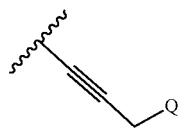

where Q is selected from O—$R^{L2'}$, S—$R^{L2'}$ and $NR^N$—$R^{L2'}$, and $R^N$ is selected from H, methyl and ethyl X is selected from the group comprising: O—$R^{L2'}$, S—$R^{L2'}$, $CO_2$—$R^{L2'}$, NH—C(=O)—$R^{L2'}$, NHNH—$R^{L2'}$, CONHNH—$R^{L2'}$,

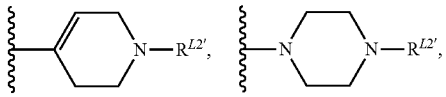

$NR^N R^{L2'}$, wherein $R^N$ is selected from the group comprising H and $C_{1-4}$ alkyl;

$R^{L2'}$ is a linker for connection to the antibody (Ab);

$R^{10}$ and $R^{11}$ either together form a double bond between the nitrogen and carbon atoms to which they are bound or;

$R^{10}$ is H and $R^{11}$ is selected from OH, $OR^A$ and $SO_zM$;

$R^{30}$ and $R^{31}$ either together form a double bond between the nitrogen and carbon atoms to which they are bound or;

$R^{30}$ is H and $R^{31}$ is selected from OH, $OR^A$ and $SO_zM$.

In some embodiments L-$R^{L1'}$ or L-$R^{L2'}$ is a group:

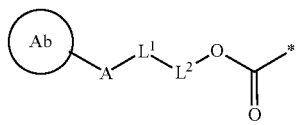

where the asterisk indicates the point of attachment to the PBD, Ab is the antibody, $L^1$ is a cleavable linker, A is a connecting group connecting $L^1$ to the antibody, $L^2$ is a covalent bond or together with —OC(=O)— forms a self-immolative linker.

In some of these embodiments, $L^1$ is enzyme cleavable.

It has previously been shown that such ADCs are useful in the treatment of CD19 expressing cancers (see, for example, WO2014/057117, which is incorporated by reference herein in its entirety).

The term anti-CD19-ADC may include any embodiment described in WO2014/057117. In particular, in preferred embodiments the ADC may have the chemical structure:

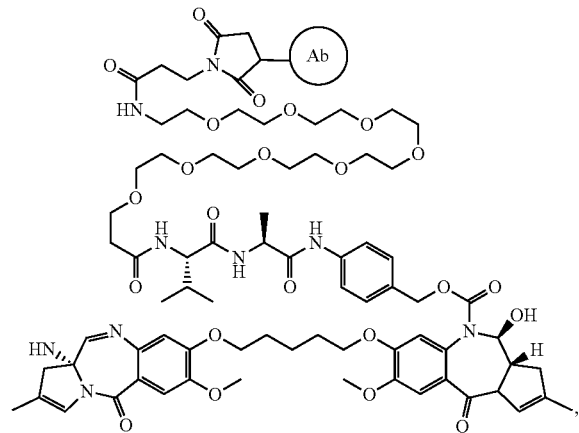

where the Ab is a CD19 antibody, and the DAR is between 1 and 8.

The antibody may comprise a VH domain having the sequence according to any one of SEQ ID NOs. 1, 2, 3, 4, 5 or 6, optionally further comprising a VL domain having the sequence according to any one of SEQ ID NOs. 7, 8, 9, 10, 11 or 12.

In some aspects the antibody component of the anti-CD19-ADC is an antibody comprising: VH and VL domains respectively having the sequences of: SEQ ID NO. 1 and SEQ ID NO. 7, SEQ ID NO. 2 and SEQ ID NO. 8, SEQ ID NO. 3 and SEQ ID NO. 9, SEQ ID NO. 4 and SEQ ID NO. 10, SEQ ID NO. 5 and SEQ ID NO. 11, or SEQ ID NO. 6 and SEQ ID NO. 12.

In preferred embodiments the antibody comprises a VH domain having the sequence according to SEQ ID NO. 2. In preferred embodiments the antibody comprises a VL domain having the sequence according to SEQ ID NO. 8.

In preferred embodiments the antibody comprises a VH domain and a VL domain, the VH and domain having the sequence of SEQ ID NO. 2 and the VL domain having the sequences of SEQ ID NO. 8.

The VH and VL domain(s) may pair so as to form an antibody antigen binding site that binds CD19.

In some embodiments the antibody is an intact antibody comprising a VH domain and a VL domain, the VH and VL domains having sequences of SEQ ID NO. 2 and SEQ ID NO. 8.

In some embodiments the antibody is an antibody comprising a heavy chain having sequences of SEQ ID NO. 13 and a light chain having the sequences of SEQ ID NO. 14.

In some embodiments the antibody is a fully human monoclonal IgG1 antibody, preferably IgG1,κ.

In some embodiments the antibody is the RB4v1.2 antibody described in WO2014/057117.

In an aspect the antibody is an antibody as described herein which has been modified (or further modified) as described below. In some embodiments the antibody is a humanised, deimmunised or resurfaced version of an antibody disclosed herein.

The most preferred anti-CD19-ADC for use with the aspects of the present disclosure is ADCX19, as described herein below.

ADCx19

ADCX19 is an antibody drug conjugate composed of a humanized antibody against human CD19 attached to a pyrrolobenzodiazepine (PBD) warhead via a cleavable linker. The mechanism of action of ADCX19 depends on CD19 binding. The CD19 specific antibody targets the antibody drug conjugate (ADC) to cells expressing CD19. Upon binding, the ADC internalizes and is transported to the lysosome, where the protease sensitive linker is cleaved and free PBD dimer is released inside the target cell. The released PBD dimer inhibits transcription in a sequence-selective manner, due either to direct inhibition of RNA polymerase or inhibition of the interaction of associated transcription factors. The PBD dimer produces covalent crosslinks that do not distort the DNA double helix and which are not recognized by nucleotide excision repair factors, allowing for a longer effective period (Hartley 2011). These DNA crosslinks cause strand breaks when the DNA replication fork reaches them, leading to apoptosis induction.

It has the chemical structure:

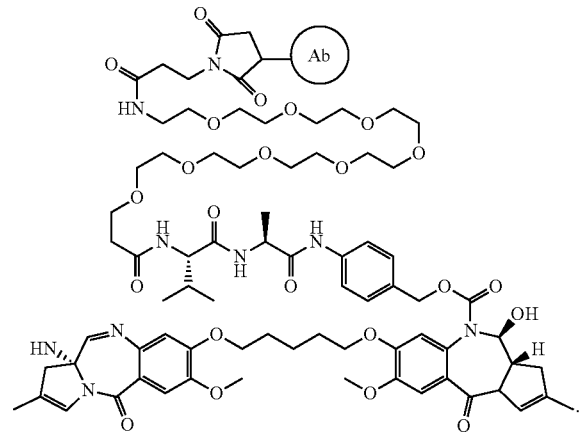

Ab represents Antibody RB4v1.2 (antibody with the VH and VL sequences SEQ ID NO. 2 and SEQ ID NO. 8, respectively). It is synthesised as described in WO2014/057117 (RB4v1.2-E) and typically has a DAR (Drug to Antibody Ratio) of 2+/−0.3.

CD19 Binding

As used herein, "binds CD19" is used to mean the antibody binds CD19 with a higher affinity than a non-specific partner such as Bovine Serum Albumin (BSA, Genbank accession no. CAA76847, version no. CAA76847.1 GI:3336842, record update date: Jan. 7, 2011 02:30 PM). In some embodiments the antibody binds CD19 with an association constant ($K_a$) at least 2, 3, 4, 5, 10, 20, 50, 100, 200, 500, 1000, 2000, 5000, $10^4$, $10^5$ or $10^6$-fold higher than the antibody's association constant for BSA, when measured at physiological conditions. The antibodies of the disclosure can bind CD19 with a high affinity. For example, in some embodiments the antibody can bind CD19 with a $K_D$ equal to or less than about $10^{-6}$ M, such as $1\times10^{-6}$, $10^{-7}$, $10^{-8}$, $10^{-9}$, $10^{-10}$, $10^{-11}$, $10^{-12}$, $10^{-13}$ or $10^{-14}$.

In some embodiments, CD19 polypeptide corresponds to Genbank accession no. NP_001171569, version no. NP_001171569.1 GI:296010921, record update date: Sep. 10, 2012 12:43 AM. In one embodiment, the nucleic acid encoding CD19 polypeptide corresponds to Genbank accession no NM_001178098, version no. NM_001178098.1 GI:296010920, record update date: Sep. 10, 2012 12:43 AM. In some embodiments, CD19 polypeptide corresponds to Uniprot/Swiss-Prot accession No. P15391.

Tapered and/or Elongated Dosage Regimes

The term "tapered dosage regime" is used herein to describe a dosage regime in which the total dose of CD19-ADC administered in the first treatment cycle (from hereon in termed the "starting dose") is greater than the total dose of CD19-ADC administered in one or more subsequent treatment cycle. A tapered dosage regime contrasts with a constant dosing regime in which the starting dose is the same as the total dose administered in each subsequent treatment cycle (see 'Constant' in Table 1, below).

As used herein, the term 'total dose' is used to mean the total amount of ADC administered during a single treatment cycle.

A subject's tapered dosage regime may consist of 2, 3, 4, 5, 6, 7, 8, 9, 10, 11, 12, 13, 14, 15, 16, 17, 18, 19, 20, 21, 22, 23, 24, 25, 26, 27, 28, 29, 30, or more treatment cycles. In some cases, the dosage regime is ended once the subject attains CR. In some cases, the dosage regime is ended when the subject experiences a DLT. In some cases, the dosage regime is considered as ended if a dose delay exceeding the length of the preceding treatment cycle is required.

In a tapered dosage regime, the starting dose may be reduced no more than once, no more than twice, or no more than three times during the dosage regime. In cases where there are two or more reductions to the starting dose, each reduction may be by the same or a different amount. A total dose may be held constant for one, two, three, or more than three treatment cycles before it is reduced (see Table 1, below, for examples).

to 10 µg/kg, 11 to 20 µg/kg, 21 to 30 µg/kg, 31 to 40 µg/kg, 41 to 50 µg/kg, 51 to 60 µg/kg, 61 to 70 µg/kg, 71 to 80 µg/kg, 81 to 90 µg/kg, 91 to 100 µg/kg, 101 to 120 µg/kg, 121 to 140 µg/kg, 141 to 160 µg/kg, 161 to 180 µg/kg, 181 to 200 µg/kg, 201 to 220 µg/kg, 221 to 240 µg/kg, 241 to 260 µg/kg, 261 to 280 µg/kg, 281 to 300 µg/kg, 301 to 320 µg/kg, 321 to 340 µg/kg, 341 to 360 µg/kg, 361 to 380 µg/kg, 381 to 400 µg/kg, 401 to 420 µg/kg, 421 to 440 µg/kg, 441 to 460 µg/kg, 461 to 480 µg/kg, 481 to 500 µg/kg, 501 to 520 µg/kg, 521 to 540 µg/kg, 541 to 560 µg/kg, 561 to 580 µg/kg, or 581 to 600 µg/kg.

In some cases the starting dose is about 120, 150, or 200 µg/kg. In some cases the starting dose is about 140 to 160 µg/kg In some cases the starting dose is about 150 µg/kg.

In some cases, each dose reduction reduces the administered dose by at least 50%, 55%, 60%, 65%, 70%, 75%, 80%, 85%, 90% or at least 95%. In some cases, each dose reduction reduces the administered dose by about 50%.

Preferably the starting dose is reduced no more than once during the treatment of a subject. In these cases the total dose following dose reduction is from hereon termed the "reduced dose".

In some cases the dose is reduced following the first treatment cycle. That is, the starting dose is administered in the first treatment cycle and the reduced dose is administered in the second and subsequent treatment cycles. Dosing regime 'Taper 6' in Table 1 is an example of such a dosing regime.

In some cases the dose is reduced following the second treatment cycle. That is, the starting dose is administered in each of the first and second treatment cycles and the reduced dose is administered in each of the third and subsequent treatment cycles. Dosing regime 'Taper 3', 'Taper 4, 'Taper 5', and 'Taper 7' in Table 1 are examples of such a dosing regime.

In some cases the reduced dose is about 10, 15, 20, 25, 30, 35, 40, 45, 50, 55, 60, 65, 70, 75, 80, 85, 90, 95, 100, 120, 150, 200, 250, or 300 µg/kg. In some cases the reduced dose is 1 to 10 µg/kg, 11 to 20 µg/kg, 21 to 30 µg/kg, 31 to 40 µg/kg, 41 to 50 µg/kg, 51 to 60 µg/kg, 61 to 70 µg/kg, 71 to 80 µg/kg, 81 to 90 µg/kg, 91 to 100 µg/kg, 101 to 120 µg/kg, 121 to 140 µg/kg, 141 to 160 µg/kg, 161 to 180 µg/kg, 181

TABLE 1

| Dosing Regime | Dose (µg/kg) | | | | | | |
|---|---|---|---|---|---|---|---|
| | Cycle 1 | Cycle 2 | Cycle 3 | Cycle 4 | Cycle 5 | Cycle 6 | Cycle 7 |
| Constant | 100 | 100 | 100 | 100 | 100 | 100 | 100 |
| Taper 1 | 100 | 90 | 80 | 70 | 60 | 50 | 40 |
| Taper 2 | 100 | 90 | 70 | 65 | 60 | 40 | 40 |
| Taper 3 | 120 | 120 | 60 | 60 | 60 | 60 | 60 |
| Taper 4 | 150 | 150 | 60 | 60 | 60 | 60 | 60 |
| Taper 5 | 200 | 200 | 60 | 60 | 60 | 60 | 60 |
| Taper 6 | 200 | 60 | 60 | 60 | 60 | 60 | 60 |
| Taper 7 | 150 | 150 | 75 | 75 | 75 | 75 | 75 |

In some cases, the administered dose is only reduced if the subject has attained at least Stable Disease [SD] at the end of the preceding treatment cycle.

In some cases the starting dose is at least about 10, 20, 30, 40, 50, 60, 70, 80, 90, 100, 110, 120, 130, 140, 150, 160, 170, 180, 190, or 200 µg/kg. In some cases the starting dose is at least 120 µg/kg. In some cases the starting dose is at least 150 µg/kg, such as at least 200 µg/kg.

In some cases the starting dose is about 10, 20, 30, 40, 50, 60, 70, 80, 90, 100, 120, 150, 200, 250, 300, 350, 400, 450, 500, 550, or 600 µg/kg. In some cases the starting dose is 1 to 200 µg/kg, 201 to 220 µg/kg, 221 to 240 µg/kg, 241 to 260 µg/kg, 261 to 280 µg/kg, or 281 to 300 µg/kg.

In some cases the reduced dose is 60 µg/kg.

In some cases the reduced dose is about 70-80 µg/kg. In some cases the reduced dose is 75 µg/kg.

In some cases the length of each treatment cycle is 1 week, 2 weeks, 3 weeks, 4 weeks, 5 weeks, 6 weeks, 7 weeks, 8 weeks, or 9 weeks.

In some cases the length of each treatment cycle is 3 weeks. In some cases the length of each treatment cycle is 6 weeks.

The term "elongated dosage regime" is used herein to describe a dosage regime in which the length of the first treatment cycle (from hereon in termed the "starting length") is shorter than the length of one or more subsequent treatment cycle. An elongated dosage regime contrasts with a constant dosing regime in which the starting length is the same the length of each subsequent treatment cycle (see 'Constant' in Table 2, below).

A subject's tapered dosage regime may consist of 2, 3, 4, 5, 6, 7, 8, 9, 10, 11, 12, 13, 14, 15, 16, 17, 18, 19, 20, 21, 22, 23, 24, 25, 26, 27, 28, 29 or 30 treatment cycles. In some cases the dosage regime is ended once the subject attains CR. In some cases the dosage regime is ended when the subject experiences a DLT. In some cases the dosage regime is considered as ended if a dose delay exceeding the length of the preceding treatment cycle is required.

In an elongated dosage regime the treatment cycle length may be increased no more than once, no more than twice, or no more than three times during the dosage regime. In cases where there are two or more increases in length, each increase may be by the same or a different amount. The length of treatment cycle may be held constant for one, two, three, or more than three treatment cycles before it is increased (see Table 2, below, for examples).

Preferably the treatment cycle length is increased no more than once during the treatment of a subject. In these cases the treatment cycle length following length increase is from hereon in termed the "increased length".

In some cases the cycle length is increased following the first treatment cycle. That is, the first treatment cycle is the starting length, and each of the second and subsequent treatment cycles is the increased length. Dosing regime tong 4' in Table 2 is an example of such a dosing regime.

In some cases the cycle length is increased following the second treatment cycle. That is, each of the first and second treatment cycles is the starting length, and each of the third and subsequent treatment cycles is the increased length. Dosing regime 'Long 3' in Table 2 is an example of such a dosing regime.

In some cases the increased length is 2 weeks, 3 weeks, 4 weeks, 5 weeks, 6 weeks, 7 weeks, 8 weeks, 9 weeks, 10 weeks, 11 weeks, or 12 weeks.

In some cases the starting length is 3 weeks. In some cases the increased length is 6 weeks. In some cases the starting length is 3 weeks and the increased length is 6 weeks.

A dosing regime may be tapered, elongated, or both tapered and elongated.

TABLE 2

| Dosing Regime | Cycle length (weeks) | | | | | | |
|---|---|---|---|---|---|---|---|
| | Cycle 1 | Cycle 2 | Cycle 3 | Cycle 4 | Cycle 5 | Cycle 6 | Cycle 7 |
| Constant | 3 | 3 | 3 | 3 | 3 | 3 | 3 |
| Long 1 | 3 | 4 | 5 | 6 | 6 | 6 | 6 |
| Long 2 | 3 | 3 | 4 | 5 | 5 | 5 | 5 |
| Long 3 | 3 | 3 | 6 | 6 | 6 | 6 | 6 |
| Long 4 | 3 | 6 | 6 | 6 | 6 | 6 | 6 |

In some cases, the treatment cycle length is only increased if the subject has attained at least Stable Disease [SD] at the end of the preceding treatment cycle.

Preferably, the dose is administered as a single dose on Day 1 of the treatment cycle. So, for example, a subject starting the 'constant' dosing regime above may receive a dose on Day 1, Day 22, Day 43, and so on until the regime is halted.

Following this pattern, a subject starting the tong 3' dosing regime above may receive a dose on Day 1-(+3 weeks)→Day 22-(+3 weeks)→Day 43-(+6 weeks)→Day 85-(+6 weeks)→Day 127 and so on until the regime is halted. However, preferably the Day 1' of the first treatment cycle of increased length is delayed so that the time elapsed between Day 1' of the final shorter treatment cycle and Day 1' of the first treatment cycle of increased length is equal in length to the increased treatment cycle. Accordingly, in the preferred administration pattern of the 'Long 3' dosing regime a subject receive a dose on Day 1-(+3 weeks)→Day 22-(+3 weeks)→-(+3 week delay)→Day 64-(+6 weeks)→Day 106-(+6 weeks)→Day 148 and so on until the regime is halted.

In some cases the starting length is 1 week, 2 weeks, 3 weeks, 4 weeks, 5 weeks, 6 weeks, 7 weeks, 8 weeks, or 9 weeks.

In some cases the starting length is 3 weeks.

In some cases each length increase increases the treatment cycle length by at least 50%, 55%, 60%, 65%, 70%, 75%, 80%, 85%, 90%, 95% or at least 100%. In some cases each length increase increases the treatment cycle length by 1 week, 2 weeks, 3 weeks, 4 weeks, 5 weeks, or 6 weeks.

Tapered and elongated dosing regimes incorporate both of those elements as described herein.

In some cases, the administered dose is only reduced and/or the treatment cycle length increased if the subject has attained at least Stable Disease [SD] at the end of the preceding treatment cycle.

Preferably, in a tapered and elongated dosage regime the starting dose is reduced no more than once and the treatment cycle length is increased no more than once during the treatment of a subject.

In some cases the dose reduction and the length increase is made following the first treatment cycle. That is, the first treatment cycle has the starting dose and the starting length, and each of the second and subsequent treatment cycles have the reduced dose and increased length.

In some cases the dose reduction and the length increase is made following the second treatment cycle. That is, each of the first and second treatment cycles have the starting dose and the starting length, and each of the third and subsequent treatment cycles have the reduced dose and increased length.

In some cases the starting dose is at least about 10, 20, 30, 40, 50, 60, 70, 80, 90, 100, 110, 120, 130, 140, 150, 160, 170, 180, 190, or 200 µg/kg. In some cases the starting dose is at least 120 µg/kg. In some cases the starting dose is at least 150 µg/kg, such as at least 200 µg/kg.

In some cases the starting dose is about 10, 20, 30, 40, 50, 60, 70, 80, 90, 100, 120, 150, 200, 250, 300, 350, 400, 450, 500, 550, or 600 µg/kg. In some cases the starting dose is 1 to 10 µg/kg, 11 to 20 µg/kg, 21 to 30 µg/kg, 31 to 40 µg/kg, 41 to 50 µg/kg, 51 to 60 µg/kg, 61 to 70 µg/kg, 71 to 80

µg/kg, 81 to 90 µg/kg, 91 to 100 µg/kg, 101 to 120 µg/kg, 121 to 140 µg/kg, 141 to 160 µg/kg, 161 to 180 µg/kg, 181 to 200 µg/kg, 201 to 220 µg/kg, 221 to 240 µg/kg, 241 to 260 µg/kg, 261 to 280 µg/kg, 281 to 300 µg/kg, 301 to 320 µg/kg, 321 to 340 µg/kg, 341 to 360 µg/kg, 361 to 380 µg/kg, 381 to 400 µg/kg, 401 to 420 µg/kg, 421 to 440 µg/kg, 441 to 460 µg/kg, 461 to 480 µg/kg, 481 to 500 µg/kg, 501 to 520 µg/kg, 521 to 540 µg/kg, 541 to 560 µg/kg, 561 to 580 µg/kg, or 581 to 600 µg/kg.

In some cases the reduced dose is about 10, 15, 20, 25, 30, 35, 40, 45, 50, 55, 60, 65, 70, 75, 80, 85, 90, 95, 100, 120, 150, 200, 250, or 300 µg/kg. In some cases the reduced dose is 1 to 10 µg/kg, 11 to 20 µg/kg, 21 to 30 µg/kg, 31 to 40 µg/kg, 41 to 50 µg/kg, 51 to 60 µg/kg, 61 to 70 µg/kg, 71 to 80 µg/kg, 81 to 90 µg/kg, 91 to 100 µg/kg, 101 to 120 µg/kg, 121 to 140 µg/kg, 141 to 160 µg/kg, 161 to 180 µg/kg, 181 to 200 µg/kg, 201 to 220 µg/kg, 221 to 240 µg/kg, 241 to 260 µg/kg, 261 to 280 µg/kg, or 281 to 300 µg/kg.

In some cases the starting length is 1 week, 2 weeks, 3 weeks, 4 weeks, 5 weeks, 6 weeks, 7 weeks, 8 weeks, or 9 weeks.

In some cases the increased length is 2 weeks, 3 weeks, 4 weeks, 5 weeks, 6 weeks, 7 weeks, 8 weeks, 9 weeks, 10 weeks, 11 weeks, or 12 weeks.

In some cases the starting dose is about 120, 150, or 200 µg/kg. In some cases the starting dose is about 140 to 160 µg/kg. In some cases the starting dose is about 150 µg/kg. In some cases the reduced dose is about 60 µg/kg. In some cases the reduced dose is about 70 to 80 µg/kg. In some cases the reduced dose is about 75 µg/kg. In some cases the starting length is 3 weeks and the increased length is 6 weeks. In some cases the starting dose and starting length are respectively about 120 µg/kg and three weeks and the reduced dose and increased length are respectively about 60 µg/kg and six weeks. In some cases the starting dose and starting length are respectively about 150 µg/kg and three weeks and the reduced dose and increased length are respectively about 60 µg/kg and six weeks.

In some preferred cases the starting dose and starting length are respectively about 140 to 160 µg/kg and three weeks and the reduced dose and increased length are respectively about 70 to 80 µg/kg and three weeks (i.e. the regime is tapered but NOT elongated).

In some particularly preferred cases the starting dose and starting length are respectively about 150 µg/kg and three weeks and the reduced dose and increased length are respectively about 75 µg/kg and three weeks (i.e. the regime is tapered but NOT elongated).

In some particularly preferred cases, the dosing regime of the present disclosure is as shown in Table 3 below, with [+21] indicating that the reduced 75 µg/kg dose may be repeated at three weekly intervals for as many treatment cycles as deemed appropriate by the medical professional administering the ADC.

treatment cycle. The term 'partial dose' is used herein to denote a dose of ADC that is a fraction of the total dose of ADC to be administered in the treatment cycle. The sum of all partial doses delivered in a treatment cycle equals the total dose. A fractionated dosage regime contrasts with a 'single-dose' dosing regime in which the total dose of CD19-ADC administered in the treatment cycle is administered as a single dose at the start of the treatment cycle.

For example, in an example single-dose dosing regime for a CD19-ADC, 100% of the total dose of CD19-ADC administered during the treatment cycle is administered on day 1 of a 3-week treatment cycle. The subject is then monitored throughout the cycle and the subject's level of response used to decide if the treatment cycle should be repeated, stopped, or amended. In contrast, a fractionated dosage regime may involve administering only 33% of the total dose of ADC administered during the treatment cycle on day 1 of a 3-week treatment cycle, with a further 33% administered on day 8, and the final 33% administered on day 15.

The total dose administered may be fractionated into any number of separate doses, with the number being determined according to the clinical requirements of the subject. For example, the total dose administered may be fractionated into 2, 3, 4, 5, 6, 7, 8, 9, 10 or more than 10 doses.

The amount of CD19-ADC administered in each partial dose may be the same or different. So, for example, a total dose of 100 units of ADC delivered in 3 partial doses may be delivered as (1×50 units, 1×30 units, and 1×20 units) or (3×33⅓ units). Preferably all of the partial doses contain the same amount of CD19-ADC i.e. all of the partial doses are of equal size.

The time interval between one partial dose and the next partial dose may be the same as, or different to, the time interval between the one partial dose and the preceding partial dose. Preferably, the time interval between one partial dose and the next partial dose is the same as the time interval between the one partial dose and the preceding partial dose. That is, preferably the administration of the partial doses is regularly spaced throughout the treatment cycle. An example of such regular administration is the administration of 3 partial doses on days 1, 8, and 15 of a 3-week (i.e. 21 day) treatment cycle.

The length of the treatment cycle may vary depending upon the pharmokinetics (PK) of the CD19-ADC and the clinical requirements of the subject. The treatment cycle may be 1 week, 2 weeks, 3 weeks, 4 weeks, 5 weeks, 6 weeks, 7 weeks, 8 weeks, or 9 weeks. Preferably the treatment cycle is 3 weeks or 6 weeks, with 3 weeks being particularly preferred.

The total dose of CD19-ADC administered during the treatment cycle may vary according to the clinical requirements of the subject. For example, the total dose may be about 10, 20, 30, 40, 50, 60, 70, 80, 90, 100, 120, 150, 200, 250, 300, 350, 400, 450, 500, 550, or 600 µg/kg. In some

TABLE 3

| Regimen Day | 1 | 22 | 43 | 65 | 86 | [+21] |
|---|---|---|---|---|---|---|
| ADC dose | 150 ug/kg | 150 ug/kg | 75 ug/kg | 75 ug/kg | 75 ug/kg | [75 ug/kg] |

Fractionated Dosage Regimes

The term "fractionated dosage regime" is used herein to describe a dosage regime in which the total dose of CD19-ADC administered during the treatment cycle is administered in a series of two or more partial doses during the cases the total dose is 1 to 10 µg/kg, 11 to 20 µg/kg, 21 to 30 µg/kg, 31 to 40 µg/kg, 41 to 50 µg/kg, 51 to 60 µg/kg, 61 to 70 µg/kg, 71 to 80 µg/kg, 81 to 90 µg/kg, 91 to 100 µg/kg, 101 to 120 µg/kg, 121 to 140 µg/kg, 141 to 160 µg/kg, 161 to 180 µg/kg, 181 to 200 µg/kg, 201 to 220 µg/kg, 221 to 240

μg/kg, 241 to 260 μg/kg, 261 to 280 μg/kg, 281 to 300 μg/kg, 301 to 320 μg/kg, 321 to 340 μg/kg, 341 to 360 μg/kg, 361 to 380 μg/kg, 381 to 400 μg/kg, 401 to 420 μg/kg, 421 to 440 μg/kg, 441 to 460 μg/kg, 461 to 480 μg/kg, 481 to 500 μg/kg, 501 to 520 μg/kg, 521 to 540 μg/kg, 541 to 560 μg/kg, 561 to 580 μg/kg, or 581 to 600 μg/kg.

The size of the partial dose will depend upon the total dose of CD19-ADC administered during the treatment cycle, and the number of partial doses into which the total dose it is divided, and the relative sizes of the partial doses. In some cases each partial dose is of equal size. In some cases the partial dose is about 3, 10, 20, 30, 40, 50, 60, 70, 80, 90, 100, 110, 120, 130, 140, 150, 160, 170, 180, 190, or 200 μg/kg. In some the partial dose is 1 to 10 μg/kg, 11 to 20 μg/kg, 21 to 30 μg/kg, 31 to 40 μg/kg, 41 to 50 μg/kg, 51 to 60 μg/kg, 61 to 70 μg/kg, 71 to 80 μg/kg, 81 to 90 μg/kg, 91 to 100 μg/kg, 101 to 110 μg/kg, 111 to 120 μg/kg, 121 to 130 μg/kg, 131 to 140 μg/kg, 141 to 150 μg/kg, 151 to 160 μg/kg, 161 to 170 μg/kg, 171 to 180 μg/kg, 181 to 190 μg/kg, or 191 to 200 μg/kg.

Preferably the total dose of CD19-ADC is administered as partial doses of equal size regularly spaced throughout the treatment cycle. Administration to the subject once per week is particularly preferred. In preferred cases, each partial dose is 40 to 60 μg/kg, such as 45 to 55 μg/kg. In particularly preferred cases each partial dose is 50 μg/kg.

In some cases the total dose of CD19-ADC is administered over a three week treatment cycle in 3 equal partial doses, with a partial dose administered once a week. For example, with administration of a partial dose on days 1, 8, and 15 of a 3-week treatment cycle.

Treated Disorders

The methods of therapy described herein include those with utility for anti-cancer therapy. In particular, in certain aspects the therapies include an antibody conjugated, i.e. covalently attached by a linker, to a PBD drug moiety, i.e. toxin. When the drug is not conjugated to an antibody, the PBD drug has a cytotoxic effect. The biological activity of the PBD drug moiety is thus modulated by conjugation to an antibody. The antibody-drug conjugates (ADC) of the disclosure selectively deliver an effective dose of a cytotoxic agent to tumor tissue whereby greater selectivity, i.e. a larger therapeutic window, may be achieved.

Thus, in one aspect, the present disclosure provides a method of therapy comprising administering an ADC which binds CD19 for use in therapy, wherein the method comprises selecting a subject based on expression of CD19.

In one aspect, the present disclosure provides a packaged ADC for use in therapy, wherein the packaged ADC is supplied with a label that specifies that the therapy is suitable for use with a subject determined to be suitable for such use. The label may specify that the therapy is suitable for use in a subject has expression of CD19, that is, is CD19+.

The label may specify that the ADC is administered in a tapered and/or elongated dosage regime as described herein. The label may specify that the subject has a particular type of cancer, such as lymphoma like a B-cell Lineage Non Hodgkin Lymphoma (B-NHL), optionally wherein the lymphoma is Relapsed or Refractory. Examples of NHL lymphoma include diffuse large B-cell lymphoma (DLBCL), follicular lymphoma, (FL), Mantle Cell lymphoma (MCL), chronic lymphatic lymphoma (CLL), Waldenstroms Microglobulinemia, Burkitt's lymphoma, and Marginal Zone B-cell lymphoma (MZBL).

The label may specify that the ADC is administered in a fractionated dosage regime as described herein. The label may specify that the subject has a particular type of cancer, such as leukaemia, optionally wherein the B-ALL is Relapsed or Refractory. Examples of leukaemia include Hairy cell leukaemia (HCL), Hairy cell leukaemia variant (HCL-v), and Acute Lymphoblastic Leukaemia (ALL) such as Philadelphia chromosome-positive ALL (Ph+ALL) or Philadelphia chromosome-negative ALL (Ph-ALL).B-cell Lineage Acute Lymphoblastic Leukemias (B-ALL).

The proliferative disease treated by the methods disclosed herein may be CD19+. However as explained herein, in the practice of the disclosure, in at least some of the cells in the target location (typically a neoplasm) the antigen may be absent, or present on the cell surface at an insignificant level. For example in the target neoplasm only e.g. less than 80, 70, 60, 50, 30, 20%, 10% or 5% of the cells may be CD19 positive. In some cases where the disease is a leukaemia, such as B-ALL, CD19+ may be defined as determination of CD19 expression by ≥5% of leukemic myeloblast cells within bone marrow (aspirate or biopsy), as assessed at an approved clinical laboratory.

In some cases the CD19+ve cell is a tumour infiltrating cell. In some cases the neoplasm or neoplastic cells are, or are present in, a haematological cancer. In some cases the neoplasm or neoplastic cells are, or are present in, a solid tumor. "Solid tumor" herein will be understood to include solid haematological cancers such as lymphomas (Hodgkin's lymphoma or non-Hodgkin's lymphoma) which are discussed in more detail below.

Other solid tumors may be neoplasms, including non-haematological cancers, infiltrated with CD-19 positive cells.

In some cases the neoplasm or neoplastic cells are malignant. In some cases the neoplasm or neoplastic cells are metastatic.

The therapies described herein may be used to treat a proliferative disease. The term "proliferative disease" pertains to an unwanted or uncontrolled cellular proliferation of excessive or abnormal cells which is undesired, such as, neoplastic or hyperplastic growth, whether in vitro or in vivo.

Any type of cell may be treated, including but not limited to, lung, gastrointestinal (including, e.g. bowel, colon), breast (mammary), ovarian, prostate, liver (hepatic), kidney (renal), bladder, pancreas, brain, and skin.

It is contemplated that the therapies of the present disclosure may be used to treat various diseases or disorders, e.g. characterized by the overexpression of a tumor antigen. Exemplary conditions of hyperproliferative disorders include benign or malignant tumors; leukaemia, haematological, and lymphoid malignancies. Others include neuronal, glial, astrocytal, hypothalamic, glandular, macrophagal, epithelial, stromal, blastocoelic, inflammatory, angiogenic and immunologic, including autoimmune disorders and graft-versus-host disease (GVHD).

Generally, the disease or disorder to be treated is a hyperproliferative disease such as cancer. Examples of cancer to be treated herein include, but are not limited to, carcinoma, lymphoma, blastoma, sarcoma, and leukaemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, sarcoma, osteosarcoma, as well as head and neck cancer.

Autoimmune diseases for which the combined therapies may be used in treatment include rheumatologic disorders (such as, for example, rheumatoid arthritis, Sjögren's syndrome, scleroderma, lupus such as SLE and lupus nephritis, polymyositis/dermatomyositis, cryoglobulinemia, antiphospholipid antibody syndrome, and psoriatic arthritis), osteoarthritis, autoimmune gastrointestinal and liver disorders (such as, for example, inflammatory bowel diseases (e.g. ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteriitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, graft-versus-host disease (GVHD), and autoimmune endocrine disorders (such as, for example, diabetic-related autoimmune diseases such as insulin-dependent diabetes mellitus (IDDM), Addison's disease, and autoimmune thyroid disease (e.g. Graves' disease and thyroiditis)). More preferred such diseases include, for example, rheumatoid arthritis, ulcerative colitis, ANCA-associated vasculitis, lupus, multiple sclerosis, Sjögren's syndrome, Graves' disease, IDDM, pernicious anemia, thyroiditis, and glomerulonephritis.

Proliferative disorders of particular interest include, but are not limited to, non-Hodgkin's Lymphoma, including diffuse large B-cell lymphoma (DLBCL), follicular lymphoma, (FL), Burkitt's lymphoma (BL), Mantle Cell lymphoma (MCL), chronic lymphatic lymphoma (CLL), Waldenstroms Microglobulinemia, Burkitt's lymphoma, and Marginal Zone B-cell lymphoma (MZBL), and leukemias such as Hairy cell leukaemia (HCL), Hairy cell leukaemia variant (HCL-v), and Acute Lymphoblastic Leukaemia (ALL) such as Philadelphia chromosome-positive ALL (Ph+ALL) or Philadelphia chromosome-negative ALL (Ph-ALL). [Fielding A., Haematologica. 2010 January; 95(1): 8-12].

In certain aspects, the subject has diffuse large B cell lymphoma or peripheral T cell lymphoma, including the anaplastic large cell lymphoma and angioimmunoblastic T cell lymphoma subtypes.

The disease may be resistant, relapsed or refractory. As used herein, relapsed disease constitutes conditions in which a previously treated tumor which became undetectable by conventional imaging technology again becomes detectable; refractory disease a condition in which the cancer—despite anti-tumor therapy—continues to grow.

Preferably, the tapered and/or elongated dosage regimes described here are employed when the proliferative disease is lymphoma. For example, the proliferative disease may be non-Hodgkin's Lymphoma, such as diffuse large B-cell lymphoma (DLBCL), follicular lymphoma, (FL), Mantle Cell lymphoma (MCL), chronic lymphatic lymphoma (CLL), Waldenstroms Microglobulinemia, Burkitt's lymphoma, and Marginal Zone B-cell lymphoma (MZBL). In some cases the proliferative disease is Relapsed or Refractory B-cell Lineage Non Hodgkin Lymphoma (B-NHL).

Preferably, the fractionated dosage regimes described here are employed when the proliferative disease is leukaemia, such as Hairy cell leukaemia (HCL), Hairy cell leukaemia variant (HCL-v), and Acute Lymphoblastic Leukaemia (ALL) such as Philadelphia chromosome-positive ALL (Ph+ALL) or Philadelphia chromosome-negative ALL (Ph-ALL). In some cases the proliferative disease is Relapsed or Refractory B-cell Lineage Acute Lymphoblastic Leukemias (B-ALL). In some cases the proliferative disease is CD19+ Acute Lymphoblastic Leukemias.

Reduced Toxicity and Improved Efficacy
Lymphoma

The present disclosure provides a method of reducing the toxicity and/or side effects associated with administration of a CD19-ADC to a subject, the method comprising administering the CD19-ADC in a tapered and/or elongated dosage regime as defined herein.

In some cases the reduction in toxicity is measured relative to a dosage regime having constant dosage level and cycle length. The dosage level and cycle length of the constant comparator may be the same as the starting dose and starting length of the tapered and/or elongated regime.

In some cases the level of toxicity is measured as the incidence of Treatment Emergent Adverse Events (TEAE) occurring after one treatment cycle at a given total dose of CD19-ADC. A treatment-emergent AE (TEAE) is defined as any event not present before exposure to the CD19-ADC or any event already present that worsens in either intensity or frequency after exposure to the CD19-ADC. The incidence of AE with the tapered and/or elongated dosage regime may be no more that 95%, such as no more than 90%, no more than 80%, no more than 70%, no more than 60%, no more than 50%, no more than 40%, no more than 30%, no more than 20%, no more than 10%, or no more than 5% of the incidence of AE in the corresponding constant dose level and cycle length regime. Adverse events will be graded according to CTCAE Version 4.0 (v4.03, published Jun. 14, 2010; NIH Publication No. 09-5410).

For example, if a single treatment cycle of a single-dose regime in 100 subjects leads to 10 AEs and a single treatment cycle the corresponding tapered and/or elongated regime leads to 5 AEs, the incidence of AEs with the tapered and/or elongated regime is 50% of the incidence of AE in the corresponding constant dose level and cycle length regime.

In some cases the level of toxicity is measured as the incidence of Serious Adverse Events (SAE) occurring after one treatment cycle at a given total dose of CD19-ADC. A serious adverse event (SAE) is defined as any event that results in death, is immediately life-threatening, requires inpatient hospitalization or prolongation of existing hospitalization, results in persistent or significant disability/incapacity, or is a congenital anomaly/birth defect. Hospitalization for elective procedures or for protocol compliance is not considered an SAE. Important medical events that may not result in death, be life-threatening, or require hospitalization may be considered SAEs when, based upon appropriate medical judgment, they may jeopardize the patient or may require medical or surgical intervention to prevent 1 of the outcomes listed in this definition. Examples of such medical events include allergic bronchospasm requiring intensive treatment in an emergency room or at home, blood dyscrasias or convulsions that do not result in inpatient hospitalization, or the development of drug dependency or drug abuse. The incidence of SAE with the tapered and/or elongated dosage regime may be no more that 95%, such as no more than 90%, no more than 80%, no more than 70%, no more than 60%, no more than 50%, no more than 40%, no more than 30%, no more than 20%, no more than 10%, or no more than 5% of the incidence of SAE in the corresponding constant dose level and cycle length regime. Adverse events will be graded according to CTCAE Version 4.0 (v4.03, published Jun. 14, 2010; NIH Publication No. 09-5410).

In some cases the level of toxicity is measured as the incidence of Dose Limiting Toxicity (DLT) occurring after one treatment cycle at a given total dose of CD19-ADC. The incidence of DLT with the tapered and/or elongated dosage regime may be no more that 95%, such as no more than 90%, no more than 80%, no more than 70%, no more than 60%, no more than 50%, no more than 40%, no more than 30%, no more than 20%, no more than 10%, or no more than 5% of the incidence of DLT in the corresponding constant dose level and cycle length regime.

For example, if a single treatment cycle of a single-dose regime in 100 subjects leads to 10 DLTs and a single treatment cycle of the corresponding tapered and/or elongated regime leads to 5 DLTs, the incidence of DLTs with the tapered and/or elongated regime is 50% of the incidence of DLT in the corresponding constant dose level and cycle length regime.

A DLT as used herein is defined as any of the following events, except those that are clearly due to underlying disease or extraneous causes:
  A hematologic DLT is defined as:
    Grade 3 or 4 febrile neutropenia or neutropenic infection.
    Grade 4 neutropenia lasting >7 days.
    Grade 4 thrombocytopenia.
    Grade 3 thrombocytopenia with clinically significant bleeding, or Grade 3 thrombocytopenia requiring a platelet transfusion
    Grade 4 anemia.
  A non-hematologic DLT is defined as:
    Grade 4 tumor lysis syndrome (Grade 3 TLS will not constitute DLT unless it leads to irreversible end-organ damage).
    Grade 3 or higher AE (including nausea, vomiting, diarrhoea, and electrolyte imbalances lasting more than 48 hours despite optimal therapy; excluding all grade of alopecia).
    Grade 3 or higher hypersensitivity reaction (regardless of premedication).
    Grade 2 or higher skin ulceration.

The above adverse events will be graded according to CTCAE Version 4.0 (v4.03, published Jun. 14, 2010; NIH Publication No. 09-5410).

The present disclosure also provides a method of increasing the treatment efficacy associated with administration of a CD19-ADC to a subject, the method comprising administering the CD19-ADC in a tapered and/or elongated dosage regime as defined herein.

In some cases the increase in efficacy is measured relative to a dosage regime having constant dosage level and cycle length. The dosage level and cycle length of the constant comparator may be the same as the starting dose and starting length of the tapered and/or elongated regime.

In some cases the level of efficacy is measured as the proportion of subjects achieving at least stable disease [SD] after one treatment cycle at a given total dose of ADC (i.e the proportion of subjects achieving either stable disease [SD], a partial response [PR], or a complete response [CR]. The proportion of subjects achieving at least SD may be at least 110%, such as at least 120%, at least 130%, at least 140%, at least 150%, at least 160%, at least 170%, at least 180%, at least 190%, or at least 200%, of the proportion of subjects achieving at least stable disease [SD] in the corresponding constant dose level and cycle length regime.

For example, if a single-dose regime in 100 subjects leads to at least SD in 50 subjects and the corresponding tapered and/or elongated regime leads to at least SD in 80 subjects, the proportion of subjects achieving at least SD with the tapered and/or elongated regime is 160% of the proportion of subjects achieving at least a partial response [SD] in the corresponding constant dose level and cycle length regime.

Assessment of response to treatment with ADC may be based on bone marrow samples (aspirate or biopsy if aspirate unattainable) taken toward the end of each treatment cycle. For example, on day 19±3 days in a 21-day treatment cycle. The subject's response to ADC may be categorised as CR, PR, SD, or PD according to the 2014 Lugano Classification Criteria (using the New "Cheson" Criteria), in which:
  Complete response (CR) is defined as achieving each of the following:
    Nodal Disease <1.5 cm in LDi
    Extranodal Disease: Absent
    Spleen: regress to normal
    No new lesions
    Bone marrow: Normal by morphology; if indeterminate, IHC negative
  Partial response (PR) is defined as achieving each of the following:
    Nodal Disease >=50% decrease from baseline in SPD of all target lesions
    No increase in non-target
    Spleen: >50% decrease from baseline in enlarged portion of spleen (value >13 cm)
    No new lesions
  Stable Disease (SD) is defined as achieving each of the following:
    Nodal Disease <50% decrease from baseline in SPD of all target lesions
    No criteria for nodal PD are met
    No progression in non-target
    No progression in spleen enlargement
    No new lesions
Nodal PD criteria:
  An individual node/lesion must be abnormal with:
  LDi>1.5 cm AND
  Increase by >=50% from PPD nadir AND
  An increase in LDi or SDi from nadir
    ≥0.5 cm for lesions ≤2 cm
    ≥1.0 cm for lesions >2 cm
Leukaemia The present disclosure provides a method of reducing the toxicity and/or side effects associated with administration of a CD19-ADC to a subject, the method comprising administering the CD19-ADC in a fractionated dosage regime as defined herein.

In some cases the reduction in toxicity is measured relative to a single-dose dosage regime having the same total dose administered and length of treatment cycle. In such a single dose regime, the total dose of CD19-ADC is administered as a single dose at the start of the treatment cycle.

In some cases the level of toxicity is measured as the incidence of Treatment Emergent Adverse Events (TEAE) occurring after one treatment cycle at a given total dose of CD19-ADC. A treatment-emergent AE (TEAE) is defined as any event not present before exposure to the CD19-ADC or any event already present that worsens in either intensity or frequency after exposure to the CD19-ADC. The incidence of AE with the fractionated dosage regime may be no more that 95%, such as no more than 90%, no more than 80%, no more than 70%, no more than 60%, no more than 50%, no more than 40%, no more than 30%, no more than 20%, no more than 10%, or no more than 5% of the incidence of AE in the corresponding single dose regime. Adverse events will be graded according to CTCAE Version 4.0 (v4.03, published Jun. 14, 2010; NIH Publication No. 09-5410).

For example, if a single treatment cycle of a single-dose regime in 100 subjects leads to 10 AEs and a single treatment cycle the corresponding fractionated regime leads to 5 AEs, the incidence of AEs with the fractionated regime is 50% of the incidence of AE in the corresponding single dose regime.

In some cases the level of toxicity is measured as the incidence of Serious Adverse Events (SAE) occurring after one treatment cycle at a given total dose of CD19-ADC. A serious adverse event (SAE) is defined as any event that results in death, is immediately life-threatening, requires inpatient hospitalization or prolongation of existing hospitalization, results in persistent or significant disability/incapacity, or is a congenital anomaly/birth defect. Hospitalization for elective procedures or for protocol compliance is not considered an SAE. Important medical events that may not result in death, be life-threatening, or require hospitalization may be considered SAEs when, based upon appropriate medical judgment, they may jeopardize the patient or may require medical or surgical intervention to prevent one of the outcomes listed in this definition. Examples of such medical events include allergic bronchospasm requiring intensive treatment in an emergency room or at home, blood dyscrasias or convulsions that do not result in inpatient hospitalization, or the development of drug dependency or drug abuse. The incidence of SAE with the fractionated dosage regime may be no more that 95%, such as no more than 90%, no more than 80%, no more than 70%, no more than 60%, no more than 50%, no more than 40%, no more than 30%, no more than 20%, no more than 10%, or no more than 5% of the incidence of SAE in the corresponding single dose regime. Adverse events will be graded according to CTCAE Version 4.0 (v4.03, published Jun. 14, 2010; NIH Publication No. 09-5410).

In some cases the level of toxicity is measured as the incidence of Dose Limiting Toxicity (DLT) occurring after one treatment cycle at a given total dose of CD19-ADC. The incidence of DLT with the fractionated dosage regime may be no more that 95%, such as no more than 90%, no more than 80%, no more than 70%, no more than 60%, no more than 50%, no more than 40%, no more than 30%, no more than 20%, no more than 10%, or no more than 5% of the incidence of DLT in the corresponding single dose regime.

For example, if a single treatment cycle of a single-dose regime in 100 subjects leads to 10 DLTs and a single treatment cycle of the corresponding fractionated regime leads to 5 DLTs, the incidence of DLTs with the fractionated regime is 50% of the incidence of DLT in the corresponding single dose regime.

A DLT as used herein is defined as any of the following events, except those that are clearly due to underlying disease or extraneous causes:
A hematologic DLT is defined as:
Grade 3 or higher event of neutropenia or thrombocytopenia, or a Grade 4 anemia, with a hypocellular bone marrow lasting for 6 weeks or more after the start of a cycle, in the absence of residual leukaemia (i.e., with <5% myeloblasts). In case of a normocellular bone marrow with <5% myeloblasts, 8 weeks with Grade 3 pancytopenia will be considered a DLT.
A non-hematologic DLT is defined as:
Grade 4 tumor lysis syndrome (Grade 3 TLS will not constitute DLT unless it leads to irreversible end-organ damage).
Grade 3 or higher AE (including nausea, vomiting, diarrhoea, and electrolyte imbalances lasting more than 48 hours despite optimal therapy; excluding all grades of alopecia).
CTCAE Grade 3 or higher hypersensitivity reaction (regardless of premedication).
CTCAE Grade 3 or higher skin ulceration.
The above adverse events will be graded according to CTCAE Version 4.0 (v4.03, published Jun. 14, 2010; NIH Publication No. 09-5410).

The present disclosure also provides a method of increasing the treatment efficacy associated with administration of a CD19-ADC to a subject, the method comprising administering the CD19-ADC in a fractionated dosage regime as defined herein.

In some cases the increase in efficacy is measured relative to a single-dose dosage regime having the same total dose administered and length of treatment cycle. In such a single dose regime, the total dose of ADC is administered as a single dose at the start of the treatment cycle.

In some cases the level of efficacy is measured as the proportion of subjects achieving at least a partial response [PR] after one treatment cycle at a given total dose of ADC (i.e the proportion of subjects achieving either a partial response [PR], a complete response with incomplete blood count recovery [CRi], or a complete response [CR]. The proportion of subjects achieving at least PR may be at least 110%, such as at least 120%, at least 130%, at least 140%, at least 150%, at least 160%, at least 170%, at least 180%, at least 190%, or at least 200%, of the proportion of subjects achieving at least a partial response [PR] in the corresponding single dose regime.

For example, if a single-dose regime in 100 subjects leads to at least PR in 50 subjects and the corresponding fractionated regime leads to at least PR in 80 subjects, the proportion of subjects achieving at least PR with the fractionated regime is 160% of the proportion of subjects achieving at least a partial response [PR] in the corresponding single dose regime.

Assessment of response to treatment with ADC may be based on bone marrow samples (aspirate or biopsy if aspirate unattainable) taken toward the end of each treatment cycle. Assessment of response to treatment with ADC may be based on bone marrow samples (aspirate or biopsy if aspirate unattainable) taken toward the end of selected treatment cycles, for example, every other treatment cycle. For example, on day 19±3 days in a 21-day treatment cycle. The subject's response to ADC may be categorised as CR, CRi, PR, PD or NR according to the following criteria:
Complete response (CR) is defined as achieving each of the following:
Bone marrow differential showing ≤5% blast cells,
Absolute neutrophil count ≥1.0×109/L and platelet count ≥100×109/L, Absence of extra-medullary disease,
Patient is independent of red blood cell (RBC) transfusions.
Complete response with incomplete blood count recovery (CRi) is defined as achieving all CR criteria except that values for ANC may be <1.0×10$^9$/L and/or values for platelets may be <100×10$^9$/L.
Partial response (PR) is defined as achieving each of the following:
ANC≥1.0×109/L and platelet count ≥100×109/L
Bone marrow differential showing a ≥50% decrease from baseline in the percentage of bone marrow blast cells to a level >5% and ≤25%.
No response is defined as not achieving CR, CRi, or PR
PD is defined as:
For patients with CR or CRi, the first date of reappearance of blast cells in bone marrow and/or peripheral blood to a level ≥5%, or development of extramedullary disease.
For patients with PR, the first date of an increase in blast cells in bone marrow and/or peripheral blood such that the patient does not continue to meet the criteria for PR.

Patient Selection

In certain cases, the subjects are selected as suitable for treatment with either, (a) the tapered and/or elongated dosage regime, or (b) the fractionated dosage regime, before the treatment is administered.

Preferably, subjects are selected for treatment with the tapered and/or elongated dosage regimes described if they have, are suspected of having, or have been diagnosed with lymphoma. For example, the lymphoma may be non-Hodgkin's Lymphoma, such as diffuse large B-cell lymphoma (DLBCL), follicular lymphoma, (FL), Mantle Cell lymphoma (MCL), chronic lymphatic lymphoma (CLL), Waldenstroms Microglobulinemia, Burkitt's lymphoma, and Marginal Zone B-cell lymphoma (MZBL).

Preferably, subjects are selected for treatment with the fractionated dosage regimes described if they have, are suspected of having, or have been diagnosed with leukaemia, For example, the leukaemia may be Hairy cell leukaemia (HCL), Hairy cell leukaemia variant (HCL-v), and Acute Lymphoblastic Leukaemia (ALL) such as Philadelphia chromosome-positive ALL (Ph+ALL) or Philadelphia chromosome-negative ALL (Ph-ALL).

As used herein, subjects who are considered suitable for treatment are those subjects who are expected to benefit from, or respond to, the treatment. Subjects may have, or be suspected of having, or be at risk of having cancer. Subjects may have received a diagnosis of cancer. In particular, subjects may have, or be suspected of having, or be at risk of having, lymphoma or leukaemia. In some cases, subjects may have, or be suspected of having, or be at risk of having, a solid cancer that has tumour associated non-tumor cells that express a CD19, such as infiltrating cells that express CD19.

In some cases, subjects are selected on the basis of the amount or pattern of expression of CD19. In some cases, the selection is based on expression of CD19 at the cell surface.

In some cases, expression of CD19 in a particular tissue of interest is determined. For example, in a sample of lymphoid tissue or tumor tissue. In some cases, systemic expression of CD19 is determined. For example, in a sample of circulating fluid such as blood, plasma, serum or lymph.

In some cases, the subject is selected as suitable for treatment due to the presence of CD19 expression in a sample. In those cases, subjects without CD19 expression may be considered not suitable for treatment.

In other cases, the level of CD19 expression is used to select a subject as suitable for treatment. Where the level of expression of CD19 is above a threshold level, the subject is determined to be suitable for treatment.

In some cases, the presence of CD19+ in cells in the sample indicates that the subject is suitable for treatment with a combination comprising an ADC. In other cases, the amount of CD19 expression must be above a threshold level to indicate that the subject is suitable for treatment. In some cases, the observation that CD19 localisation is altered in the sample as compared to a control indicates that the subject is suitable for treatment.

In some cases, a subject is indicated as suitable for treatment if cells obtained from lymph node or extra nodal sites react with antibodies against CD19 as determined by IHC.

In some cases, a patient is determined to be suitable for treatment if at least 5%, 10%, 15%, 20%, 25%, 30%, 35%, 40%, 45%, 50%, 55%, 60%, 65%, 70%, 75%, 80%, 85%, 90% or more of all cells in the sample express CD19. In some cases disclosed herein, a patient is determined to be suitable for treatment if at least at least 5% of the cells in the sample express CD19.

In some cases, a patient is determined to be suitable for treatment if they have had a DLT in a previous single-dose treatment cycle with the ADC.

In some cases, a patient is determined to be suitable for treatment if they are have exhibited any sign of ADC-induced toxicity in a previous single-dose treatment cycle with the ADC.

In some cases, a patient is determined to be suitable for if they have increased sensitivity to ADC-induced toxicity.

In some cases, a patient is determined to be suitable for treatment if their disease is relapsed or refractory.

In some cases, a subject undergoes a neurological examination prior to treatment with the ADC. Preferably the neurological examination includes tests of strength, sensation, and deep-tendon reflexes.

In some cases, a subject is determined to be not suitable for treatment with the ADC if they have, or have recently had, a neurologic disorder. Examples of such disorders include poliomyelitis and multiple sclerosis Generally, neurological disorders that are explained by the subject's previous medical history and known not to be related to, or a risk factor for, to treatment with ADC do not render a subject unsuitable for treatment with the ADC. An example of such a disorder is a left-sided weakness known to be a result of a previous cerebral vascular accident, such as a stroke.

The neurologic disorder, as discussed herein, may be polyradiculopathy (including acute inflammatory demyelinating polyradiculoneuropathy (AIDP)), Guillain-Barré syndrome (GBS), myasthenia gravis, or neurologic disorder that is linked to or is an early indicator of polyradiculitis, GBS, or myasthenia gravis (e.g. ascending (bilateral) sensory loss and/or motor weakness).

In some cases, a subject undergoes a neurological examination after administration of the ADC. In some cases the results of the neurological examination of a subject after administration of the ADC are compared to the results from before administration of the ADC in order to assess any change in the tested neurological parameters. In some cases, treatment with the ADC is reduced, suspended, or permanently discontinued if the subject experiences a neurologic toxicity.

The neurologic toxicity, as discussed herein, may be polyradiculopathy (including acute inflammatory demyelinating polyradiculoneuropathy (AIDP)), Guillain-Barré syndrome (GBS), myasthenia gravis, or neurologic disorder that is linked to or is an early indicator of polyradiculitis, GBS, or myasthenia gravis (e.g. ascending (bilateral) sensory loss and/or motor weakness).

In some cases, a subject undergoes a neurological examination after each administration of the ADC. In some cases the results of the neurological examination of a subject after each administration of the ADC are compared to the results from before the most recent administration of the ADC in order to assess any change in the tested neurological parameters. In some cases the results of the neurological examination of a subject after each administration of the ADC are compared to the results from before the first administration of the ADC in order to assess any change in the tested neurological parameters.

In some cases, a subject undergoes a neurological examination if they experience a neurologic toxicity following administration of the ADC.

In some cases, treatment with the ADC is reduced, suspended, or permanently discontinued if the subject has a neurological disorder or experiences a neurologic toxicity. For example, if a subject experiences ≥grade 1 neurologic toxicity, such as a grade 1 neurologic toxicity that is linked to or is an early indicator of polyradiculitis (e.g. ascending (bilateral) sensory loss and/or motor weakness) treatment with the ADC may be reduced or suspended. In some case, if the subject experiences a ≥grade 2 neurologic toxicity (e.g. grade 2 polyradiculitis or GBS), treatment with the ADC may be permanently discontinued.

Adverse events will be graded according to CTCAE Version 4.0 (v4.03, published Jun. 14, 2010; NIH Publication No. 09-5410).

In some cases, treatment with the ADC is reduced by reducing the dose of ADC that is administered to the subject in each subsequent treatment cycle. In some cases, treatment with the ADC is reduced by increasing the length of each subsequent treatment cycle for example, from a 3 week cycle to a 6 week cycle). In some cases, treatment with the ADC is reduced by reducing the dose of ADC that is administered to the subject in each subsequent treatments cycle and increasing the length of each subsequent treatment.

In some cases, treatment with the ADC is suspended by stopping treatment with the ADC until the toxicity is resolved. In some cases, treatment with the ADC is resumed after resolution of the toxicity to baseline. The subject may be monitored weekly until the neurologic toxicity is resolved. In some cases the treatment is suspended for up to 3 weeks (21 days).

For example, in some cases a subject undergoes a neurological examination if they experience grade 1 neurologic toxicity, such as a grade 1 neurologic toxicity that is linked to or is an early indicator of polyradiculitis (e.g. ascending (bilateral) sensory loss and/or motor weakness). In some cases, if a subject experiences a ≥grade 1 neurologic toxicity (e.g. grade 1 polyradiculitis or GBS), treatment with the ADC is resumed after resolution of the toxicity to baseline. The subject may be monitored weekly until the neurologic toxicity is resolved.

In some cases, if a subject experiences a ≥grade 2 neurologic toxicity (e.g. grade 2 polyradiculitis or GBS), treatment with the ADC is permanently discontinued.

In some cases, a subject is determined to be not suitable for treatment with the ADC if they have, have recently had, or historically had, an infection caused by a pathogen that may be associated with neurologic and/or immune-related disease. Examples of such pathogens include HSV1, HSV2, VZV, EBV, CMV, measles, Influenza A, Zika virus, Chikungunya virus, *Mycoplasma pneumonia, Campylobacter jejuni*, or enterovirus D68.

In some cases, treatment with the ADC is reduced, suspended, or permanently discontinued if the subject experiences has, or acquires, an infection caused by a pathogen that may be associated with neurologic and/or immune-related disease. Examples of such pathogens include HSV1, HSV2, VZV, EBV, CMV, measles, Influenza A, Zika virus, Chikungunya virus, *Mycoplasma* pneumonia, *Campylobacter jejuni*, or enterovirus D68. In some cases, treatment with the ADC is suspended until at least 4 weeks after symptoms of the infection are resolved.

Examples of immune-related diseases include rheumatoid arthritis, systemic progressive sclerosis [scleroderma], systemic lupus erythematosus, Sjögren's syndrome, autoimmune vasculitis [e.g., Wegener's granulomatosis].

In some cases, treatment with the ADC is reduced, suspended, or permanently discontinued if the subject experiences any grade 1 autoimmune toxicities (e.g. endocrinopathies).

Samples

The sample may comprise or may be derived from: a quantity of blood; a quantity of serum derived from the subject's blood which may comprise the fluid portion of the blood obtained after removal of the fibrin clot and blood cells; a quantity of pancreatic juice or fluid from a spinal tap; a tissue sample or biopsy; or cells isolated from said subject.

A sample may be taken from any tissue or bodily fluid. In certain cases, the sample may include or may be derived from a tissue sample, biopsy, resection or isolated cells from said subject.

In certain cases, the sample is a tissue sample. The sample may be a sample of tumor tissue, such as cancerous tumor tissue. The sample may have been obtained by a tumor biopsy. In some cases, the sample is a lymphoid tissue sample, such as a lymphoid lesion sample or lymph node biopsy. In some cases, the sample is a skin biopsy.

In some cases the sample is taken from a bodily fluid, more preferably one that circulates through the body. Accordingly, the sample may be a blood sample or lymph sample. In some cases, the sample is a urine sample or a saliva sample.

In some cases, the sample is a blood sample or blood-derived sample. The blood derived sample may be a selected fraction of a subject's blood, e.g. a selected cell-containing fraction or a plasma or serum fraction.

A selected cell-containing fraction may contain cell types of interest which may include white blood cells (WBC), particularly peripheral blood mononuclear cells (PBC) and/or granulocytes, and/or red blood cells (RBC). Accordingly, methods according to the present disclosure may involve detection of a CD19 polypeptide or nucleic acid in the blood, in white blood cells, peripheral blood mononuclear cells, granulocytes and/or red blood cells.

The sample may be fresh or archival. For example, archival tissue may be from the first diagnosis of a subject, or a biopsy at a relapse. In certain cases, the sample is a fresh biopsy.

Subject Status

The subject may be an animal, mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject may be any of its forms of development, for example, a foetus. In one preferred embodiment, the subject is a human. The terms "subject", "patient" and "individual" are used interchangeably herein.

In some cases disclosed herein, a subject has, or is suspected as having, or has been identified as being at risk of, cancer. In some cases disclosed herein, the subject has already received a diagnosis of cancer.

The subject may have, be suspected of having, been identified as being at risk of, or received a diagnosis of lymphoma like non-Hodgkin's Lymphoma, including diffuse large B-cell lymphoma (DLBCL), follicular lymphoma, (FL), Mantle Cell lymphoma (MCL), chronic lymphatic lymphoma (CLL), Waldenstroms Microglobulinemia, Burkitt's lymphoma, and Marginal Zone B-cell lymphoma (MZBL). Such subjects are preferably treated with a tapered and/or elongated dosage regime as disclosed herein.

The subject may have, be suspected of having, been identified as being at risk of, or received a diagnosis of leukaemia, such as Hairy cell leukaemia (HCL), Hairy cell leukaemia variant (HCL-v), and Acute Lymphoblastic Leukaemia (ALL) such as Philadelphia chromosome-positive ALL (Ph+ALL) or Philadelphia chromosome-negative ALL (Ph-ALL). [Fielding A., Haematologica. 2010 January; 95(1): 8-12]. Such subjects are preferably treated with a fractionated dosage regime as disclosed herein.

In some cases, the subject has received a diagnosis of a solid cancer containing CD19+ expressing infiltrating T-cells.

The Subject may be undergoing, or have undergone, a therapeutic treatment for that cancer. The subject may, or may not, have previously received ADCx19. In some cases the cancer is leukemia or lymphoma, including non-Hodgkin's lymphoma.

Controls

In some cases, CD19 expression in the subject is compared to target expression in a control. Controls are useful to support the validity of staining, and to identify experimental artefacts.

In some cases, the control may be a reference sample or reference dataset. The reference may be a sample that has been previously obtained from a subject with a known degree of suitability. The reference may be a dataset obtained from analyzing a reference sample.

Controls may be positive controls in which the target molecule is known to be present, or expressed at high level, or negative controls in which the target molecule is known to be absent or expressed at low level.

Controls may be samples of tissue that are from subjects who are known to benefit from the treatment. The tissue may be of the same type as the sample being tested. For example, a sample of tumor tissue from a subject may be compared to a control sample of tumor tissue from a subject who is known to be suitable for the treatment, such as a subject who has previously responded to the treatment.

In some cases the control may be a sample obtained from the same subject as the test sample, but from a tissue known to be healthy. Thus, a sample of cancerous tissue from a subject may be compared to a non-cancerous tissue sample.

In some cases, the control is a cell culture sample.

In some cases, a test sample is analyzed prior to incubation with an antibody to determine the level of background staining inherent to that sample.

In some cases an isotype control is used. Isotype controls use an antibody of the same class as the target specific antibody, but are not immunoreactive with the sample. Such controls are useful for distinguishing non-specific interactions of the target specific antibody.

The methods may include hematopathologist interpretation of morphology and immunohistochemistry, to ensure accurate interpretation of test results. The method may involve confirmation that the pattern of expression correlates with the expected pattern. For example, where the amount of CD19 expression is analyzed, the method may involve confirmation that in the test sample the expression is observed as membrane staining, with a cytoplasmic component. The method may involve confirmation that the ratio of target signal to noise is above a threshold level, thereby allowing clear discrimination between specific and non-specific background signals.

Methods of Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

The term "therapeutically-effective amount" or "effective amount" as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen. Generally, when a method of treatment describes the use of an ADC, it is intended that the ADC is used in a therapeutically-effective amount.

The actual amount administered, and rate and time-course of administration, will depend on the nature and severity of what is being treated. Prescription of treatment, e.g. decisions on dosage, is within the responsibility of general practitioners and other medical doctors. The subject may have been tested to determine their eligibility to receive the treatment according to the methods disclosed herein. The method of treatment may comprise a step of determining whether a subject is eligible for treatment, using a method disclosed herein.

Similarly, the term "prophylactically-effective amount," as used herein, pertains to that amount of an active compound, or a material, composition or dosage from comprising an active compound, which is effective for producing some desired prophylactic effect, commensurate with a reasonable benefit/risk ratio, when administered in accordance with a desired treatment regimen.

Disclosed herein are methods of therapy. Also provided is a method of treatment, comprising administering to a subject in need of treatment a therapeutically-effective amount of an ADC in a tapered and/or elongated dosage regime.

The ADC may comprise an anti-CD19 antibody. The anti-CD19 antibody may be RB4v1.2 antibody. The ADC may comprise a drug which is a PBD dimer. The ADC may be an anti-CD19-ADC, and in particular, ADCX19. The ADC may be an ADC disclosed in WO2014/057117.

The treatment may involve administration of the ADC alone or in further combination with other treatments, either simultaneously or sequentially dependent upon the condition to be treated. In sequential administration, for some cases the ADC is administered before the other treatment; for other cases the ADC is administered after the other treatment. Examples of treatments and therapies include, but are not limited to, chemotherapy (the administration of active agents, including, e.g. drugs, such as chemotherapeutics); immunotherapy; surgery; and radiation therapy.

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy", Immuno-oncology drugs such as checkpoint inhibitors, and conventional chemotherapy.

Examples of chemotherapeutic agents include: Lenalidomide (REVLIMID®, Celgene), Vorinostat (ZOLINZA®, Merck), Panobinostat (FARYDAK®, Novartis), Mocetinostat (MGCD0103), Everolimus (ZORTRESS®, CERTICAN®, Novartis), Bendamustine (TREAKISYM®, RIBOMUSTIN®, LEVACT®, TREANDA®, Mundipharma International), erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g. calicheamicin, calicheamicin gamma1I, calicheamicin omega1 (*Angew Chem. Intl. Ed. Engl.* (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone;

vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above. Combinations of agents may be used, such as CHP (doxorubicin, prednisone, cyclophosphamide), or CHOP (doxorubicin, prednisone, cyclophopsphamide, vincristine).

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), ofatumumab (ARZERRA®, GSK), pertuzumab (PERJETA™, OMNITARG™, 2C4, Genentech), trastuzumab (HERCEPTIN®, Genentech), tositumomab (Bexxar, Corixia), MDX-060 (Medarex) and the antibody drug conjugate, gemtuzumab ozogamicin (MYLOTARG®, Wyeth).

Humanized monoclonal antibodies with therapeutic potential as chemotherapeutic agents in combination with the conjugates of the disclosure include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, nivolumab, pembrolizumab, durvalumab, and visilizumab.

In some cases in particular, the ADC is administered to subjects in combination with a steroid, Ibrutnib, Durvulamab, rituximab, and/or cytarabine.

Combination with Steroids

In developing the ADC dosage regimes described herein, it was observed that administration of steroids such as dexamethasone reduced the frequency and/or severity of toxicity symptom reported by subjects.

Accordingly, in preferred embodiments the ADC is administered in combination with a steroid, such as dexamethasone.

Preferably, the steroid is dexamethasone. Other suitable steroid are found in the classes of corticosteroids, such as glucocorticoids. Example glucocorticoids are Cortisol (hydrocortisone), Cortisone, Prednisone, Prednisolone, Methylprednisolone, Dexamethasone, Betamethasone, Triamcinolone, Fludrocortisone acetate, and Deoxycorticosterone acetate.

Specifically envisaged are embodiments where the CD19-ADC is administered in combination with a steroid, such as dexamethasone. Preferably the first dose of the steroid is given before the CD19-ADC is administered, for example at least 2 hours before the ADC is administered. A further dose of steroid such as dexamethasone may be administered to the subject the day after the ADC is administered. Optionally, a yet further dose of steroid such as dexamethasone may be administered to the subject the day before the ADC is administered.

The steroid may be administered before the ADC is administered, for example at least 2 hours, at least 6 hours, at least 12 hours, or the day before the ADC is administered.

In some embodiments, a first dose of steroid is administered the day before the ADC is administered. A second dose of steroid may then be administered on the day the ADC is administered, preferably before the ADC is administered, such as at least 2 hours before the ADC is administered. A third dose of steroid may then be administered on the day after the ADC is administered. In dosing regimes comprising more than one administration of ADC per treatment cycle (e.g. fractionated dosage regimes), the steroid is preferably administered only in conjunction with the first administration of ADC in each treatment cycle.

In some embodiments, a first dose of steroid is administered the day the ADC is administered, preferably before the ADC is administered, such as at least 2 hours before the ADC is administered. A second dose of steroid may then be administered on the day after the ADC is administered. In dosing regimes comprising more than one administration of ADC per treatment cycle (e.g. fractionated dosage regimes), the steroid is preferably administered only in conjunction with the first administration of ADC in each treatment cycle.

The steroid may be administered in any method known in the art, such as orally, parenterally (e.g. injection intravenously, intramuscularly, or intrathecally), inhalation, or topically. Preferably the steroid is administered orally.

The steroid may be administered in a range of dosage regimes. For example, the dose of steroid to be administered in a day may be administered as a single dose, two partial doses, three partial doses, or more than three partial doses. Preferably partial doses are of equal size. Preferably, the dose of steroid to be administered in a day is administered as two equal, partial doses.

Each dose of steroid may be 1 mg, 2 mg, 3 mg, 4 mg, 5 mg, 6 mg, 7 mg, 8 mg, 9 mg, 10 mg, 11 mg, 12 mg, 14 mg, 16 mg, 18 mg, 20 mg, 22 mg, 24 mg, 26 mg, 28 mg, or 30 mg.

Each partial dose of steroid may be 1 mg, 2 mg, 3 mg, 4 mg, 5 mg, 6 mg, 7 mg, 8 mg, 9 mg, 10 mg, 11 mg, 12 mg, 13 mg, 14 mg, or 15 mg.

In some embodiments Dexamethasone is administered orally as 4 mg twice daily: (i) the day before ADC administration, (ii) the day of ADC administration, and (iii) the day after ADC administration. The steroid is administered in conjunction with the ADC administered on Week 1, Day 1 of each cycle only, regardless of ADC treatment schedule.

In some embodiments Dexamethasone is administered orally as 4 mg twice daily: (i) the day of ADC administration, at least 2 hours before the ADC, and (ii) the day after ADC administration. The steroid is administered in conjunction with the ADC administered on Week 1, Day 1 of each cycle only, regardless of ADC treatment schedule.

In some embodiments Dexamethasone is administered orally as 8 mg twice daily: (i) the day before ADC administration, (ii) the day of ADC administration, preferably at least 2 hours before the ADC, and (iii) the day after ADC administration. The steroid is administered in conjunction with the ADC administered on Week 1, Day 1 of each cycle only, regardless of ADC treatment schedule.

In some embodiments Dexamethasone is administered orally as 8 mg twice daily: (i) the day of ADC administration, preferably at least 2 hours before the ADC, and (ii) the day after ADC administration. The steroid is administered in conjunction with the ADC administered on Week 1, Day 1 of each cycle only, regardless of ADC treatment schedule.

Dexamethasone:
- (i) CAS Number→50-02-2
  (see cas.org/content/chemical-substances/faqs)
- (ii) Unique Ingredient Identifier (UNII)→7S5I7G3JQL
  (see fda.gov/ForIndustry/DataStandards/SubstanceRegistrationSystem-UniqueIngredientIdentifierUNII/default.htm)
- (iii) IUPAC name→(8S,9R,10S,11S,13S,14S,16R,17R)-9-Fluoro-11,17-dihydroxy-17-(2-hydroxyacetyl)-10,13,16-trimethyl-6,7,8,9,10,11,12,13,14,15,16,17-dodecahydro-3H-cyclopenta[a]phenanthren-3-one
- (iv) Structure →

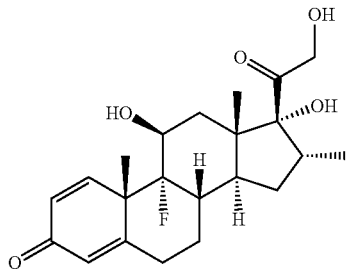

Combination with Ibrutinib

Administration of the CD19-ADC in combination with Ibrutinib is contemplated, particularly in embodiments where the proliferative disorder is lymphoma.

The Ibrutinib may be administered to the subject before, concurrently with, or after the CD19-ADC. Preferably, the CD19-ADC and Ibrutinib are administered concurrently. For example, in some cases administration of Ibrutinib begins on day 1 of treatment cycle 1 of the CD19-ADC dosage regime described herein.

When administered in combination with Ibrutinib, the CD19-ADC is preferably administered in a dosage regime consisting of two Q3W (one dose every 3 weeks) treatment cycles. Preferably, the dose administered in each of the two treatment cycles is the same. Alternatively, the second dose may be a reduced dose; that is, the dosage regime may be a tapered dosing regime as defined herein.

When administered in combination with Ibrutinib, the starting dose may be about 60 µg/kg, about 90 µg/kg, about 120 µg/kg, or about 150 µg/kg. In some embodiments when administered in combination with Ibrutinib, the starting dose of CD19-ADC may be about 140 to 160 µg/kg.

In some cases, the CD19-ADC and Ibrutinib are administered sequentially. For example, in some cases administration of Ibrutinib begins after the completion of CD19-ADC treatment.

In some cases, the administration of Ibrutinib is discontinued on the completion of CD19-ADC treatment. However, typically administration of Ibrutinib continues after the completion of CD19-ADC treatment. In some cases, Ibrutinib administration continues for up to 1 year after the completion of CD19-ADC treatment.

In cases where the subject achieves CR following initial treatment with the CD19-ADC and Ibrutinib combination, typically no further CD19-ADC is administered to the subject. In these cases, Ibrutinib administration typically continues for up to 1 year after the completion of CD19-ADC treatment.

In cases where the subject achieves SD or PR following initial treatment with the CD19-ADC and Ibrutinib combination, further CD19-ADC may be administered to the subject. In these cases, Ibrutinib administration typically continues after the initial treatment with the CD19-ADC and Ibrutinib combination. If the subject has not achieved CR within 3 months after the completion of initial CD19-ADC treatment, further CD19-ADC may be administered to the subject.

The further CD19-ADC may be administered in a dosage regime consisting of two Q3W treatment cycles. Preferably the dose administered in each of the two treatment cycles is the same. Alternatively, the second dose may be a reduced dose; that is, the dosage regime may be a tapered dosing regime as defined herein. Typically the further CD19-ADC is administered in combination with Ibrutinib treatment.

The Ibrutinib may be administered in a QD (one dose per day) dosage regime; that is, the Ibrutinib may be administered once a day. Preferably the dose of Ibrutinib administered is about 550 to 570 mg/day, such as about 560 mg/day. Reduced daily doses are about 420 mg/day and about 280 mg/day; reduced doses may be administered if, for example, the subject exhibits a treatment-related toxicity.

In some cases where the CD19-ADC is administered in combination with Ibrutinib, the subject has, or is suspected as having, or has been identified as being at risk of, or has received a diagnosis of cancer of a non-Hodgkin's Lymphoma, such as diffuse large B-cell lymphoma (DLBCL) or Mantle Cell lymphoma (MCL).

Ibrutinib (Imbruvica):
- (i) CAS Number→936563-96-1
  (see cas.org/content/chemical-substances/faqs)
- (ii) Unique Ingredient Identifier (UNII)→1X70OSD4VX
  (see fda.gov/ForIndustry/DataStandards/SubstanceRegistrationSystem-UniqueIngredientIdentifierUNII/default.htm)

(iii) IUPAC name→1-[(3R)-3-[4-Amino-3-(4-phenoxy-phenyl)-1H-pyrazolo[3,4-d]pyrimidin-1-yl]piperidin-1-yl]prop-2-en-1-one (iv) Structure →

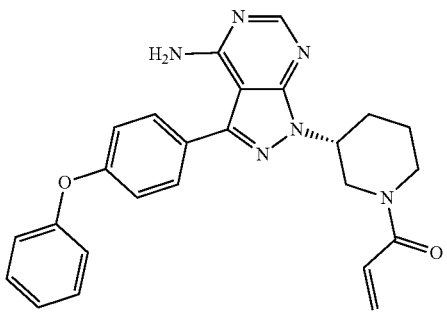

Combination with Durvalumab

Administration of the CD19-ADC in combination with Durvalumab is contemplated, particularly in embodiments where the proliferative disorder is lymphoma.

The Durvalumab may be administered to the subject before, concurrently with, or after the CD19-ADC. Preferably, the CD19-ADC and Durvalumab are administered concurrently; that is the CD19-ADC and the Durvalumab are administered as part of the same treatment cycle. In some cases the CD19-ADC and Durvalumab are not administered on the same day of the treatment cycle. For example, in some cases the CD19-ADC is administered on day 1 of the treatment cycle and Durvalumab is administered on day 8 of the treatment cycle.

When administered in combination with Durvalumab, the CD19-ADC is preferably administered in a dosage regime consisting of two Q3W treatment cycles. Preferably, the dose of CD19-ADC administered in each of the two treatment cycles is the same. Alternatively, the second dose may be a reduced dose; that is, the dosage regime may be a tapered dosing regime as defined herein.

When administered in combination with the CD19-ADC, the Durvalumab is preferably administered in a Q3W dosage regime. In some embodiments the dose of Durvalumab administered is about 1400 to 1600 mg. The dose of Durvalumab administered is preferably 1500 mg.

In some cases where the CD19-ADC is administered in combination with Durvalumab, the starting dose is about 90 µg/kg, about 120 µg/kg, or about 150 µg/kg. In some embodiments when administered in combination with Durvalumab, the starting dose of CD19-ADC may be about 140 to 160 µg/kg.

In some cases, the CD19-ADC and Durvalumab are administered sequentially. For example, in some cases administration of Durvalumab begins after the completion of CD19-ADC treatment.

In some cases, the administration of Durvalumab is discontinued on the completion of CD19-ADC treatment. However, typically administration of Durvalumab continues after the completion of CD19-ADC treatment. In some cases, Durvalumab administration continues for up to 1 year after the completion of CD19-ADC treatment.

When administered after the completion of CD19-ADC treatment, the Durvalumab is preferably administered in a Q4W dosage regime. In some embodiments the dose of Durvalumab administered is about 1400 to 1600 mg. The dose of Durvalumab administered is preferably 1500 mg.

In cases where the subject achieves CR following initial treatment with the CD19-ADC and Durvalumab combination, typically no further CD19-ADC is administered to the subject. In these cases, Durvalumab administration typically continues for up to 1 year after the completion of CD19-ADC treatment.

In cases where the subject achieves SD or PR following initial treatment with the CD19-ADC and Durvalumab combination, further CD19-ADC may be administered to the subject. In these cases, Durvalumab administration typically continues after the initial treatment with the CD19-ADC and Durvalumab combination. If the subject has not achieved CR within 3 months after the completion of initial CD19-ADC treatment, further CD19-ADC may be administered to the subject.

The further CD19-ADC may be administered in a dosage regime consisting of two Q3W treatment cycles. Preferably the dose administered in each of the two treatment cycles is the same. Alternatively, the second dose may be a reduced dose; that is, the dosage regime may be a tapered dosing regime as defined herein. Typically the further CD19-ADC is administered in combination with Durvalumab treatment.

In some cases where the CD19-ADC is administered in combination with Durvalumab, the subject has, or is suspected as having, or has been identified as being at risk of, or has received a diagnosis of cancer of a non-Hodgkin's Lymphoma, such as diffuse large B-cell lymphoma (DLBCL), Mantle Cell lymphoma (MCL), or Follicular Lymphoma (FL).

Durvalumab/MED14736:
(i) CAS Number→1428935-60-7
    (see cas.org/content/chemical-substances/faqs)
(ii) Unique Ingredient Identifier (UNII)→28X28X9OKV
    (see fda.gov/ForIndustry/DataStandards/SubstanceRegistrationSystem-UniqueIngredientIdentifierUNII/default.htm)

```
(iii) VH sequence
                                      (SEQ ID NO. 15)
EVQLVESGGGLVQPGGSLRLSCAASGFTFSRYWMSWVRQAPGKGLEWVA
NIKQDGSEKYYVDSVKGRFTISRDNAKNSLYLQMNSLRAEDTAVYYCAR
EGGWFGELAFDYWGQGTLVTVSS (iv) VL sequence
                                      (SEQ ID NO. 16)
EIVLTQSPGTLSLSPGERATLSCRASQRVSSSYLAWYQQKPGQAPRLLI
YDASSRATGIPDRFSGSGSGTDFTLTISRLEPEDFAVYYCQQYGSLPWT
FGQGTKVEIK
```

Combination with Rituximab

Administration of the CD19-ADC in combination with Rituximab is contemplated, particularly in embodiments where the proliferative disorder is lymphoma.

The Rituximab may be administered to the subject before, concurrently with, or after the CD19-ADC. Preferably, the CD19-ADC and Rituximab are administered concurrently. For example, in some cases administration of Rituximab and CD19-ADC begin on day 1 of treatment cycle 1 of the CD19-ADC dosage regime described.

In some cases, the CD19-ADC and Rituximab are administered sequentially. For example, in some cases administration of Rituximab begins after the completion of CD19-ADC treatment.

The Rituximab may be administered in a Q3W dosage regime. In some embodiments, the dose of Rituximab administered is 325 to 425 mg/m2. Preferably the dose of Rituximab administered is 375 mg/m$^2$.

Preferably, in cases where the CD19-ADC is administered in combination with Rituximab, the starting dose is about 90 μg/kg, about 120 μg/kg, or about 150 μg/kg. In some embodiments when administered in combination with Rituximab, the starting dose of CD19-ADC may be about 140 to 160 μg/kg.

In some cases where the CD19-ADC is administered in combination with Rituximab, the subject has, or is suspected as having, or has been identified as being at risk of, or has received a diagnosis of cancer of a non-Hodgkin's Lymphoma, such as diffuse large B-cell lymphoma (DLBCL).

In some cases where the CD19-ADC is administered in combination with Rituximab, the subject may be undergoing, or have undergone, treatment with Rituximab. In some cases the individual may be refractory to treatment (or further treatment) with Rituximab. In embodiments where the individual is undergoing, or has undergone, treatment with Rituximab, the anti CD19 ADC may be administered in combination with Rituximab, or without continued administration of Rituximab.

Rituximab:
(i) CAS Number→174722-31-7
(see cas.org/content/chemical-substances/faqs)
(ii) Drugbank reference→DB00073
(see drugbank.ca/)
(iii) Unique Ingredient Identifier (UNII)→4F4X42SYQ6
(see fda.gov/ForIndustry/DataStandards/SubstanceRegistrationSystem-UniqueIngredientIdentifierUNII/default.htm)

(iv) Heavy chain sequence:
(SEQ ID NO: 17)
QVQLQQPGAELVKPGASVKMSCKASGYTFTSYNMHWVKQTPGRGLEWIG

AIYPGNGDTSYNQKFKGKATLTADKSSSTAYMQLSSLTSEDSAVYYCAR

STYYGGDWYFNVWGAGTTVTVSAASTKGPSVFPLAPSSKSTSGGTAALG

CLVKDYFPEPVTVSWNSGALTSGVHTFPAVLQSSGLYSLSSVVTVPSSS

LGTQTYICNVNHKPSNTKVDKKAEPKSCDKTHTCPPCPAPELLGGPSVF

LFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKA

KGQPREPQVYTLPPSRDELTKNQVSLTCLVKGFYPSDIAVEWESNGQPE

NNYKTTPPVLDSDGSFFLYSKLTVDKSRWQQGNVFSCSVMHEALHNHYT

QKSLSLSPGK

Light chain sequence:
(SEQ ID NO. 18)
QIVLSQSPAILSASPGEKVTMTCRASSSVSYIHWFQQKPGSSPKPWIYA

TSNLASGVPVRFSGSGSGTSYSLTISRVEAEDAATYYCQQWTSNPPTFG

GGTKLEIKRTVAAPSVFIFPPSDEQLKSGTASVVCLLNNFYPREAKVQW

KVDNALQSGNSQESVTEQDSKDSTYSLSSTLTLSKADYEKHKVYACEVT

HQGLSSPVTKSFNRGEC

Combination with Cytarabine

Administration of the CD19-ADC in combination with Cytarabine is contemplated, particularly in embodiments where the proliferative disorder is lymphoma.

The Cytarabine may be administered to the subject before, concurrently with, or after the CD19-ADC. Preferably, the CD19-ADC and Cytarabine are administered concurrently.

In preferred embodiments the CD19-ADC is administered in a Q3W regime, preferably on day 2 of the treatment cycle. Preferably the CD19-ADC is administered at a starting dose for 2 treatment cycles and at a reduced dose of 50% of the starting dose in subsequent cycles. In some embodiments the starting dose is about 140 to 160 μg/kg and the reduced dose is about 70 to 80 μg/kg. Preferably the starting dose is about 150 μg/kg and the reduced dose is about 75 μg/kg.

In preferred embodiments, the Cytarabine is administered in a Q3W regime, preferably as 5 partial doses spread one partial dose per day on days 1 to 5 of each cycle. Preferably, the Cytarabine is administered as 5 equal partial doses. The partial dose may be about 100 mg/m², about 200 mg/m², about 300 mg/m², or about 400 mg/m².

In some cases where the CD19-ADC is administered in combination with cytarabine, the subject has, or is suspected as having, or has been identified as being at risk of, or has received a diagnosis of cancer of a non-Hodgkin's Lymphoma, such as diffuse large B-cell lymphoma (DLBCL).

Cytarabine:
(i) CAS Number→147-94-4 (see cas.org/content/chemical-substances/faqs)
(ii) Unique Ingredient Identifier (UNII)→04079A1RDZ
(see fda.gov/ForIndustry/DataStandards/SubstanceRegistrationSystem-UniqueIngredientIdentifierUNII/default.htm)
(iii) IUPAC name: 4-amino-1-[(2R,3S,4R,5R)-3,4-dihydroxy-5-(hydroxymethyl)oxolan-2-yl]pyrimidin-2-one (iv) Structure →

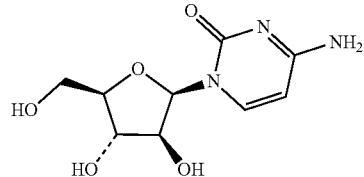

Combination with Cytarabine and Rituximab

Administration of the CD19-ADC in combination with Cytarabine and Rituximab is contemplated, particularly in embodiments where the proliferative disorder is lymphoma.

The Cytarabine and Rituximab may be administered to the subject before, concurrently with, or after the CD19-ADC. Preferably, the CD19-ADC, Cytarabine and Rituximab are administered concurrently. For example, in some cases administration of Cytarabine, Rituximab, and CD19-ADC begin on day 1 of treatment cycle 1 of the CD19-ADC dosage regime described.

In preferred embodiments the Rituximab is administered in a Q3W regime, preferably on day 1 of the treatment cycle. In some embodiments the dose of Rituximab administered is 325 to 425 mg/m2. Preferably the dose of Rituximab administered is 375 mg/m².

In preferred embodiments the CD19-ADC is administered in a Q3W regime, preferably on day 2 of the treatment cycle. Preferably the CD19-ADC is administered at a starting dose for 2 treatment cycles and at a reduced dose of 50% of the starting dose in subsequent cycles. In some embodiments the starting dose is about 140 to 160 μg/kg and the reduced dose is about 70 to 80 μg/kg. Preferably the starting dose is about 150 μg/kg and the reduced dose is about 75 μg/kg.

In preferred embodiments, the Cytarabine is administered in a Q3W regime, preferably as 5 partial doses spread one partial dose per day on days 1 to 5 of each cycle. Preferably, the Cytarabine is administered as 5 equal partial doses. The partial dose may be about 100 mg/m$^2$, about 200 mg/m$^2$, about 300 mg/m$^2$, or about 400 mg/m$^2$.

In some cases where the CD19-ADC is administered in combination with Rituximab and cytarabine, the subject has, or is suspected as having, or has been identified as being at risk of, or has received a diagnosis of cancer of a non-Hodgkin's Lymphoma, such as diffuse large B-cell lymphoma (DLBCL).

In some cases where the CD19-ADC is administered in combination with cytarabine and Rituximab, the subject may be undergoing, or have undergone, treatment with Rituximab. In some cases the individual may be refractory to treatment (or further treatment) with Rituximab. In embodiments where the individual is undergoing, or has undergone, treatment with Rituximab, the anti CD19 ADC may be administered in combination with Rituximab, or without continued administration of Rituximab.

Specifically envisaged are embodiments where the CD19-ADC is administered in combination with a diuretic, such as spironolactone. The diuretic may be administered to subjects receiving CD19-ADC that are exhibiting an increase in weight, oedema or pleural effusion.

Specifically envisaged are embodiments where the CD19-ADC is administered in combination with intrathecal medication for CNS prophylaxis.

Compositions according to the present disclosure are preferably pharmaceutical compositions. Pharmaceutical compositions according to the present disclosure, and for use in accordance with the present disclosure, may comprise, in addition to the active ingredient, i.e. a conjugate compound, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Dosage

It will be appreciated by one of skill in the art that appropriate dosages of the ADC and compositions comprising these active elements, can vary from subject to subject. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the subject. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

In certain aspects, the dosage of ADC is determined by the expression of CD19 in a sample obtained from the subject. Thus, the level or localisation of expression of CD19 in the sample may be indicative that a higher or lower dose of ADC is required. For example, a high expression level CD19 may indicate that a higher dose of ADC would be suitable. In some cases, a high expression level of CD19 may indicate the need for administration of another agent in addition to the ADC. For example, administration of the ADC in conjunction with a chemotherapeutic agent. A high expression level of the CD19 may indicate a more aggressive therapy.

In general, a suitable dose of each active compound is in the range of about 100 ng to about 25 mg (more typically about 1 µg to about 10 mg) per kilogram body weight of the subject per day. Where the active compound is a salt, an ester, an amide, a prodrug, or the like, the amount administered is calculated on the basis of the parent compound and so the actual weight to be used is increased proportionately.

In some situations dosage normalization based on body size parameters such as Body Surface Area (BSA) better accounts for intersubject variability in ADC pharmacokinetics such as clearance rate than normalization based on body weight. In these situations, calculation of dosage levels using body size parameters allows for more precise dosing, Accordingly, in some aspects the dose of the ADC administered to the subject is normalised to the subject body size (i.e. not subject body weight). In some cases, the dose of the ADC administered to the subject is normalised to the subject body surface area (BSA). Preferably, the ADC dosage is normalised to BSA using the DuBois formula (as disclosed in, for example, Japanese Journal of Clinical Oncology, Volume 33, Issue 6, 1 Jun. 2003, Pages 309-313, doi.org/10.1093/jjco/hyg062).

Antibodies

The term "antibody" herein is used in the broadest sense and specifically covers monoclonal antibodies, polyclonal antibodies, dimers, multimers, multispecific antibodies (e.g., bispecific antibodies), intact antibodies (also described as "full-length" antibodies) and antibody fragments, so long as they exhibit the desired biological activity, for example, the ability to bind a first target protein (Miller et al (2003) *Jour. of Immunology* 170:4854-4861). Antibodies may be murine, human, humanized, chimeric, or derived from other species such as rabbit, goat, sheep, horse or camel.

An antibody is a protein generated by the immune system that is capable of recognizing and binding to a specific antigen. (Janeway, C., Travers, P., Walport, M., Shlomchik (2001) *Immuno Biology*, 5th Ed., Garland Publishing, New York). A target antigen generally has numerous binding sites, also called epitopes, recognized by Complementarity Determining Regions (CDRs) on multiple antibodies. Each antibody that specifically binds to a different epitope has a different structure. Thus, one antigen may have more than one corresponding antibody. An antibody may comprise a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin can be of any type (e.g. IgG, IgE, IgM, IgD, and IgA), class (e.g. IgG1, IgG2, IgG3, IgG4, IgA1 and IgA2) or subclass, or allotype (e.g. human G1m1, G1m2, G1m3, non-G1m1 [that, is any allotype other than G1m1], G1m17, G2m23, G3m21, G3m28, G3m11, G3m5, G3m13, G3m14, G3m10, G3m15, G3m16, G3m6, G3m24, G3m26, G3m27, A2m1, A2m2, Km1, Km2 and Km3) of immunoglobulin molecule. The immunoglobulins can be derived from any species, including human, murine, or rabbit origin.

"Antibody fragments" comprise a portion of a full length antibody, generally the antigen binding or variable region thereof. Examples of antibody fragments include Fab, Fab', F(ab')$_2$, and scFv fragments; diabodies; linear antibodies; fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler et al (1975) *Nature* 256:495, or may be made by recombinant DNA methods (see, U.S. Pat. No. 4,816,567). The monoclonal antibodies may also be isolated from phage antibody libraries using the techniques described in Clackson et al (1991) *Nature,* 352:624-628; Marks et al (1991) J. Mol. Biol., 222:581-597 or from transgenic mice carrying a fully human immunoglobulin system (Lonberg (2008) Curr. Opinion 20(4):450-459).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) *Proc. Natl. Acad. Sci. USA,* 81:6851-6855). Chimeric antibodies include "primatized" antibodies comprising variable domain antigen-binding sequences derived from a non-human primate (e.g. Old World Monkey or Ape) and human constant region sequences.

An "intact antibody" herein is one comprising VL and VH domains, as well as a light chain constant domain (CL) and heavy chain constant domains, CH1, CH2 and CH3. The constant domains may be native sequence constant domains (e.g. human native sequence constant domains) or amino acid sequence variant thereof. The intact antibody may have one or more "effector functions" which refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors such as B cell receptor and BCR.

Depending on the amino acid sequence of the constant domain of their heavy chains, intact antibodies can be assigned to different "classes." There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

The disclosure includes the combination of the cases and preferred features described except where such a combination is clearly impermissible or expressly avoided.

The section headings used herein are for organizational purposes only and are not to be construed as limiting the subject matter described.

Cases and embodiments of the present disclosure will now be illustrated, by way of example, with reference to the accompanying figures. Further cases and embodiments will be apparent to those skilled in the art. All documents mentioned in this text are incorporated herein by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

Some Embodiments

Lymphoma

The disclosure provides a method of treating a proliferative disease in a subject, said method comprising administering to a subject a CD19-ADC, wherein the CD19-ADC is administered to the subject in a tapered and/or elongated dosage regimes.

In some cases the dosage regime comprises dosing about 120 µg/kg every 3 weeks for 2 cycles, then continuing treatment with the third and subsequent cycles at a reduced dose of about 60 µg/kg every 6 weeks, beginning 6 weeks after cycle 2 administration. Preferably only subjects who have attained at least SD after the second cycle will continue with the reduced dose and increased cycle length.

In some cases the dosage regime comprises dosing about 150 µg/kg every 3 weeks for 2 cycles, then continuing treatment with the third and subsequent cycles at a reduced dose of about 60 µg/kg every 6 weeks, beginning 6 weeks after cycle 2 administration. Preferably only subjects who have attained at least SD after the second cycle will continue with the reduced dose and increased cycle length.

In some preferred cases the dosage regime comprises dosing about 140 to 160 µg/kg every 3 weeks for 2 cycles, then continuing treatment with the third and subsequent cycles at a reduced dose of about 70 to 80 µg/kg every 3 weeks, beginning 3 weeks after cycle 2 administration. Preferably only subjects who have attained at least SD after the second cycle will continue with the reduced dose.

In some particularly preferred cases the dosage regime comprises dosing about 150 µg/kg every 3 weeks for 2 cycles, then continuing treatment with the third and subsequent cycles at a reduced dose of about 75 µg/kg every 3 weeks, beginning 3 weeks after cycle 2 administration. Preferably only subjects who have attained at least SD after the second cycle will continue with the reduced dose.

In some cases the dosage regime comprises dosing about 200 µg/kg every 6 weeks for 2 cycles, then continuing treatment with the third and subsequent cycles at a reduced dose of about 60 µg/kg every 6 weeks, beginning 6 weeks after cycle 2 administration. Preferably only subjects who have attained at least SD after the second cycle will continue with the reduced dose.

In some cases the dosage regime comprises dosing about 200 µg/kg every 6 weeks for 1 cycle, then continuing treatment with the second and subsequent cycles at a reduced dose of about 60 µg/kg every 6 weeks, beginning 6 weeks after cycle 1 administration. Preferably only subjects who have attained at least SD after the first cycle will continue with the reduced dose.

In some cases the dosage regime comprises dosing about 45 µg/kg every 3 weeks for up to 4 treatment cycles, then continuing treatment every 3 weeks at a reduced dose of about 30 µg/kg or about 20 µg/kg (such as 20 to 30 µg/kg). In some cases, the starting dose of 45 µg/kg is administered for only 1 treatment cycle before the dose is reduced. In some cases, the starting dose of 45 µg/kg is administered for only 2 treatment cycles before the dose is reduced. In some cases, the starting dose of 45 µg/kg is administered for only 3 treatment cycles before the dose is reduced. In some cases, the starting dose of 45 µg/kg is administered for 4 treatment cycles before the dose is reduced.

Preferably the CD19-ADC is administered as single dose on Day 1 of each cycle, unless otherwise specified.

Preferably the CD19-ADC is ADCx19 as described herein.

Preferably the proliferative disease is a B-cell Lineage Non Hodgkin Lymphoma (B-NHL), such as diffuse large B-cell lymphoma (DLBCL), follicular lymphoma, (FL), Mantle Cell lymphoma (MCL), chronic lymphatic lymphoma (CLL), Waldenstroms Microglobulinemia, Burkitt's lymphoma, and Marginal Zone B-cell lymphoma (MZBL). The disease may be relapsed or refractory.

Preferably the subject is human.

Preferably the CD19-ADC is administered in combination with dexamethasone, as described herein.

Combination with Ibrutinib

In embodiments where the CD19-ADC is administered in combination with Ibrutinib, the CD19-ADC is preferably administered in a dosage regime consisting of two, equal, Q3W treatment cycles.

Preferably, the starting dose of CD19-ADC is about 60 µg/kg, about 90 µg/kg, about 120 µg/kg, or about 150 µg/kg.

The Ibrutinib is preferably administered concurrently with the CD19-ADC in a QD regime. The dose of Ibrutinib is preferably about 560 mg/day.

Preferably, the administration of Ibrutinib continues after the completion of CD19-ADC treatment.

In cases where the subject achieves CR following initial treatment with the CD19-ADC and Ibrutinib combination, preferably no further CD19-ADC is administered to the subject.

In cases where the subject achieves SD or PR following initial treatment with the CD19-ADC and Ibrutinib combination, preferably, the administration of Ibrutinib continues after the completion of CD19-ADC treatment. If the subject has not achieved CR within 3 months after the completion of initial CD19-ADC treatment, preferably further CD19-ADC is administered to the subject.

Preferably, the further CD19-ADC is administered in a dosage regime consisting of two, equal, Q3W treatment cycles in combination with Ibrutinib, as described above.

Combination with Durvalumab

In embodiments where the CD19-ADC is administered in combination with Durvalumab, the CD19-ADC is preferably administered in a dosage regime consisting of two, equal, Q3W treatment cycles.

Preferably, the starting dose of CD19-ADC is about 90 µg/kg, about 120 µg/kg, or about 150 µg/kg.

The Durvalumab is preferably administered concurrently with the CD19-ADC in a Q3W regime. The dose of Durvalumab is preferably about 1500 mg.

When administered concurrently in a Q3W regime, preferably the CD19-ADC is administered on day 1 of the Q3W cycle and the Durvalumab is administered on day 8 of the Q3W cycle.

Preferably, the administration of Durvalumab continues after the completion of CD19-ADC treatment. When administered after the completion of CD19-ADC treatment, the Durvalumab is preferably administered in a Q4W dosage regime. The dose of Durvalumab administered is preferably about 1500 mg.

In cases where the subject achieves CR following initial treatment with the CD19-ADC and Durvalumab combination, preferably no further CD19-ADC is administered to the subject.

In cases where the subject achieves SD or PR following initial treatment with the CD19-ADC and Durvalumab combination, preferably the administration of Durvalumab continues after the completion of CD19-ADC treatment. If the subject has not achieved CR within 3 months after the completion of initial CD19-ADC treatment, preferably further CD19-ADC is administered to the subject.

Preferably, the further CD19-ADC is administered in a dosage regime consisting of two, equal, Q3W treatment cycles in combination with Durvalumab, as described above.

Combination with Rituximab

In some embodiments where the CD19-ADC is administered in combination with Rituximab, the CD19-ADC is administered in a dosing regime comprising dosing about 140 to 160 µg/kg every 3 weeks for 2 cycles, then continuing treatment with the third and subsequent cycles at a reduced dose of about 70 to 80 µg/kg every 3 weeks, beginning 3 weeks after cycle 2 administration.

In some preferred embodiments where the CD19-ADC is administered in combination with Rituximab, the CD19-ADC is preferably administered in a dosing regime comprising dosing about 150 µg/kg every 3 weeks for 2 cycles, then continuing treatment with the third and subsequent cycles at a reduced dose of about 75 µg/kg every 3 weeks, beginning 3 weeks after cycle 2 administration.

The Rituximab is preferably administered concurrently with the CD19-ADC in a Q3W regime; for example, both on day 1 of each treatment cycle. In some embodiments the dose of Rituximab is about 325 to 425 mg/m². The dose of Rituximab is preferably about 375 mg/m².

Combination with Cytarabine

In some embodiments where the CD19-ADC is administered in combination with Cytarabine, the CD19-ADC is administered in a dosing regime comprising dosing about 140 to 160 µg/kg every 3 weeks for 2 cycles, then continuing treatment with the third and subsequent cycles at a reduced dose of about 70 to 80 µg/kg every 3 weeks, beginning 3 weeks after cycle 2 administration.

In some preferred embodiments where the CD19-ADC is administered in combination with Cytarabine, the CD19-ADC is preferably administered in a dosing regime comprising dosing about 150 µg/kg every 3 weeks for 2 cycles, then continuing treatment with the third and subsequent cycles at a reduced dose of about 75 µg/kg every 3 weeks, beginning 3 weeks after cycle 2 administration.

Preferably the CD19-ADC is administered on day 2 of each Q3W treatment cycle.

The cytarabine is preferably administered concurrently with the CD19-ADC in a Q3W regime. Preferably the cytarabine is administered as 5 equal, partial doses spread one partial dose per day on days 1 to 5 of each cycle. The partial dose level may be about 100 mg/m², about 200 mg/m², about 300 mg/m², or about 400 mg/m² per partial dose.

Combination with Cytarabine and Rituximab

In some embodiments where the CD19-ADC is administered in combination with Cytarabine and Rituximab, the CD19-ADC is administered in a dosing regime comprising dosing about 140 to 160 µg/kg every 3 weeks for 2 cycles, then continuing treatment with the third and subsequent cycles at a reduced dose of about 70 to 80 µg/kg every 3 weeks, beginning 3 weeks after cycle 2 administration.

In some preferred embodiments where the CD19-ADC is administered in combination with Cytarabine and Rituximab, the CD19-ADC is preferably administered in a dosing regime comprising dosing about 150 µg/kg every 3 weeks for 2 cycles, then continuing treatment with the third and subsequent cycles at a reduced dose of about 75 µg/kg every 3 weeks, beginning 3 weeks after cycle 2 administration.

Preferably the CD19-ADC is administered on day 2 of each Q3W treatment cycle.

The Rituximab is preferably administered concurrently with the CD19-ADC in a Q3W regime. In some embodiments the dose of Rituximab is about 325 to 425 mg/m². The dose of Rituximab is preferably about 375 mg/m².

Preferably the Rituximab is administered on day 1 of each Q3W treatment cycle.

The cytarabine is preferably administered concurrently with the CD19-ADC in a Q3W regime. Preferably the cytarabine is administered as 5 equal, partial doses spread one partial dose per day on days 1 to 5 of each cycle. The partial dose level may be about 100 mg/m², about 200 mg/m², about 300 mg/m², or about 400 mg/m² per partial dose.

Leukaemia

Fractionated dosage regimes in which a partial dose is administered to the subject once per week are specifically contemplated. For example, on days 1, 8, and 15 of a 21 day (3-week) treatment cycle.

Preferably each partial dose is of equal size, that is, each partial dose delivers the same amount of CD19-ADC to the subject.

Preferably, each partial dose is 40 to 60 µg/kg, such as 45 to 55 µg/kg. In particularly preferred cases each partial dose is 50 µg/kg.

Preferably the CD19-ADC is ADCx19 as described herein.

Preferably the subject is human.

Preferably the proliferative disease is a leukaemia, such as Hairy cell leukaemia (HCL), Hairy cell leukaemia variant (HCL-v), and Acute Lymphoblastic Leukaemia (ALL) such as Philadelphia chromosome-positive ALL (Ph+ALL) or Philadelphia chromosome-negative ALL (Ph-ALL). The disease may be relapsed or refractory.

The use of this type of fractionated dosage regime to treat haematological cancers such as ALL are embodiments of particular interest. Preferably the ALL is CD19+, and may be relapsed or refractory types.

Preferably the CD19-ADC is administered in combination with dexamethasone, as described herein.

Statements of Disclosure

Lymphoma

1. A method of treating a proliferative disease in a subject, said method comprising administering to a subject a CD19-ADC, wherein the CD19-ADC comprises a conjugate of formula L-(D$^L$)$_p$, where D$^L$ is of formula I or II:

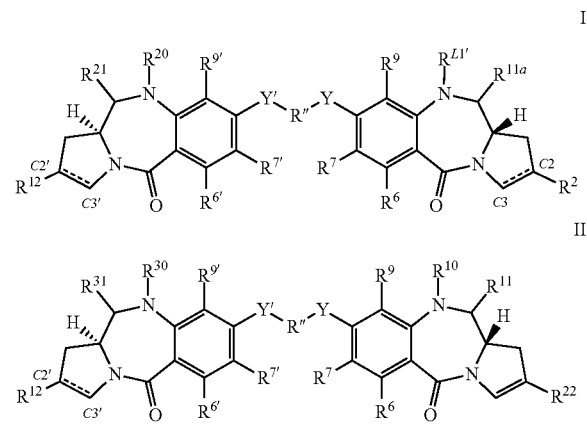

wherein:

L is an antibody (Ab) which is an antibody that binds to CD19;

when there is a double bond present between C2' and C3', R$^{12}$ is selected from the group consisting of:

(ia) C$_{5-10}$ aryl group, optionally substituted by one or more substituents selected from the group comprising:

halo, nitro, cyano, ether, carboxy, ester, $C_{1-7}$ alkyl, $C_{3-7}$ heterocyclyl and bis-oxy-$C_{1-3}$ alkylene;

(ib) $C_{1-5}$ saturated aliphatic alkyl;

(ic) $C_{3-6}$ saturated cycloalkyl;

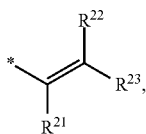

(id)

wherein each of $R^{21}$, $R^{22}$ and $R^{23}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5;

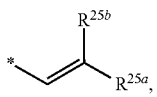

(ie)

wherein one of $R^{25a}$ and $R^{25b}$ is H and the other is selected from: phenyl, which phenyl is optionally substituted by a group selected from halo, methyl, methoxy; pyridyl; and thiophenyl; and

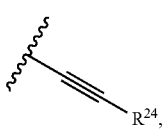

(if)

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

when there is a single bond present between C2' and C3', $R^{12}$ is

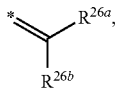

where $R^{26a}$ and $R^{26b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{26a}$ and $R^{26b}$ is H, the other is selected from nitrile and a $C_{1-4}$ alkyl ester;

$R^6$ and $R^9$ are independently selected from H, R, OH, OR, SH, SR, $NH_2$, NHR, NRR', nitro, $Me_3Sn$ and halo;

where R and R' are independently selected from optionally substituted $C_{1-12}$ alkyl, $C_{3-20}$ heterocyclyl and $C_{5-20}$ aryl groups;

$R^7$ is selected from H, R, OH, OR, SH, SR, $NH_2$, NHR, NHRR', nitro, $Me_3Sn$ and halo;

R" is a $C_{3-12}$ alkylene group, which chain may be interrupted by one or more heteroatoms, e.g. O, S, $NR^{N2}$ (where $R^{N2}$ is H or $C_{1-4}$ alkyl), and/or aromatic rings, e.g. benzene or pyridine;

Y and Y' are selected from O, S, or NH;

$R^{6'}$, $R^{7'}$, $R^{9'}$ are selected from the same groups as $R^6$, $R^7$ and $R^9$ respectively;

[Formula I]

$R^{L1'}$ is a linker for connection to the antibody (Ab);

$R^{11a}$ is selected from OH, $OR^A$, where $R^A$ is $C_{1-4}$ alkyl, and $SO_zM$, where z is 2 or 3 and M is a monovalent pharmaceutically acceptable cation;

$R^{20}$ and $R^{21}$ either together form a double bond between the nitrogen and carbon atoms to which they are bound or;

$R^{20}$ is selected from H and $R^C$, where $R^C$ is a capping group;

$R^{21}$ is selected from OH, $OR^A$ and $SO_zM$;

when there is a double bond present between C2 and C3, $R^2$ is selected from the group consisting of:

(ia) $C_{5-10}$ aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{1-3}$ alkylene;

(ib) $C_{1-5}$ saturated aliphatic alkyl;

(ic) $C_{3-6}$ saturated cycloalkyl;

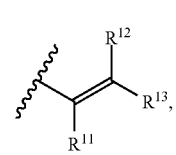

(id)

wherein each of $R^{11}$, $R^{12}$ and $R^{13}$ are independently selected from H, $C_{1-3}$ saturated alkyl, $C_{2-3}$ alkenyl, $C_{2-3}$ alkynyl and cyclopropyl, where the total number of carbon atoms in the $R^2$ group is no more than 5;

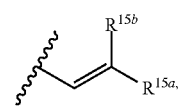

(ie)

wherein one of $R^{15a}$ and $R^{15b}$ is H and the other is selected from: phenyl, which phenyl is optionally substituted by a group selected from halo, methyl, methoxy; pyridyl; and thiophenyl; and

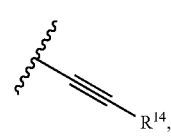

(if)

where $R^{14}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

when there is a single bond present between C2 and C3, $R^2$ is

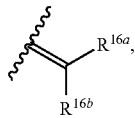

where $R^{16a}$ and $R^{16b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{16a}$ and $R^{16b}$ is H, the other is selected from nitrile and a $C_{1-4}$ alkyl ester;

[Formula II]

$R^{22}$ is of formula IIIa, formula IIIb or formula IIIc:

IIIa

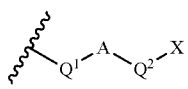

(a)

where A is a $C_{5-7}$ aryl group, and either (i) $Q^1$ is a single bond, and $Q^2$ is selected from a single bond and $-Z-(CH_2)_n-$, where Z is selected from a single bond, O, S and NH and n is from 1 to 3; or (ii) $Q^1$ is $-CH=CH-$, and $Q^2$ is a single bond;

IIIb

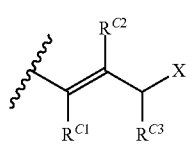

(b)

where;

$R^{C1}$, $R^{C2}$ and $R^{C3}$ are independently selected from H and unsubstituted $C_{1-2}$ alkyl;

IIIc

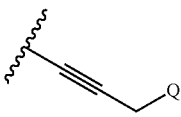

(c)

where Q is selected from $O-R^{L2'}$, $S-R^{L2'}$ and $NR^N-R^{L2'}$, and $R^N$ is selected from H, methyl and ethyl X is selected from the group comprising: $O-R^{L2'}$, $S-R^{L2'}$, $CO_2-R^{L2'}$, $NH-C(=O)-R^{L2'}$, $NHNH-R^{L2'}$, $CONHNH-R^{L2'}$,

[structures showing tetrahydropyridine-N-$R^{L2'}$ and piperazine-N-$R^{L2'}$]

$NR^N R^{L2'}$, wherein $R^N$ is selected from the group comprising H and $C_{1-4}$ alkyl;

$R^{L2'}$ is a linker for connection to the antibody (Ab);

$R^{10}$ and $R^{11}$ either together form a double bond between the nitrogen and carbon atoms to which they are bound or;

$R^{10}$ is H and $R^{11}$ is selected from OH, $OR^A$ and $SO_zM$;

$R^{30}$ and $R^{31}$ either together form a double bond between the nitrogen and carbon atoms to which they are bound or;

$R^{30}$ is H and $R^{31}$ is selected from OH, $OR^A$ and $SO_zM$.

2. The method according to statement 1 wherein the CD19-ADC is administered to the subject in a tapered and/or elongated dosage regime.

3. The method according to either one of statements 1 or 2 wherein the CD19-ADC has the chemical structure:

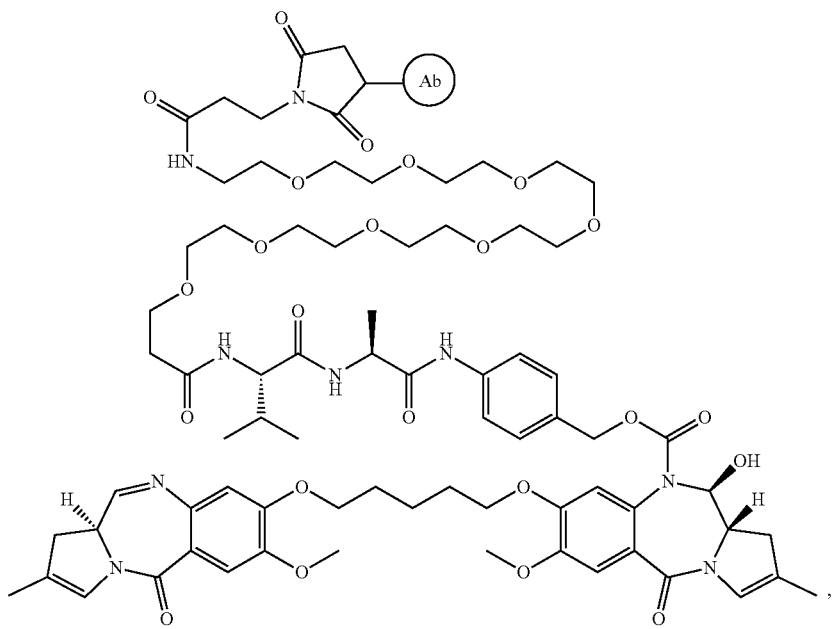

where the Ab is a CD19 antibody, and the DAR is between 1 and 8.

4. The method according to any one of statements 1 to 3 wherein Ab comprises a VH domain having the sequence of SEQ ID NO. 2 and a VL domain having the sequence of SEQ ID NO. 8.

5. The method according to any one of statements 1 to 4 wherein Ab comprises a heavy chain having sequences of SEQ ID NO. 13 and a light chain having the sequences of SEQ ID NO. 14.

6. The method according to any one of statements 1 to 5 wherein the CD19-ADC is ADCx19.

7. The method according to any preceding statement wherein the starting dose of CD19-ADC is reduced no more than twice during the dosage regime.

8. The method according to any preceding statement wherein the starting dose of CD19-ADC is reduced no more than once during the dosage regime.

9. The method according to any preceding statement wherein the dose is reduced following the first treatment cycle.

10. The method according to any preceding statement wherein the dose is reduced following the second treatment cycle.

11. The method according to any preceding statement wherein the dose is reduced following the third treatment cycle.

12. The method according to any preceding statement wherein the dose is reduced following the fourth treatment cycle.

13. The method according to any preceding statement wherein the dose is reduced only if the subject has attained at least Stable Disease [SD] at the end of the preceding treatment cycle.

14. The method according to any preceding statement wherein the starting dose is 40 to 50 µg/kg, such as about 45 µg/kg.

15. The method according to any preceding statement wherein the starting dose is at least 60 µg/kg.

16. The method according to any preceding statement wherein the starting dose is about 60 µg/kg.

17. The method according to any preceding statement wherein the starting dose is at least 90 µg/kg.

18. The method according to any preceding statement wherein the starting dose is about 90 µg/kg.

19. The method according to any preceding statement wherein the starting dose is at least 120 µg/kg.

20. The method according to any preceding statement wherein the starting dose is about 120 µg/kg.

21. The method according to any preceding statement wherein the starting dose is at least 150 µg/kg.

22. The method according to any preceding statement wherein the starting dose is about 140 to 160 µg/kg, such as 150 µg/kg.

23. The method according to any preceding statement wherein the starting dose is at least 200 µg/kg.

24. The method according to any preceding statement wherein the starting dose is about 200 µg/kg.

25. The method according to any preceding statement wherein the reduced dose is about 50% of the starting dose.

26. The method according to any preceding statement wherein the reduced dose is about 60 µg/kg.

27. The method according to any preceding statement wherein the reduced dose is about 70 to 80 µg/kg, optionally wherein the reduced dose is 75 µg/kg.

28. The method according to any preceding statement wherein the reduced dose is 15 to 35 µg/kg, such as about 20 µg/kg or about 30 µg/kg.

29. The method according to any preceding statement wherein each treatment cycle is the same length.

30. The method according to statement 29, wherein each treatment cycle is 3 weeks.

31. The method according to statement 29, wherein each treatment cycle is 6 weeks.

32. The method according to statement 31, wherein about 200 µg/kg of CD19-ADC are administered for two, 6-week treatment cycles,
followed by subsequent 6-week cycles of 60 µg/kg beginning 6 weeks after the cycle 2 administration.

33. The method according to statement 31, wherein about 200 µg/kg of CD19-ADC are administered for one, 6-week treatment cycle,
followed by subsequent 6-week cycles of 60 µg/kg beginning 6 weeks after the cycle 1 administration.

34. The method according to statement 30, wherein about 140 to 160 µg/kg of CD19-ADC are administered for two, 3-week treatment cycles,
followed by subsequent 3-week cycles of 70 to 80 µg/kg beginning 3 weeks after the cycle 2 administration;
optionally wherein about 150 µg/kg of CD19-ADC are administered for two, 3-week treatment cycles,
followed by subsequent 3-week cycles of 75 µg/kg beginning 3 weeks after the cycle 2 administration 35. The method according to any one of statements 1 to 27, wherein the treatment cycle length is increased no more than twice during the dosage regime.

36. The method according to any one of statements 1 to 27 or 31, wherein the treatment cycle length is increased no more than once during the dosage regime.

37. The method according to any one of statements 1 to 27 or 35 to 36, wherein the treatment cycle length is increased following the first treatment cycle.

38. The method according to any one of statements 1 to 27 or 35 to 37, wherein the treatment cycle length is increased following the second treatment cycle.

39. The method according to any one of statements 1 to 27 or 35 to 38, wherein the cycle length is increased only if the subject has attained at least Stable Disease [SD] at the end of the preceding treatment cycle.

40. The method according to any one of statements 1 to 27 or 35 to 39, wherein Day 1' of the first treatment cycle of increased length is delayed so that the time elapsed between 'Day 1' of the final shorter treatment cycle and Day 1' of the first treatment cycle of increased length is equal in length to the increased treatment cycle.

41. The method according to any one of statements 1 to 27 or 35 to 40, wherein the starting length is 3 weeks.

42. The method according to any one of statements 1 to 27 or 35 to 41, wherein the increased length is 6 weeks.

43. The method according to statement 42, wherein about 150 µg/kg of CD19-ADC are administered for two, 3-week treatment cycles, followed by subsequent 6-week cycles of 60 µg/kg beginning 6 weeks after the cycle 2 administration.

44. The method according to statement 42, wherein about 120 µg/kg of CD19-ADC are administered for two, 3-week treatment cycles,
followed by subsequent 6-week cycles of 60 µg/kg beginning 6 weeks after the cycle 2 administration.

45. The method according to any preceding statement, wherein the CD19-ADC is administered as a single dose.

46. The method according to any preceding statement, wherein the dose of CD19-ADC is administered on Day 1 of the treatment cycle.

47. The method according to any preceding statement wherein the proliferative disease is characterised by the presence of a neoplasm comprising CD19+ve cells 48. The method according to any preceding statement wherein the subject has been diagnosed as having the proliferative disease prior to the start of treatment with the CD19-ADC.

49. The method according to any preceding statement, wherein the disease is B-cell Lineage Non-Hodgkin Lymphoma (B-NHL).

50. The method according to any preceding statement wherein the method comprises the step of selecting a subject for treatment based on expression of CD19.

51. The method according to statement 50, wherein a subject is selected if at least 5% of neoplasm cells express CD19.

52. The method according to any preceding statement wherein the proliferative disease is non-Hodgkin's Lymphoma, including diffuse large B-cell lymphoma (DLBCL), follicular lymphoma, (FL), Mantle Cell lymphoma (MCL), chronic lymphatic lymphoma (CLL), Waldenstroms Microglobulinemia, Burkitt's lymphoma, and Marginal Zone B-cell lymphoma (MZBL), and leukemias such as Hairy cell leukaemia (HCL), Hairy cell leukaemia variant (HCL-v), and Acute Lymphoblastic Leukaemia (ALL) such as Philadelphia chromosome-positive ALL (Ph+ALL) or Philadelphia chromosome-negative ALL (Ph-ALL).

53. The method according to any preceding statement wherein the proliferative disease is B-cell Lineage Non-Hodgkin Lymphoma (B-NHL).

54. The method according to any preceding statement wherein the proliferative disease is resistant, relapsed or refractory.

55. The method according to any preceding statement wherein the subject is human.

56. The method according to any preceding statement wherein the CD19-ADC is administered intravenously.

57. The method according to any preceding claim further comprising administering a chemotherapeutic agent in combination with the CD19-ADC.

58. The method according to statement 57, wherein the chemotherapeutic agent is a checkpoint inhibitor.

59. The method according to statement 57, wherein the chemotherapeutic agent is ibrutinib.

60. The method according to statement 59, wherein the ibrutinib is administered concurrently with the CD19-ADC.

61. The method according to either one of statements 59 or 60, wherein the ibrutinib is administered in a QD dosage regime.

62. The method according to any one of statements 59 to 61, wherein the dose of ibrutinib administered is 560 mg/day, 420 mg/day, or 280 mg/day.

63. The method according to any one of statements 59 to 61, wherein the dose of ibrutinib administered is 560 mg/day.

64. The method according to any one of statements 59 to 63, wherein the CD19-ADC is administered to the subject for two Q3W cycles.

65. The method according to statement 64, wherein the dose of CD19-ADC administered in each of the two, 3-week treatment cycles is the same.

66. The method according to any one of statements 59 to 65, wherein the dose of CD19-ADC is about 60 µg/kg, about 90 µg/kg, about 120 µg/kg, about 140 to 160 µg/kg, or about 150 µg/kg.

67. The method according to any one of statements 59 to 66, wherein the administration of Ibrutinib continues after the completion of CD19-ADC treatment.

68. The method according to any one of statements 64 to 67, wherein the CD19-ADC is administered to the subject for a further two, 3-week treatment cycles.

69. The method according to statements 68, wherein the further two CD19-ADC treatment cycles are administered If the subject has not achieved CR within 3 months after the completion of initial two, 3-week treatment cycles.

70. The method according to any one of statements 59 to 69, wherein the subject has, or is suspected as having, or has been identified as being at risk of, or has received a diagnosis of a non-Hodgkin's Lymphoma, such as diffuse large B-cell lymphoma (DLBCL) or Mantle Cell lymphoma (MCL).

71. The method according to statement 57, wherein the chemotherapeutic agent is Durvalumab.

72. The method according to statement 71, wherein the Durvalumab is administered concurrently with the CD19-ADC.

73. The method according to either one of statements 71 or 72, wherein the Durvalumab is administered in a Q3W dosage regime.

74. The method according to any one of statements 71 to 73, wherein the dose of Durvalumab is 1500 mg.

75. The method according to any one of statements 71 to 74, wherein the CD19-ADC is administered to the subject for two, 3-week treatment cycles.

76. The method according to statement 75, wherein the dose of CD19-ADC administered in each of the two, 3-week treatment cycles is the same.

77. The method according to any one of statements 71 to 76, wherein the dose of CD19-ADC is about 90 µg/kg, about 120 µg/kg, about 140 to 160 µg/kg, or about 150 µg/kg.

78. The method according to any one of statements 71 to 77, wherein the administration of Durvalumab continues after the completion of CD19-ADC treatment.

79. The method according to statement 78, wherein after the completion of CD19-ADC treatment the Durvalumab is administered in a Q4W dosage regime.

80. The method according to any one of statements 75 to 79, wherein the CD19-ADC is administered to the subject for a further two, 3-week treatment cycles.

81. The method according to statements 80, wherein the further two CD19-ADC treatment cycles are administered If the subject has not achieved CR within 3 months after the completion of initial two, 3-week treatment cycles.

82. The method according to any one of statements 59 to 69, wherein the subject has, or is suspected as having, or has been identified as being at risk of, or has received a diagnosis of a non-Hodgkin's Lymphoma, such as diffuse large B-cell lymphoma (DLBCL), Follicular Lymphoma (FL), or Mantle Cell lymphoma (MCL).

83. The method according to statement 57, wherein the chemotherapeutic agent is Rituximab.

84. The method according to statement 83, wherein the Rituximab is administered concurrently with the CD19-ADC.

85. The method according to either one of statements 83 or 84, wherein the Rituximab is administered in a Q3W dosage regime.

86. The method according to any one of statements 83 to 85, wherein the dose of Rituximab administered is 325 to 425 mg/m²;
Optionally wherein the dose of Rituximab administered is 375 mg/m².

87. The method according to any one of statements 83 to 86, wherein the dose of CD19-ADC is about 90 µg/kg, about 120 µg/kg, about 140 to 160 µg/kg, or about 150 µg/kg.

88. The method according to any one of statements 83 to 87, wherein the subject has, or is suspected as having, or has been identified as being at risk of, or has received a diagnosis of a non-Hodgkin's Lymphoma, such as diffuse large B-cell lymphoma (DLBCL).

89. The method according to statement 57, wherein the chemotherapeutic agent is Cytarabine.

90. The method according to statement 89, wherein the Cytarabine is administered concurrently with the CD19-ADC.

91. The method according to either one of statements 89 or 90, wherein the CD19-ADC is administered on day 2 of each Q3W treatment cycle.

92. The method according to any one of statements 89 to 91, wherein the cytarabine is administered in a Q3W dosage regime.

93. The method according to statement 92, wherein the cytarabine is administered as 5 partial doses spread one partial dose per day on days 1 to 5 of each cycle.

94. The method according to statement 93, wherein each partial dose of cytarabine is 100 mg/m², 200 mg/m², 300 mg/m², or 400 mg/m².

95. The method according to any one of statements 89 to 94, wherein the subject has, or is suspected as having, or has been identified as being at risk of, or has received a diagnosis of a non-Hodgkin's Lymphoma, such as diffuse large B-cell lymphoma (DLBCL).

96. The method according to any one of statements 89 to 95, wherein the cytarabine is administered in further combination with rituximab as described in any one of statements 84 to 88.

97. The method according to statement 57 or statement 58, wherein the chemotherapeutic agent is administered to the subject before, at the same time, or after the CD19-ADC.

98. The method according to any preceding statement, wherein the CD19-ADC is administered in combination with a steroid.

99 The method according to statement 98, wherein a first dose of steroid is administered on the same day as the ADC.

100. The method according to statement 99, wherein the first dose of steroid is administered at least 2 hours before the ADC.

101. The method according to either one of statements 98 or 99, wherein a second dose of steroid is administered the day after the ADC.

102. The method according to statement 98, wherein a first dose of steroid is administered the day before the ADC.

103. The method according to statement 102, wherein a second dose of steroid is administered on the same day as the ADC.

104. The method according to statement 103, wherein the second dose of steroid is administered at least 2 hours before the ADC.

105. The method according to either one of statements 103 or 104 wherein a third dose of steroid is administered the day after the ADC.

106. The method according to any one of statements 98 to 105, wherein the steroid or steroid doses are administered only in conjunction with the first administration of ADC in each treatment cycle.

107. The method according to any one of statements 98 to 106, wherein the steroid is administered orally.

108. The method according to any one of statements 98 to 107, wherein each dose of steroid is 8 mg.

109. The method according to any one of statements 98 to 108, wherein each dose of steroid is 16 mg.

110. The method according to any one of statements 98 to 109, wherein each dose of steroid is administered as two equal, partial doses.

111. The method according to any one of statements 98 to 110, wherein each partial dose is 4 mg.

112. The method according to any one of statements 96 to 111, wherein each partial dose is 8 mg.

113. The method according to any one of statements 96 to 112, wherein the steroid is dexamethasone.

114. The method according to statement 98, wherein 4 mg or 8 mg dexamethasone is administered orally twice daily: (i) the day before ADC administration on week 1, day 1 of the treatment cycle, (ii) the day of ADC administration on week 1, day 1 of the treatment cycle, and (iii) the day after ADC administration on week 1, day 1 of the treatment cycle.

115. The method according to statement 98, wherein 4 mg or 8 mg dexamethasone is administered orally twice daily: (i) the day of ADC administration on week 1, day 1 of the treatment cycle, and (ii) the day after ADC administration on week 1, day 1 of the treatment cycle.

116. The method according to either one of statements 114 and 115, wherein the dexamethasone administered on the same day as the ADC is administered at least two hours before the ADC.

117. The method according to any one of statements 114 to 115, wherein the dexamethasone is administered only in conjunction with the first administration of ADC in each treatment cycle.

118. The method according to any preceding statement wherein the tapered and/or elongated dosage regime has lower toxicity than a single-dose dosage regime a dosage regime having constant dosage level and cycle length, optionally wherein the constant dose level and cycle length of the comparator regime is the same as the starting dose and starting length of the tapered and/or elongated regime.

119. The method according to statement 98, wherein the incidence of TEAE with the tapered and/or elongated dosage regime is no more than 50% of the incidence of TEAE in the constant dose level and cycle length regime.

120. The method according to statement 119, wherein the incidence of SAE with the tapered and/or elongated dosage regime is no more than 50% of the incidence of SAE in the constant dose level and cycle length regime.

121 The method according to statement 98, wherein the incidence of DLT with the tapered and/or elongated dosage regime is no more than 50% of the incidence of DLT in the constant dose level and cycle length regime.

122. The method according to any preceding statement wherein the tapered and/or elongated dosage regime has greater efficacy than a dosage regime having constant dosage level and cycle length, optionally wherein the constant dose level and cycle length of the comparator regime is the same as the starting dose and starting length of the tapered and/or elongated regime.

123. The method according to statement 122, wherein the proportion of subjects achieving at least PR with the tapered and/or elongated dosage regime is at least 150% of the proportion of subjects achieving at least a partial response [PR] in the constant dose level and cycle length regime.

124. The method according to any preceding statement, wherein the subject undergoes a neurological examination prior to treatment with the ADC.

125. The method according to any preceding statement, wherein the subject undergoes a neurological examination after administration of the ADC.

126. The method according to any preceding statement, wherein the subject undergoes a neurological examination after each administration of the ADC.

127. The method according to any preceding statement, wherein the subject undergoes a neurological examination if they experience a neurologic toxicity following administration of the ADC.

128. The method according to any one of statements 124 to 127, wherein the neurological examination includes tests of strength, sensation, and/or deep-tendon reflexes.

129. The method according to any preceding statement, wherein treatment with the ADC is reduced, suspended, or permanently discontinued if the subject has a neurological disorder or experiences a neurologic toxicity.

130. The method according to any preceding statement, wherein treatment with the ADC is reduced or suspended if the subject experiences a grade 1 neurologic toxicity.

131. The method according to any preceding statement, wherein treatment with the ADC is permanently discontinued if the subject experiences a grade 2 neurologic toxicity.

132. The method according to any one of statements 129 to 131, wherein treatment with the ADC is reduced by reducing the dose of ADC that is administered to the subject in each subsequent treatment cycle, and/or by increasing the length of each subsequent treatment cycle.

133. A method of selecting a subject for treatment by a method according to any one of statements 1 to 129, which method comprises determining if the subject has, or recently had, a neurologic disorder, wherein the subject is determined to be not suitable for treatment with the ADC if they have, or have recently had, a neurologic disorder.

134. A method of selecting a subject for treatment by a method according to any one of statements 1 to 132, which method comprises determining if the subject has, or recently had, an infection caused by a pathogen that may be associated with neurologic and/or immune-related disease; wherein the subject is determined to be not suitable for treatment with the ADC if they have, or have recently had, such an infection and/or immune-related disease.

135. The method according to any one of statements 127 to 134, wherein the neurologic disorder or neurological toxicity is polyradiculopathy, acute inflammatory demyelinating (AIDP), Guillain-Barré syndrome (GBS), myasthenia gravis, or a neurologic disorder that is linked to or is an early indicator of polyradiculitis, GBS, or myasthenia gravis, such as ascending sensory loss and/or motor weakness.

136. The method according to any one of statements 125 to 132, wherein the neurologic disorder or neurological toxicity is Guillain-Barré syndrome (GBS).

137. A method of reducing the toxicity and/or side effects associated with administration of a CD19-ADC to a subject, the method comprising administering the CD19-ADC according to the method of any preceding statement.

138. A method of increasing the treatment efficacy associated with administration of a CD19-ADC to a subject, the method comprising administering the CD19-ADC according to the method of any preceding statement.

139. A method of selecting a subject for treatment by a method according to any one of statements 1 to 138, which method comprises selecting for treatment subjects that express CD19 in a tissue of interest.

140. The method according to statement 139 wherein subjects are selected if at least 5% of cells in a sample of the tissue of interest express CD19.

141. The method according to either one of statements 139 and 140 wherein the tissue of interest is lymphoid tissue or tumour tissue.

142. The method according to any one of statements 139 to 141, wherein the subject has experienced a DLT in a constant dose and or constant cycle length dosage regime of a CD19-ADC.

143. A packaged pharmaceutical product comprising a CD19-ADC as defined in any one of statements 1 to 5, in combination with a label or insert advising that the CD19-ADC should be administered according to the method of any one of statements 1 to 92.

144. A kit comprising:
a first medicament comprising a CD19-ADC as defined in any one of statements 1 to 6; and, optionally,
a package insert or label comprising instructions for administration of the CD19-ADC according to the method of any one of statements 1 to 136.

145. A CD19-ADC as defined in any one of statements 1 to 6 for use in a method of any one of statements 1 to 136.

146. A pharmaceutical composition comprising a CD19-ADC as defined in any one of statements 1 to 6, optionally in combination with a pharmaceutically acceptable excipient, for use in a method of any one of statements 1 to 136.

147. Use of a CD19-ADC as defined in any one of statements 1 to 6 in the preparation of a medicament for use in a method of any one of statements 1 to 136.

Leukaemia

1. A method of treating a proliferative disease in a subject, said method comprising administering to a subject a CD19-ADC, wherein the CD19-ADC is administered to the subject in a fractionated dosage regime, and;
wherein the CD19-ADC comprises a conjugate of formula L-(D$^L$)$_p$, where D$^L$ is of formula I or II:

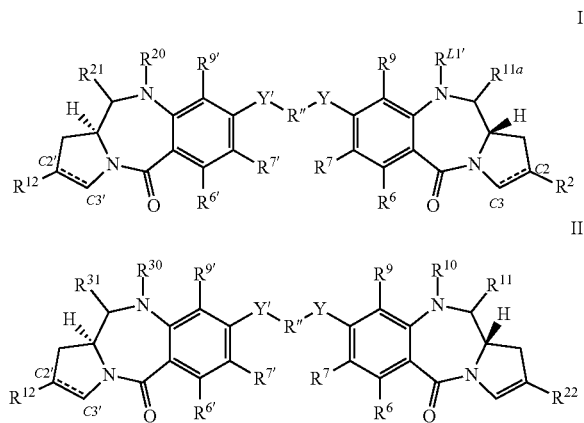

wherein:
L is an antibody (Ab) which is an antibody that binds to CD19;
when there is a double bond present between C2' and C3', R$^{12}$ is selected from the group consisting of:
(ia) C$_{5-10}$ aryl group, optionally substituted by one or more substituents selected from the group comprising:

halo, nitro, cyano, ether, carboxy, ester, $C_{1-7}$ alkyl, $C_{3-7}$ heterocyclyl and bis-oxy-$C_{1-3}$ alkylene;
(ib) $C_{1-5}$ saturated aliphatic alkyl;
(ic) $C_{3-6}$ saturated cycloalkyl;

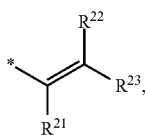
(id)

wherein each of $R^{21}$, $R^{22}$ and $R^{23}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5;

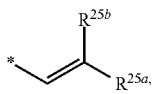
(ie)

wherein one of $R^{25a}$ and $R^{25b}$ is H and the other is selected from: phenyl, which phenyl is optionally substituted by a group selected from halo, methyl, methoxy; pyridyl; and thiophenyl; and

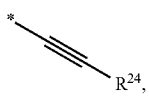
(if)

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;
when there is a single bond present between C2' and C3', $R^{12}$ is

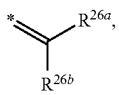

where $R^{26a}$ and $R^{26b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{26a}$ and $R^{26b}$ is H, the other is selected from nitrile and a $C_{1-4}$ alkyl ester;
$R^6$ and $R^9$ are independently selected from H, R, OH, OR, SH, SR, $NH_2$, NHR, NRR', nitro, $Me_3Sn$ and halo;
where R and R' are independently selected from optionally substituted $C_{1-12}$ alkyl, $C_{3-20}$ heterocyclyl and $C_{5-20}$ aryl groups;
$R^7$ is selected from H, R, OH, OR, SH, SR, $NH_2$, NHR, NHRR', nitro, $Me_3Sn$ and halo;
R" is a $C_{3-12}$ alkylene group, which chain may be interrupted by one or more heteroatoms, e.g. O, S, $NR^{N2}$ (where $R^{N2}$ is H or $C_{1-4}$ alkyl), and/or aromatic rings, e.g. benzene or pyridine;
Y and Y' are selected from O, S, or NH;

$R^{6'}$, $R^{7'}$, $R^{9'}$ are selected from the same groups as $R^6$, $R^7$ and $R^9$ respectively;
[Formula I]
$R^{L1'}$ is a linker for connection to the antibody (Ab);
$R^{11a}$ is selected from OH, $OR^A$, where $R^A$ is $C_{1-4}$ alkyl, and $SO_zM$, where z is 2 or 3 and M is a monovalent pharmaceutically acceptable cation;
$R^{20}$ and $R^{21}$ either together form a double bond between the nitrogen and carbon atoms to which they are bound or;
$R^{20}$ is selected from H and $R^C$, where $R^C$ is a capping group;
$R^{21}$ is selected from OH, $OR^A$ and $SO_zM$;
when there is a double bond present between C2 and C3, $R^2$ is selected from the group consisting of:
(ia) $C_{5-10}$ aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{1-3}$ alkylene;
(ib) $C_{1-5}$ saturated aliphatic alkyl;
(ic) $C_{3-6}$ saturated cycloalkyl;

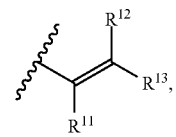
(id)

wherein each of $R^{11}$, $R^{12}$ and $R^{13}$ are independently selected from H, $C_{1-3}$ saturated alkyl, $C_{2-3}$ alkenyl, $C_{2-3}$ alkynyl and cyclopropyl, where the total number of carbon atoms in the $R^2$ group is no more than 5;

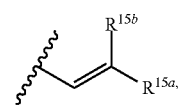
(ie)

wherein one of $R^{15a}$ and $R^{15b}$ is H and the other is selected from: phenyl, which phenyl is optionally substituted by a group selected from halo, methyl, methoxy; pyridyl; and thiophenyl; and

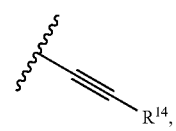
(if)

where $R^{14}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;
when there is a single bond present between C2 and C3, $R^2$ is

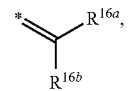

where $R^{16a}$ and $R^{16b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{16a}$ and $R^{16b}$ is H, the other is selected from nitrile and a $C_{1-4}$ alkyl ester;

[Formula II]

$R^{22}$ is of formula IIIa, formula IIIb or formula IIIc:

IIIa

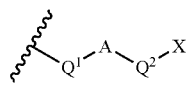
(a)

where A is a $C_{5-7}$ aryl group, and either
(i) $Q^1$ is a single bond, and $Q^2$ is selected from a single bond and $—Z—(CH_2)_n—$, where Z is selected from a single bond, O, S and NH and n is from 1 to 3; or
(ii) $Q^1$ is $—CH=CH—$, and $Q^2$ is a single bond;

IIIb

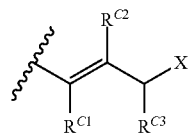
(b)

where;
$R^{C1}$, $R^{C2}$ and $R^{C3}$ are independently selected from H and unsubstituted $C_{1-2}$ alkyl;

IIIc

(c)

where Q is selected from $O—R^{L2'}$, $S—R^{L2'}$ and $NR^N—R^{L2'}$, and $R^N$ is selected from H, methyl and ethyl X is selected from the group comprising: $O—R^{L2'}$, $S—R^{L2'}$, $CO_2—R^{L2'}$, $CO—R^{L2'}$, $NH—C(=O)—R^{L2'}$, $NHNH—R^{L2'}$, $CONHNH—R^{L2'}$,

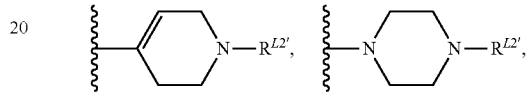

$NR^N R^{L2'}$, wherein $R^N$ is selected from the group comprising H and $C_{1-4}$ alkyl;

$R^{L2'}$ is a linker for connection to the antibody (Ab);

$R^{10}$ and $R^{11}$ either together form a double bond between the nitrogen and carbon atoms to which they are bound or;

$R^{10}$ is H and $R^{11}$ is selected from OH, $OR^A$ and $SO_zM$;

$R^{30}$ and $R^{31}$ either together form a double bond between the nitrogen and carbon atoms to which they are bound or;

$R^{30}$ is H and $R^{31}$ is selected from OH, $OR^A$ and $SO_zM$.

2. The method according to statement 1 wherein the CD19-ADC has the chemical structure:

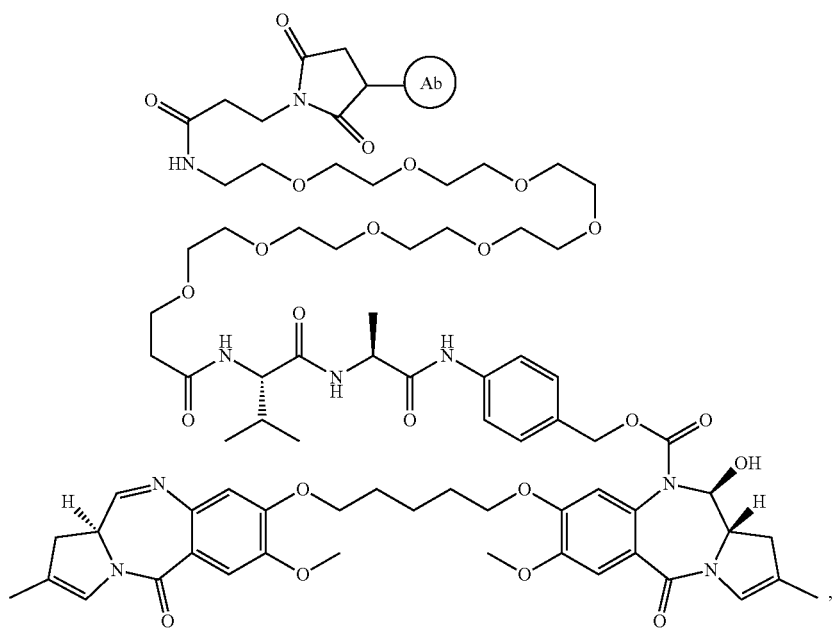

where the Ab is a CD19 antibody, and the DAR is between 1 and 8.

3. The method according to either one of statements 1 and 2 wherein Ab comprises a VH domain having the sequence of SEQ ID NO. 2 and a VL domain having the sequence of SEQ ID NO. 8.

4. The method according to any one of statements 1 to 3 wherein Ab comprises a heavy chain having sequences of SEQ ID NO. 13 and a light chain having the sequences of SEQ ID NO. 14.

5. The method according to any one of statements 1 to 4 wherein the CD19-ADC is ADCx19.

6. The method according to any preceding statement wherein the total dose of CD19-ADC administered during the treatment cycle is administered as a series of two or more partial doses during a treatment cycle.

7. The method according to any preceding statement wherein the partial doses of CD19 ADC are administered at regularly spaced intervals throughout the treatment cycle.

8. The method according to any preceding statement wherein a partial dose of CD19-ADC is administered to the subject once per week.

9. The method according to any preceding statement wherein the length of the treatment cycle is 3 weeks.

10. The method according to any preceding statement wherein the length of the treatment cycle is 6 weeks.

11. The method according to any preceding statement wherein a partial dose of the CD19-ADC is administered once a week in a 3-week treatment cycle.

12. The method according to any preceding statement wherein a partial dose of the CD19-ADC is administered on days 1, 8, and 15 of a 3-week treatment cycle.

13. The method according to any preceding statement wherein a total dose of about 10 µg/kg CD19-ADC is administered during the treatment cycle.

14. The method according to any preceding statement wherein a total dose of about 20 µg/kg CD19-ADC is administered during the treatment cycle.

15. The method according to any preceding statement wherein a total dose of about 30 µg/kg CD19-ADC is administered during the treatment cycle.

16. The method according to any preceding statement wherein a total dose of about 40 µg/kg CD19-ADC is administered during the treatment cycle.

17. The method according to any preceding statement wherein a total dose of about 50 µg/kg CD19-ADC is administered during the treatment cycle.

18. The method according to any preceding statement wherein a total dose of about 60 µg/kg CD19-ADC is administered during the treatment cycle.

19. The method according to any preceding statement wherein a total dose of about 70 µg/kg CD19-ADC is administered during the treatment cycle.

20. The method according to any preceding statement wherein a total dose of about 80 µg/kg CD19-ADC is administered during the treatment cycle.

21. The method according to any preceding statement wherein a total dose of about 90 µg/kg CD19-ADC is administered during the treatment cycle.

22. The method according to any preceding statement wherein a total dose of about 100 µg/kg CD19-ADC is administered during the treatment cycle.

23. The method according to any preceding statement wherein a total dose of about 120 µg/kg CD19-ADC is administered during the treatment cycle.

24. The method according to any preceding statement wherein a total dose of about 140 to 160 µg/kg, such as about 150 µg/kg CD19-ADC is administered during the treatment cycle.

25. The method according to any preceding statement wherein a total dose of about 200 µg/kg CD19-ADC is administered during the treatment cycle.

26. The method according to any preceding statement wherein a total dose of about 250 µg/kg CD19-ADC is administered during the treatment cycle.

27. The method according to any preceding statement wherein a total dose of about 300 µg/kg CD19-ADC is administered during the treatment cycle.

28. The method according to any preceding statement wherein a total dose of about 350 µg/kg CD19-ADC is administered during the treatment cycle.

29. The method according to any preceding statement wherein a total dose of about 400 µg/kg CD19-ADC is administered during the treatment cycle.

30. The method according to any preceding statement wherein a total dose of about 450 µg/kg CD19-ADC is administered during the treatment cycle.

31. The method according to any preceding statement wherein a total dose of about 500 µg/kg CD19-ADC is administered during the treatment cycle.

32. The method according to any preceding statement wherein a total dose of about 550 µg/kg CD19-ADC is administered during the treatment cycle.

33. The method according to any preceding statement wherein a total dose of about 600 µg/kg CD19-ADC is administered during the treatment cycle.

34. The method according to any preceding statement wherein a total dose of 1 to 10 µg/kg CD19-ADC is administered during the treatment cycle.

35. The method according to any preceding statement wherein a total dose of 11 to 20 µg/kg CD19-ADC is administered during the treatment cycle.

36. The method according to any preceding statement wherein a total dose of 21 to 30 µg/kg CD19-ADC is administered during the treatment cycle.

37. The method according to any preceding statement wherein a total dose of 31 to 40 µg/kg CD19-ADC is administered during the treatment cycle.

38. The method according to any preceding statement wherein a total dose of 41 to 50 µg/kg CD19-ADC is administered during the treatment cycle.

39. The method according to any preceding statement wherein a total dose of 51 to 60 µg/kg CD19-ADC is administered during the treatment cycle.

40. The method according to any preceding statement wherein a total dose of 61 to 70 µg/kg CD19-ADC is administered during the treatment cycle.

41. The method according to any preceding statement wherein a total dose of 71 to 80 µg/kg CD19-ADC is administered during the treatment cycle.

42. The method according to any preceding statement wherein a total dose of 81 to 90 µg/kg CD19-ADC is administered during the treatment cycle.

43. The method according to any preceding statement wherein a total dose of 91 to 100 µg/kg CD19-ADC is administered during the treatment cycle.

44. The method according to any preceding statement wherein a total dose of 101 to 120 µg/kg CD19-ADC is administered during the treatment cycle.

45. The method according to any preceding statement wherein a total dose of 121 to 140 µg/kg CD19-ADC is administered during the treatment cycle.

46. The method according to any preceding statement wherein a total dose of 141 to 160 µg/kg CD19-ADC is administered during the treatment cycle.

47. The method according to any preceding statement wherein a total dose of 161 to 180 µg/kg CD19-ADC is administered during the treatment cycle.

48. The method according to any preceding statement wherein a total dose of 181 to 200 µg/kg CD19-ADC is administered during the treatment cycle.

49. The method according to any preceding statement wherein a total dose of 201 to 220 µg/kg CD19-ADC is administered during the treatment cycle.

50. The method according to any preceding statement wherein a total dose of 221 to 240 µg/kg CD19-ADC is administered during the treatment cycle.

51. The method according to any preceding statement wherein a total dose of 241 to 260 µg/kg CD19-ADC is administered during the treatment cycle.

52. The method according to any preceding statement wherein a total dose of 261 to 280 µg/kg CD19-ADC is administered during the treatment cycle.

53. The method according to any preceding statement wherein a total dose of 281 to 300 µg/kg CD19-ADC is administered during the treatment cycle.

54. The method according to any preceding statement wherein a total dose of 301 to 320 µg/kg CD19-ADC is administered during the treatment cycle.

55. The method according to any preceding statement wherein a total dose of 321 to 340 µg/kg CD19-ADC is administered during the treatment cycle.

56. The method according to any preceding statement wherein a total dose of 341 to 360 µg/kg CD19-ADC is administered during the treatment cycle.

57. The method according to any preceding statement wherein a total dose of 361 to 380 µg/kg CD19-ADC is administered during the treatment cycle.

58. The method according to any preceding statement wherein a total dose of 381 to 400 µg/kg CD19-ADC is administered during the treatment cycle.

59. The method according to any preceding statement wherein a total dose of 401 to 420 µg/kg CD19-ADC is administered during the treatment cycle.

60. The method according to any preceding statement wherein a total dose of 421 to 440 µg/kg CD19-ADC is administered during the treatment cycle.

61. The method according to any preceding statement wherein a total dose of 441 to 460 µg/kg CD19-ADC is administered during the treatment cycle.

62. The method according to any preceding statement wherein a total dose of 461 to 480 µg/kg CD19-ADC is administered during the treatment cycle.

63. The method according to any preceding statement wherein a total dose of 481 to 500 µg/kg CD19-ADC is administered during the treatment cycle.

64. The method according to any preceding statement wherein a total dose of 501 to 520 µg/kg CD19-ADC is administered during the treatment cycle.

65. The method according to any preceding statement wherein a total dose of 521 to 540 µg/kg CD19-ADC is administered during the treatment cycle.

66. The method according to any preceding statement wherein a total dose of 541 to 560 µg/kg CD19-ADC is administered during the treatment cycle.

67. The method according to any preceding statement wherein a total dose of 561 to 580 µg/kg CD19-ADC is administered during the treatment cycle.

68. The method according to any preceding statement wherein a total dose of 581 to 600 µg/kg CD19-ADC is administered during the treatment cycle.

69. The method according to any preceding statement wherein the partial dose is about 10 µg/kg.

70. The method according to any preceding statement wherein the partial dose is about 20 µg/kg.

71. The method according to any preceding statement wherein the partial dose is about 30 µg/kg.

72. The method according to any preceding statement wherein the partial dose is about 40 µg/kg.

The method according to any preceding statement wherein the partial dose is about 50 µg/kg.

74. The method according to any preceding statement wherein the partial dose is about 60 µg/kg.

75. The method according to any preceding statement wherein the partial dose is about 70 µg/kg.

76. The method according to any preceding statement wherein the partial dose is about 80 µg/kg.

77. The method according to any preceding statement wherein the partial dose is about 90 µg/kg.

78. The method according to any preceding statement wherein the partial dose is about 100 µg/kg.

79. The method according to any preceding statement wherein the partial dose is about 110 µg/kg.

80. The method according to any preceding statement wherein the partial dose is about 120 µg/kg.

81. The method according to any preceding statement wherein the partial dose is about 130 µg/kg.

82. The method according to any preceding statement wherein the partial dose is about 140 µg/kg.

The method according to any preceding statement wherein the partial dose is about 150 µg/kg.

84. The method according to any preceding statement wherein the partial dose is about 160 µg/kg.

85. The method according to any preceding statement wherein the partial dose is about 170 µg/kg.

86. The method according to any preceding statement wherein the partial dose is about 180 µg/kg.

87. The method according to any preceding statement wherein the partial dose is about 190 µg/kg.

88. The method according to any preceding statement wherein the partial dose is about 200 µg/kg.

89. The method according to any preceding statement wherein the partial dose is 1 to 10 µg/kg.

90. The method according to any preceding statement wherein the partial dose is 11 to 20 µg/kg.

91. The method according to any preceding statement wherein the partial dose is 21 to 30 µg/kg.

92. The method according to any preceding statement wherein the partial dose is 31 to 40 µg/kg.

93. The method according to any preceding statement wherein the partial dose is 41 to 50 µg/kg.

94. The method according to any preceding statement wherein the partial dose is 51 to 60 µg/kg.

95. The method according to any preceding statement wherein the partial dose is 61 to 70 µg/kg.

95a. The method according to any preceding statement wherein the partial dose is about 40 to 60 µg/kg, such as about 45 to 55 µg/kg.

The method according to any preceding statement wherein the partial dose is 71 to 80 µg/kg.

97. The method according to any preceding statement wherein the partial dose is 81 to 90 µg/kg.

98. The method according to any preceding statement wherein the partial dose is 91 to 100 µg/kg.

99. The method according to any preceding statement wherein the partial dose is 101 to 110 µg/kg.

100. The method according to any preceding statement wherein the partial dose is 111 to 120 µg/kg.

101. The method according to any preceding statement wherein the partial dose is 121 to 130 µg/kg.

102. The method according to any preceding statement wherein the partial dose is 131 to 140 µg/kg.

103. The method according to any preceding statement wherein the partial dose is 141 to 150 µg/kg.

104. The method according to any preceding statement wherein the partial dose is 151 to 160 µg/kg.

105. The method according to any preceding statement wherein the partial dose is 161 to 170 µg/kg.

106 The method according to any preceding statement wherein the partial dose is 171 to 180 µg/kg.

107. The method according to any preceding statement wherein the partial dose is 181 to 190 µg/kg.

108. The method according to any preceding statement wherein the partial dose is 191 to 200 µg/kg.

109. The method according to any preceding statement wherein the amount of CD19-ADC in each partial dose is the same.

110. The method according to any preceding statement wherein the proliferative disease is characterised by the presence of a neoplasm comprising CD19+ve cells 111. The method according to any preceding statement wherein the subject has been diagnosed as having the proliferative disease prior to the start of treatment with the CD19-ADC.

112. The method according to statement 111, wherein the disease is CD19+ALL.

113. The method according to any preceding statement wherein the method comprises the step of selecting a subject for treatment based on expression of CD19.

114. The method according to statement 113, wherein a subject is selected if at least 5% of neoplasm cells express CD19.

115. The method according to any preceding statement wherein the proliferative disease is non-Hodgkin's Lymphoma, including diffuse large B-cell lymphoma (DLBCL), follicular lymphoma, (FL), Mantle Cell lymphoma (MCL), chronic lymphatic lymphoma (CLL), Waldenstroms Microglobulinemia, Burkitt's lymphoma, and Marginal Zone B-cell lymphoma (MZBL), and leukemias such as Hairy cell leukaemia (HCL), Hairy cell leukaemia variant (HCL-v), and Acute Lymphoblastic Leukaemia (ALL) such as Philadelphia chromosome-positive ALL (Ph+ALL) or Philadelphia chromosome-negative ALL (Ph-ALL).

116. The method according to any preceding statement wherein the proliferative disease is CD19+ALL.

117. The method according to any preceding statement wherein the proliferative disease is resistant, relapsed or refractory.

118. The method according to any preceding statement wherein the subject is human.

119. The method according to any preceding statement wherein the CD19-ADC is administered intravenously.

120. The method according to any preceding claim further comprising administering a chemotherapeutic agent in combination with the CD19-ADC.

121. The method according to statement 120, wherein the chemotherapeutic agent is administered to the subject before, at the same time, or after the CD19-ADC.

122. The method according to any preceding statement, wherein the CD19-ADC is administered in combination with a steroid.

123. The method according to statement 122, wherein a first dose of steroid is administered on the same day as the ADC.

124. The method according to statement 123, wherein the first dose of steroid is administered at least 2 hours before the ADC.

125. The method according to either one of statements 123 or 124, wherein a second dose of steroid is administered the day after the ADC.

126. The method according to statement 122, wherein a first dose of steroid is administered the day before the ADC.

127. The method according to statement 126, wherein a second dose of steroid is administered on the same day as the ADC.

128. The method according to statement 127, wherein the second dose of steroid is administered at least 2 hours before the ADC.

129. The method according to either one of statements 127 or 128, wherein a third dose of steroid is administered the day after the ADC.

130. The method according to any one of statements 122 to 129, wherein the steroid or steroid doses are administered only in conjunction with the first administration of ADC in each treatment cycle.

131. The method according to any one of statements 122 to 130, wherein the steroid is administered orally.

132. The method according to any one of statements 122 to 131, wherein each dose of steroid is 8 mg.

133. The method according to any one of statements 122 to 132, wherein each dose of steroid is 16 mg.

134. The method according to any one of statements 122 to 133, wherein each dose of steroid is administered as two equal, partial doses.

135. The method according to any one of statements 122 to 134, wherein each partial dose is 4 mg.

136. The method according to any one of statements 122 to 135 wherein each partial dose is 8 mg.

137. The method according to any one of statements 122 to 136, wherein the steroid is dexamethasone.

138 The method according to statement 122, wherein 4 mg dexamethasone is administered orally twice daily: (i) the day before ADC administration on week 1, day 1 of the treatment cycle, (ii) the day of ADC administration on week 1, day 1 of the treatment cycle, and (iii) the day after ADC administration on week 1, day 1 of the treatment cycle.

139. The method according to statement 122, wherein 4 mg dexamethasone is administered orally twice daily: (i) the day of ADC administration on week 1, day 1 of the treatment cycle, and (ii) the day after ADC administration on week 1, day 1 of the treatment cycle.

140. The method according to either one of statements 138 and 139, wherein the dexamethasone administered on the same day as the ADC is administered at least two hours before the ADC.

141 The method according to any one of statements 138 to 140, wherein the dexamethasone is administered only in conjunction with the first administration of ADC in each treatment cycle.

142. The method according to any preceding statement wherein the fractionated dosage regime has lower toxicity than a single-dose dosage regime having the same total dose administered and length of treatment cycle.

143. The method according to statement 142, wherein the incidence of TEAE with the fractionated dosage regime is no more than 50% of the incidence of TEAE in the single-dose regime.

144. The method according to statement 142, wherein the incidence of SAE with the fractionated dosage regime is no more than 50% of the incidence of SAE in the single-dose regime.

145 The method according to statement 142, wherein the incidence of DLT with the fractionated dosage regime is no more than 50% of the incidence of DLT in the single-dose regime.

146. The method according to any preceding statement wherein the fractionated dosage regime has greater efficacy than a single-dose dosage regime having the same total dose administered and length of treatment cycle.

147. The method according to statement 146, wherein the proportion of subjects achieving at least PR with the fractionated dosage regime is at least 150% of the proportion of subjects achieving at least a partial response [PR] in the single dose regime.

148. A method of reducing the toxicity and/or side effects associated with administration of a CD19-ADC to a subject, the method comprising administering the CD19-ADC according to the method of any preceding statement.

149. A method of increasing the treatment efficacy associated with administration of a CD19-ADC to a subject, the method comprising administering the CD19-ADC according to the method of any preceding statement.

150. A method of selecting a subject for treatment by a method according to any one of statements 1 to 141, which method comprises selecting for treatment subjects that express CD19 in a tissue of interest.

151. The method according to statement 150 wherein subjects are selected if at least 5% of cells in a sample of the tissue of interest express CD19.

152. The method according to either one of statements 150 and 151 wherein the tissue of interest is lymphoid tissue or tumour tissue.

153. The method according to any one of statements 150 to 152, wherein the subject has experienced a DLT in a single-dose dosage regime of a CD19-ADC.

154. A packaged pharmaceutical product comprising a CD19-ADC as defined in any one of statements 1 to 5, in combination with a label or insert advising that the CD19-ADC should be administered according to the method of any one of statements 1 to 151.

155. A kit comprising:
 a first medicament comprising a CD19-ADC as defined in any one of statements 1 to 5; and, optionally,
 a package insert or label comprising instructions for administration of the CD19-ADC according to the method of any one of statements 1 to 151.

156. A CD19-ADC as defined in any one of statements 1 to 5 for use in a method of any one of statements 1 to 151.

157. A pharmaceutical composition comprising a CD19-ADC as defined in any one of statements 1 to 5, optionally in combination with a pharmaceutically acceptable excipient, for use in a method of any one of statements 1 to 151.

158. Use of a CD19-ADC as defined in any one of statements 1 to 5 in the preparation of a medicament for use in a method of any one of statements 1 to 151.

EXAMPLES

Example 1: Pharmokinetics of ADCx19 in ALL Patients

At least one dose of ADCx19 was administered to 48 patients with Relapsed or Refractory B-cell Lineage Non Hodgkin Lymphoma (B-NHL) (4 at 15 µg/kg, 4 at 30 µg/kg, 4 at 60 µg/kg, 5 at 90 µg/kg, 12 at 120 µg/kg, 3 at 150 µg/kg and 17 at 200 µg/kg). Cohorts at 120 µg/kg and 200 µg/kg were expanded to further explore the early efficacy signals seen at those dose levels.

Emerging safety, pharmacokinetic and efficacy data suggest that repetitive dosing every three weeks is not well tolerated or necessary at doses of 120 µg/kg and higher. Twelve patients have been treated at 120 µg/kg (10 DLBCL, 1 FL and 1 MCL) with 4 patients attaining complete remission (CR) and 2 partial remission (PR). The 6 responding patients have received 3-7 infusions of ADCx19 with 4 of these patients having at least one dose delay due to adverse events (fatigue (2), oedema (3), muscle pain (2), rash (1), Elevated GGT and alkaline phosphatase (1)). Two patients were discontinued from treatment due to adverse events in this cohort (both had attained CR).

At 150 µg/kg, the three initial patients received either 2 or 3 cycles of ADCTx19 before side effects necessitated dose delay which eventually led to removal from the study since the toxicities were slow to resolve.

The first six evaluable patients treated on the 200 µg/kg cohort with dose administered every three weeks attained CR(5) or PR(1) on first restaging scans at the end of Cycle 2 (after second dose). However, all patients had some evidence of toxicity at the end of Cycle 2 (4 patients) or cycle 3 (1 patient). The pharmacokinetic profiles for the first two cycles for the initial 3 patients treated on the 200 µg/kg cohort indicated that the AUC and Cmax at the 200 µg/kg dose level are significantly higher than seen at lower doses. The trough levels at the end of Cycle 1 appear to be in the range of 500-1000 ng/ml.

In view of the emerging safety profile, it is proposed to modify the dosage regimes for future subjects at doses of 120 µg/kg or higher so that they are tapered and/or elongated dosage regimes as described herein. In particular, the following tapered and elongated dosage regimes will be utilised:

A. 120 µg/kg: Dosing every 3 weeks for 2 cycles. Patients with at least SD after the second cycle continue treatment at a reduced dose of 60 µg/kg q6 weeks, beginning 6 weeks after Cycle 2 infusion.
 B. 150 µg/kg: Dosing every 3 weeks for 2 cycles. Patients with at least SD after the second cycle continue treatment at a reduced dose of 60 µg/kg q6 weeks, beginning 6 weeks after Cycle 2 infusion.
 C. 200 µg/kg: Dosing every 6 weeks for 2 cycles. For patients with at least SD 6 weeks after Cycle 2, continue treatment at a reduced dose of 60 µg/kg q6 weeks, beginning 6 weeks after Cycle 2 infusion.
 D. 200 µg/kg: Dosing every 6 weeks. For patients with at least SD 6 weeks after Cycle 1, continue treatment at a reduced dose of 60 µg/kg every 6 weeks beginning 6 weeks after Cycle 1 infusion.
 E. 150 µg/kg: Dosing every 3 weeks for 2 cycles. Patients with at least SD after the second cycle continue treatment at a reduced dose of 75 µg/kg q3 weeks, beginning 3 weeks after Cycle 2 infusion.

The full clinical study protocol for the 3-week treatment cycle with a single-dose administered on day 1 is publically available at www.clinical trials.gov, having the ClinicalTrials.gov unique identifier: NCT02669017 (25 Apr. 2017 update).

Example 2: Synopsis of Tapered and/or Elongated Dosage Protocol

Indication

Patients with relapsed or refractory B-cell lineage non-Hodgkin Lymphoma (B-NHL) who have failed, or are intolerant to, any established therapy; or for whom no other treatment options are available, in the opinion of the Investigator.

The Dose Escalation Steering Committee (DESC) will determine which histologic sub-types will be investigated in Part 2 of the study based on the emerging efficacy and tolerability profile from part 1.

B-cell NHL defined as:
Diffuse large B-cell lymphoma (DLBCL)
Follicular lymphoma (FL)
Chronic lymphocytic leukaemia (CLL)
Mantle cell lymphoma (MCL)
Marginal Zone B-cell Lymphoma (MZBCL)
Burkitt's lymphoma (BL)
Lymphoplasmacytic lymphoma (Waldenstrom macroglobulinemia [WM]).

Objectives

Primary Objectives:
Evaluate the safety and tolerability, and determine, as appropriate, the maximum tolerated dose (MTD) of ADCx19 in patients with relapsed or refractory B-cell lineage NHL (Part 1).
Determine the recommended dose(s) of ADCx19 for Part 2 (expansion).
Evaluate the safety and tolerability of ADCx19 in Part 2 (expansion) at the dose level(s) recommended in Part 1.

Secondary Objectives:
Evaluate the clinical activity of ADCx19 as measured by overall response rate (ORR), duration of response (DOR), progression-free survival (PFS), and overall survival (OS).
Characterize the pharmacokinetic (PK) profile of ADCx19 (total antibody; drug to-antibody ratio [DAR] ≥0), PBD-conjugated antibody (DAR 1), and free warhead.
Evaluate anti-drug antibodies (ADAs) in blood before, during, and after treatment with ADCx19.

Efficacy Assessment

Disease assessments will be conducted within 6 days prior to Day 1 of Cycles 3 and 5 and thereafter every third cycle (i.e., Cycles 8, 11, 14, etc.), until disease progression, or more frequently, if clinically indicated. The same methods used at Screening which identify sites of disease should be used uniformly for all subsequent assessments. If PET-CT is positive, subsequent diagnostic CT and MRI are not needed unless clinically indicated. PET-CT is not required if a PET-CT examination at Screening was negative.

For patients who have reduced dosing frequency and are following a 6 week schedule, disease assessments should occur approximately 6 weeks and 12 weeks after Cycle 1 Day 1, and thereafter at least every 12 weeks. It is understood that there will be a ±6 day window for restaging of these patients.

The patient's response to treatment will be determined by the Investigator as complete response (CR), partial response (PR), stable disease (SD), or progressive disease (PD), based on the 2014 Lugano Classification Criteria.

PK Assessment

The PK profile of ADCT-402 (total antibody; DAR≥0), PBD-conjugated antibody (DAR≥1), and free warhead SG3199 will be assessed using measures from validated bioanalytical methods. The PK profile will include determination of standard PK parameters (e.g., maximum concentration [Cmax], time to Cmax [Tmax]).

The following pharmacodynamic and other exploratory assessments will be performed at various time points in the study:

Immunohistochemistry (archival tumor tissue or pretreatment tumor biopsies in consenting patients) for CD19 protein expression
Level of ADAs against ADCx19 in serum.
Analysis of peripheral WBC populations and CD marker panel expression (CD19, CD20, CD21, CD22), before, during, and after treatment with ADCx19 (US only).
Serum concentrations of ADCx19 and free warhead will be determined. The QTc interval will also be measured.

Safety Assessment

Safety will be assessed based on the evaluation of adverse events (AEs), serious AEs (SAEs), treatment discontinuations due to AEs, dose limiting toxicity(s) (DLTs), periodic 12-lead electrocardiogram (ECG) recordings, physical examinations, vital signs measurements, ECOG performance status, and haematology, coagulation panel and pregnancy testing (for women of child-bearing potential), biochemistry, and urinalysis test results obtained at various timepoints during the study. Adverse events will be graded according to CTCAE Version 4.0 (v4.03, published Jun. 14, 2010; NIH Publication No. 09-5410).

Product Dosage and Mode of Administration

ADCx19 is a sterile formulation containing PBD-conjugated humanized monoclonal IgG1 antibody (DAR 1), humanized monoclonal IgG1 antibody (DAR=0), and SG3249. It is provided pre-formulated in 10 mL single-use, glass vials containing approximately 16 mg ADCx19 per vial (deliverable volume 3.2 mL, with an additional 0.3 mL overfill at 5 mg/mL). Patients will receive a 1-hour intravenous (IV) infusion of ADCx19 on Day 1 of Cycle 1. If ADCx19 is well tolerated after the first infusion, the infusion duration may be shortened to 30 minutes for subsequent cycles for that patient, at the Investigator's discretion.

Dose Escalation Design

In Part 1, patients will be assigned to treatment with ADCT-402 at escalating doses according to a 3+3 study design. The initial dose of ADCT-402 will be 15 µg/kg (Dose Level 1), and the highest allowed dose will be 300 µg/kg.

Further dose levels and schedules evaluated include the following:

A. 120 µg/kg: Dosing every 3 weeks for 2 cycles. Patients with at least SD after the second cycle continue treatment at a reduced dose of 60 µg/kg q6 weeks, beginning 6 weeks after Cycle 2 infusion.

B. 150 µg/kg: Dosing every 3 weeks for 2 cycles. Patients with at least SD after the second cycle continue treatment at a reduced dose of 60 µg/kg q6 weeks, beginning 6 weeks after Cycle 2 infusion.

C. 200 µg/kg: Dosing every 6 weeks for 2 cycles. For patients with at least SD 6 weeks after Cycle 2, continue treatment at a reduced dose of 60 µg/kg q6 weeks, beginning 6 weeks after Cycle 2 infusion.

D. 200 µg/kg: Dosing every 6 weeks. For patients with at least SD 6 weeks after Cycle 1, continue treatment at a reduced dose of 60 µg/kg every 6 weeks beginning 6 weeks after Cycle 1 infusion.

E. 150 µg/kg: Dosing every 3 weeks for 2 cycles. Patients with at least SD after the second cycle continue treatment at a reduced dose of 60 µg/kg q6 weeks, beginning 6 weeks after Cycle 2 infusion.

The first patient enrolled into the study at 15 µg/kg (Dose Level 1) must be observed for 7 days for occurrence of AEs prior to treating the second patient in the study. The DLT observation period for dose escalation is 1 cycle.

For each dose level, if none of the first 3 patients at that level experiences a DLT, new patients may be entered at the next higher dose level. If 1 of 3 patients experiences a DLT, up to 3 more patients are to be treated at that same dose level. If none of the additional 3 patients at that dose level experiences a DLT, new patients may then be entered at the next higher dose level. However, if 1 or more of the additional 3 patients experiences a DLT, then no further patients are to be started at that dose level and the preceding dose is identified as the MTD. The MTD is therefore defined as the highest dose level at which none of the first 3 treated patients, or no more than 1 of the first 6 treated patients, experiences a DLT.

The study will be continuously monitored for safety and early stopping for successful identification of the MTD.

Dose Expansion Design

In Part 2, (expansion), patients will be assigned to dose level(s) and/or schedule(s) of ADCT-402 identified in Part 1 based on evolving safety, efficacy and pharmacokinetic data.

The population in Part 2 expansion may be restricted to specific histologies based on both signals of activity and the safety observed in Part 1.

Further, dose levels and schedules evaluated in Part 2 may include the regimes A, B, C. and D as described for Part 1, above.

Example 3: Summary of ADCx19 Treatment Safety and Efficacy Studies

Study Design

Concentrations of PBD-conjugated Ab in serum were determined using a validated electrochemiluminescence immunoassay. Data were analyzed by population PK methodology using NONMEM (version 7.3, first-order conditional estimation).

The base PK analysis employed the log-transformed both sides approach with a 2-compartment open model and zero-order infusion rate. Area under the curve (AUC) values were estimated from individual patient Bayesian post hoc predictions.

The influence of various covariate factors on PK variability was assessed and included age, gender, race, body surface area (BSA), body mass index, weight, albumin, alanine aminotransferase, aspartate aminotransferase, bilirubin, creatinine clearance, and haemoglobin (Hb).

PK exposure trends with maximum severity of early (Cycle 1) and later (all cycles) TEAEs for any grade TEAEs, anemia, platelets, neutrophils, Hb, fatigue, oedema, and pleural effusion were graphically explored.

Apparent trends were quantitatively assessed with logistic regression relating the probability of the following binary outcome variables with AUC and demographic factors (age, sex, weight, BSA, and maximum Eastern Cooperative Oncology Group status):

Grade ≥3 maximum severity TEAE
Grade ≥3 platelet decrease
Grade ≥1 oedema or pleural effusion.

Associations of dose and PK with maximum change from baseline tumor size were determined to identify potential relationships between exposure and activity (at least 50% reduction; complete response and partial response).

Results

Patient Characteristics

Data for 77 patients (53 men, 24 women), comprising 1138 observations, were included in the population PK model.

Final Population PK Model

Final population PK model parameters are provided in the Table 4 below.

There was a strong correlation between observed and estimated serum drug concentrations. Exposure and associated magnitude of intersubject variability increased with dose. Apparent terminal half-life values were long but moderately variable Modest drug accumulation was seen with repeated dosing.

BSA significantly affected volume of distribution.

No other significant covariates were identified.

TABLE 4

| Parameter (units) | Typical Value | SE (CV %) |
|---|---|---|
| CL (L/hr) | 0.0155 | 15.5 |
| Vc (L) | 4.37 | 2.1 |
| Q (L/hr) | 0.0322 | 36 |
| VP (L) | 5.41 | 37 |
| Residual error (CV %) | 41.8 | 0.5 |
| SHARE | 0.102 | 31 |
| Effect of BSA on Vc | 1.69 | 5.2 |
| Effect of BSA on Vp | 7.86 | 21.4 |
| IIV CL | 81.9 | 17.6 |
| IIV Q1 | 177 | 11.4 |
| IIV Vp | 144 | 12.6 |

BSA, body surface area;
CL, systemic clearance;
CV, coefficient of variation;
IIV, interindividual variability of respective pharmacokinetic term;
Q1, intercompartmental clearance;
SE, standard error;
Vc, central volume of distribution;
Vp, peripheral volume of distribution.

Relationship Between Exposure and Safety

Increased exposure (AUC) of PBD-conjugated Ab was associated with probability of Grade platelet decrease in Cycle 1 (p=0.0067) and any TEAE Grade during Cycle 1 and all cycles (both; p=0.031) (see Table 5 below). For any TEAEs Grade 3, men appeared to be more sensitive than women. A visual trend of increased AUC with probability of Grade oedema or pleural effusion was apparent.

TABLE 5

| Potential | | | Dose cohort (µg/kg) | | | | | |
|---|---|---|---|---|---|---|---|---|
| | | | 15 | 30 | 60 | 90 | 120 | 200 |
| | | | Median predicted AUC (µg*/L)[a] | | | | | |
| relationships identified | Model parameters | p-value[b] | 14820 | 31850 | 68060 | 124100 | 245400 | 517000 |
| | | | Mean predicted probability | | | | | |
| Platelet decrease Grade ≥3 Cycle 1[c] | AUC Cycle 1 | 0.0067 | 0.006 | 0.006 | 0.007 | 0.011 | 0.023 | 0.11 |

TABLE 5-continued

| Potential relationships identified | Model parameters | p-value[b] | Dose cohort (μg/kg) | | | | | |
|---|---|---|---|---|---|---|---|---|
| | | | 15 | 30 | 60 | 90 | 120 | 200 |
| | | | Median predicted AUC (μg*/L)[a] | | | | | |
| | | | 14820 | 31850 | 68060 | 124100 | 245400 | 517000 |
| | | | Mean predicted probability | | | | | |
| Platelet decrease Grade ≥3 all cycles | Mean AUC | 0.068 | 0.086 | 0.089 | 0.093 | 0.10 | 0.12 | 0.18 |
| Edema/pleural effusion Grade ≥1 all cycles | Mean AUC | 0.18 | 0.18 | 0.18 | 0.19 | 0.21 | 0.24 | 0.33 |
| TEAE Grade ≥3 Cycle 1[c] | AUC Cycle 1 | 0.031 | 0.074 | 0.078 | 0.086 | 0.10 | 0.14 | 0.26 |
| TEAE Grade ≥3 all cycles | Mean AUC, gender = M | 0.031 | 0.49 | 0.49 | 0.50 | 0.53 | 0.57 | 0.66 |
| TEAE Grade ≥3 all cycles | Mean AUC, gender = F | 0.031 | 0.25 | 0.26 | 0.27 | 0.28 | 0.32 | 0.41 |

Relationship Between Exposure and Efficacy

Increased dose of ADCx19 was significantly associated with increased probability of objective response (p=0.0439).

Increased exposure (AUC) of PBD-conjugated Ab was significantly associated with increased probability of objective response (p=0.0292).

Conclusions

The PK profile of PBD-conjugated Ab after administration of ADCx19 was described using a linear 2-compartment model.

BSA was a significant covariate of volume of distribution

Significant positive correlations were observed between PBD-conjugated Ab exposure (AUC) and incidence of Grade TEAEs (Cycle 1 and all cycles), and Grade platelet decrease in Cycle 1:

Frequency of Grade TEAEs were higher with protracted doses; limiting the number of cycles administered will control the rate of severe adverse events For severe adverse events, men may be more sensitive than women A relevant trend was apparent between AUC and Grade oedema or pleural effusion.

Interim efficacy assessment indicated significant dose-response and exposure-response relationships for ADCx19 when administered with a q3w schedule.

Example 4: Efficacy of ADCx19 Treatment in Mouse Xenograft In Vivo Model

Subcutaneous Ramos-e222 Model

Female severe combined immunodeficient mice (Fox Chase SCID®, C.B-17/Icr-Prkdcscid, Charles River) were eight weeks old, with a body weight (BW) range of 17.5 to 25.6 grams on Day 1 of the study.

On the day of implant, Ramos cells were harvested during log phase growth and resuspended in phosphate buffered saline. Xenografts were initiated by subcutaneously implanting 1×107 Ramos cells (0.1 mL suspension) into the right flank of each test animal and tumors were monitored as their volumes approached the target range of 100 to 150 mm3. Tumors were measured in two dimensions using callipers, and volume was calculated using the formula:

$$\text{Tumor Volume (mm3)} = w^2 \times l/2$$

where w=width and l=length, in mm, of the tumor. Tumor weight may be estimated with the assumption that 1 mg is equivalent to 1 mm3 of tumor volume.

Thirteen days after tumor implantation, designated as Day 1 of the study, the animals were sorted into groups each consisting of ten mice with individual tumor volumes ranging from 108 to 172 mm³ and group mean tumor volumes of 120 mm³. All agents were administered intravenously (i.v.) via tail vein injection once on Day 1 in a dosing volume of 0.2 mL per 20 grams of body weight (10 mL/kg), scaled to the body weight of each individual animal. Tumors were measured using callipers twice per week, and each animal was euthanized when its tumor reached the endpoint volume of 2000 mm3 or at the end of the study, whichever came first.

In one group of animals, 1 mg/kg ADCx19 was administered as a single dose on day 1 (qd×1).

In two other groups, the same dose of ADCx19 was administered as 3 fractionated doses i.e. 3 doses each of 0.33 mg/kg. In one group the doses were administered at 1 week intervals (qwk×3), in the second group the doses were administered at 4-day intervals (q4d×3).

It was observed that in both groups receiving the fractionated dose, tumour size grew steadily from ~day 20. In contrast, the group receiving the single dose on day 1 showed no significant tumour mass through to the end of the study (see FIG. 2).

NALM-6 Tumour Cell Inoculation Model

The human B-cell leukaemia NALM-6 was used as iv-xenotransplantation model. NALM-6 culture at passage 12 was used for tumor cell inoculation. Viability of inoculated cells was 90%.

Adult female NOG mice were 5-8 weeks of age and had a mean body weight of 17.2 g at the start of the experiment. After an acclimatization time of 7 days, 1×10^7 tumor cells from in vitro passage were iv inoculated into each female NOG mouse (day 0).

Treatment was started at day three after NALM-6 inoculation. Body weights were measured three times/week and all animals were checked daily for general health status.

Individual mice were sacrificed and autopsy was done, when hind leg paralysis occurred and/or body weight decreased ≥20%. The study was finished at day 90.

In one group of animals, 1 mg/kg ADCx19 was administered as a single dose on day 1 (qd×1).

In the other group, the same dose of ADCx19 was administered as 3 fractionated doses i.e. 3 doses each of 0.33 mg/kg, administered at 4-day intervals (q4d×3).

It was observed that in the group receiving the fractionated dose, mortality occurred in some individuals toward the end of the study. In contrast, the group receiving the single dose on day 1 showed no mortality through to the end of the study (see FIG. 3).

Example 5: Pharmokinetics of ADCx19 in ALL Patients

ADCx19 was administered to 19 patients with Relapsed or Refractory B-cell Lineage Acute Lymphoblastic Leukemias (B-ALL) comprising 3 dose cohorts (15, 30, and 60 µg/kg), using a 3-week treatment cycle with a single-dose administered on day 1.

Preliminary pharmacokinetic (PK) information from 7 patients (n=4 at 15 µg/kg; n=2 at 30 µg/kg; n=1 at 60 µg/kg) indicate inter-patient variability. For most patients, concentrations were near the lower limit of quantification and PK parameters could not be discerned. In those patients, rapid drug clearance was apparent in the early time course. In patients who exhibited a CR, a slower clearance compared to others was evident by Cycle 2.

The full clinical study protocol for the 3-week treatment cycle with a single-dose administered on day 1 is publically available at www.clinical trials.gov, having the ClinicalTrials.gov unique identifier: NCT02669264 (21 Feb. 2017 update).

Example 6: Synopsis of Fractionated Dosage Protocol

Indication

Patients with relapsed or refractory B-cell lineage acute lymphoblastic leukaemia (B-ALL) who have failed, or are intolerant to, any established therapy; or for whom no other treatment options are available.

Objectives
Primary Objectives:
Evaluate the safety and tolerability and determine the maximum tolerated dose (MTD) of ADCx19 in patients with relapsed or refractory B-ALL (Part 1).
Determine the recommended dose of ADCx19 for Part 2 (expansion).
Evaluate the safety and tolerability of ADCx19 in Part 2 (expansion) at the dose level recommended in Part 1.
Secondary Objectives:
The secondary objectives for Part 1 and Part 2 of the study are:
Evaluate the clinical activity of ADCx19, based on the patient's response to treatment (complete response [CR], CR with incomplete blood count recovery [CRi], partial response [PR], progressive disease [PD], no response [NR]) and determination of the overall response rate (ORR), duration of response (DOR), overall survival (OS), and progression-free survival (PFS).
Characterize the pharmacokinetic (PK) profile of ADCx19 (total antibody, drug-to-antibody ratio [DAR]≥0), PBD-conjugated antibody (DAR 1), and free warhead.
Evaluate anti-drug antibodies (ADAs) against ADCx19 in serum before, during, and after treatment with ADCx19.
Efficacy Assessment
Assessment of response to treatment with ADCx19 will be based on bone marrow samples (aspirate or biopsy, if aspirate unattainable). The activity of ADCx19 will be evaluated based on the Investigator's evaluation of the patient's response to ADCx19 as CR, CRi, PR, PD, or NR as defined herein.

PK Assessment
The PK profile of ADCx19 (total antibody; DAR 0), PBD-conjugated antibody (DAR 1), and free warhead will be assessed centrally in Cycles 1 and 2. The PK profile will include determination of standard PK parameters (e.g., maximum concentration [Cmax], time to Cmax [Tmax]). The following PD and other exploratory assessments will be performed at various time points in the study:
Flow cytometric assessment of CD19 and other CD marker expression in mononuclear cells (MNCs) isolated from bone marrow aspirate and whole blood (WB), tested retrospectively by a central laboratory in samples obtained before treatment with ADCx19.
Level of ADAs against ADCx19 in serum before, during, and after treatment with ADCx19.
Analysis of peripheral WBC populations and CD marker panel expression (e.g., CD19, CD20, CD21, CD22) before, during, and after treatment with ADCx19 (Cycles 1 and 2) by flow cytometry in WB.
Serum concentrations of ADCx19 and free warhead, QTc interval.
Measurement of MRD by flow cytometry in bone marrow.

Safety Assessment
Safety will be assessed based on AEs, serious AEs (SAEs), treatment discontinuations due to AEs, DLTs (as defined herein) measurements of cytokines in serum, periodic 12-lead electrocardiogram (ECG) recordings, physical examinations, vital signs measurements, ECOG performance status, and haematology, biochemistry, coagulation panel, pregnancy testing (for women of child-bearing potential) and urinalysis test results. Adverse events will be graded according to CTCAE Version 4.0 (v4.03, published Jun. 14, 2010; NIH Publication No. 09-5410).

Product Dosage and Mode of Administration
ADCx19 is a sterile formulation containing PBD-conjugated humanized monoclonal IgG1 antibody (DAR 1), humanized monoclonal IgG1 antibody (DAR=0), and SG3249. It is provided pre-formulated in 10 mL single-use, glass vials containing approximately 16 mg ADCx19 per vial (deliverable volume 3.2 mL, with an additional 0.3 mL overfill at 5 mg/mL). Patients will receive a 1-hour intravenous (IV) infusion of ADCx19 on Day 1 of Cycle 1. If ADCx19 is well tolerated after the first infusion, the infusion duration may be shortened to 30 minutes for subsequent cycles for that patient, at the Investigator's discretion.

The investigational product administration schedule is as follows:
Patients will be given ADCx19 (weekly [QW]) on Days 1, 8, and 15 of each 3-week (21-day) treatment cycle.
A patient will maintain the same treatment schedule throughout the duration of the trial.
Once a patient achieves CR/CRi, frequency or dose may be adjusted by the DESC based on emerging safety, efficacy, and PK profile.
The trial will be continuously monitored for emerging safety, efficacy and/or PK profile, and the DESC will determine if it is appropriate to maintain a QW schedule, revert to an every 3-week (Q3W) schedule, or test other dosing regimens.

Dose Escalation Design
Dose-escalation (Part 1) will be conducted according to a 3+3 design. The initial dose of ADCx19 will be 15 µg/kg (Dose Level 1), and the highest allowed dose will be 600 µg/kg.

The DLT observation period for dose-escalation will be 1 cycle. Patients will be entered sequentially to each dose level.

For each dose level, if none of the first 3 patients at that level experiences a DLT, new patients may be entered at the next higher dose level. If 1 of 3 patients experiences a DLT, up to 3 more patients are to be treated at that same dose level. If none of the additional 3 patients at that dose level experiences a DLT, new patients may then be entered at the next higher dose level. However, if 1 or more of the additional 3 patients experiences a DLT, then no further patients are to be started at that dose level and the preceding dose is identified as the MTD. The MTD; therefore, is defined as the highest dose level at which none of the first 3 treated patients, or no more than 1 of the first 6 treated patients, experiences a DLT.

During Part 1, the dose escalation steering committee (DESC) may expand enrolment at doses below the current dose level as part of the dose-escalation process. Additional patients may only be added at a lower dose level provided there is at least one patient who has achieved a PR (or better). No more than 10 patients in total can be treated at any dose level unless ≥3 of the 10 patients have achieved a PR or better.

During dose expansion, patients will be monitored for safety using the same DLT criteria employed during dose-escalation. If during the treatment period, >30% of patients experience safety events that would meet the criteria that define a DLT in the dose-escalation phase of the study, enrolment in the expansion cohort(s) may be paused and the study data reviewed to determine whether additional monitoring or other action (such as alternate dose levels) should be evaluated prior to further enrolment.

Example 7: Summary of ADCx19 Treatment Safety and Efficacy Studies

Study Design

A Phase 1, open-label, dose-escalation (part 1) and dose-expansion (part 2), multicenter, US study is enrolling patients with R/R B-ALL.

In part 1, patients are assigned to treatment according to a 3+3 dose-escalation design to determine the maximum tolerated dose (MTD). The initial dose of ADCx19 was 15 µg/kg (dose level 1). ADCx19 is given intravenously on Day 1 of each 21-day cycle for patients treated every 3 weeks, and on Days 1, 8, and 15 for patients assigned to a weekly dosing regimen.

Part 2 will further evaluate the safety, tolerability, PK, and clinical activity of ADCx19 at the dose recommended from part 1. Complete response is defined as achieving each of the following:

Bone marrow differential showing ≤5% blast cells
Absolute neutrophil count ≥1.0×109/L and platelet count ≥100×109/L
Absence of extramedullary disease
Patient is independent of red blood cell transfusions.

| Key patient inclusion criteria | Key patient exclusion criteria |
| --- | --- |
| Patients aged 12 years and older with R/R B-ALL who have failed, or are intolerant to, any established therapy; or for whom no other treatment options are available | Known active central nervous system leukaemia or Burkitt's leukaemia/lymphoma |
| Eastern Cooperative Oncology Group performance status 0-2 | Autologous or allogenic transplant within 60 days prior to screening or active graft-versus-host disease |
| White blood cell count <15,000 cells/µL prior to Day 1 | Major surgery, chemotherapy, systemic therapy, or radiotherapy within 14 days prior to Day 1 treatment Active autoimmune disease |

Results

Patient Characteristics

As of Oct. 30, 2017, 29 patients (18 male, 11 female) with B-ALL have been treated with ADCx19.

Patients had received a median (min, max) of 2 (1, 12) previous chemotherapies. Eleven (37.9%) patients had received prior allogeneic stem cell transplantation. No dose-limiting toxicities (DLTs) have been observed up to the highest evaluated dose of 150 µg/kg once every 3 weeks (q3w). The most recently treated cohort received ADCx19 at a dose of 50 µg/kg once weekly.

PK Data

Figure 4:
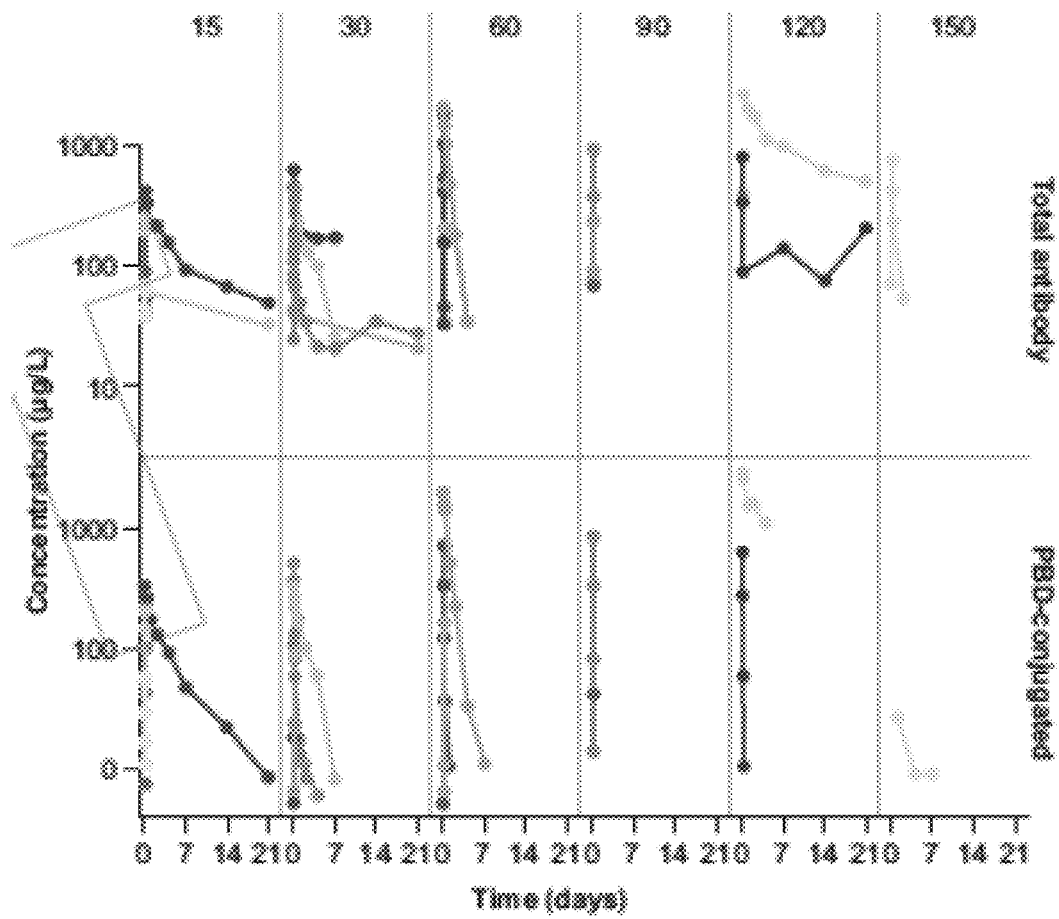
FIG. 4 is a graph showing total antibody and ADCx19 concentrations versus time by patient and dose (Cycle 1).

PK data show PBD-conjugated antibody and total antibody concentrations below quantifiable levels of 5.0 and 20 ng/L, respectively, well before end of the 21-day treatment cycle (see FIG. 4). PBD dimer concentrations were largely below measurable levels throughout the time course, justifying a change to weekly dosing.

Safety Data

No DLTs were observed Treatment-emergent adverse events (TEAEs) were reported by 28/29 (96.6%) patients with 265 TEAEs reported in total. Twelve (41.4%) patients reported adverse events deemed to be possibly or probably related to ADCx19. The most common TEAEs were:

Nausea (n=9)

Fatigue (n=7)

Febrile neutropenia (n=7)

Headache (n=7).

Grade ≥3 TEAEs were reported in 24/29 (82.8%) patients, of which febrile neutropenia (n=7) and neutrophil count decrease (n=4) were the most common (see table below).

Two patients experienced TEAEs with fatal outcomes (lung infection and sepsis), both from the 120 µg/kg q3w dosing group. Four patients experienced TEAEs leading to a dose delay or reduction, but no TEAEs led to treatment withdrawal. Liver toxicity events were recorded in 7 patients, leading to dose delay in 1 patient (owing to hyperbilirubinemia) Four patients experienced Grade 3 liver toxicity events, including during Cycle 1; all were reversible (median [range] duration: 11.5 [5-36] days) and not related to veno-occlusive disease. There were 3 infusion-related reactions, including 1 case each of Grade 2 infusion-related reaction and cytokine release syndrome, and 1 case of Grade 1 tachycardia.

The MTD has not yet been reached.

Grade ≥3 TEAEs by preferred term (safety analysis set; dose in ug/kg) are shown below in Table 6.

TABLE 6

|  | q3w | | | | | | qw | |
| --- | --- | --- | --- | --- | --- | --- | --- | --- |
| TEAEs (Grade ≥3) | 15 (n = 5) | 30 (n = 7) | 60 (n = 3) | 90 (n = 4) | 120 (n = 5) | 150 (n = 4) | 50 (n = 1) | Total (N = 29) |
| Grade ≥3 TEAE reported by ≥10% of patients, n (%) | 5 (100) | 4 (57.1) | 3 (100) | 3 (75.0) | 5 (100) | 4 (100) | 0 | 24 (82.8) |
| Febrile neutropenia | 0 | 1 (14.3) | 1 (33.3) | 2 (50.0) | 1 (20.0) | 2 (50.0) | 0 | 7 (24.1) |
| Neutrophil count decreased | 1 (20.0) | 2 (28.6) | 0 | 0 | 1 (20.0) | 0 | 0 | 4 (13.8) |
| Abdominal pain | 0 | 1 (14.3) | 0 | 1 (25.0) | 0 | 1 (25.0) | 0 | 3 (10.3) |
| Bacteremia | 0 | 0 | 0 | 2 (50.0) | 1 (20.0) | 0 | 0 | 3 (10.3) |
| Lung infection | 0 | 1 (14.3) | 1 (33.3) | 0 | 1 (20.0) | 0 | 0 | 3 (10.3) |
| Sepsis | 0 | 2 (28.6) | 0 | 0 | 1 (20.0) | 0 | 0 | 3 (10.3) |

Efficacy Data

Two patients achieved a complete response with no minimal residual disease (MRD), at a dose of 30 µg/kg and 120 µg/kg q3w after 5 and 2 treatment cycles, respectively.

Both responders had previously received blinatumomab.

A third patient achieved a complete response with positive MRD at a dose of 150 µg/kg q3w.

A fourth patient achieved a complete marrow response with an incomplete blood count response and progression of extramedullary disease at a dose of 150 µg/kg q3w.

Conclusions

In this Phase 1 study in patients with R/R B-ALL, single-agent ADCx19 was well tolerated with no DLTs and showed 2 MRD-negative complete remissions in a heavily pretreated population.

Dose escalation will continue to find the MTD for a weekly regimen.

A dose-expansion phase in part 2 of the study is planned to further evaluate the tolerability, safety, PK, and activity of ADCx19.

The invention claimed is:

1. A method of treating a subject suffering from a proliferative disease, said method comprising:
   administering to a subject suffering from a proliferative disease an effective amount of a CD19-antibody drug conjugate (ADC),
   wherein (i) the CD19-ADC comprises as the a pyrrolobenzodiazepine (PBD) dimer, linked to an antibody that binds to CD19; and (ii) the CD19-ADC has a drug to antibody ratio (DAR) of between 1 and 8,
   wherein (i) the CD19-ADC is administered to the subject in a dosage regime comprising at least two treatment cycles; and (ii) the dose of CD19-ADC is reduced following the second treatment cycle; and
   wherein (i) the proliferative disease is a CD19$^+$ cancer or a CD19$^+$ autoimmune disease; and (ii) the PBD dimer is of formula I:

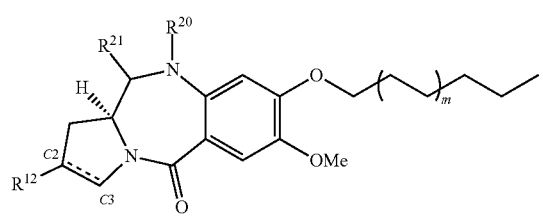

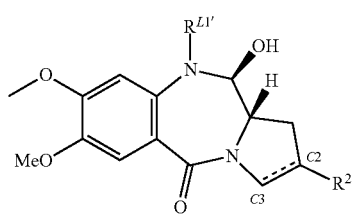

(I)

wherein
(a) $R^{L1'}$ is a linker for connection to Ab, wherein $R^{L1'}$ is

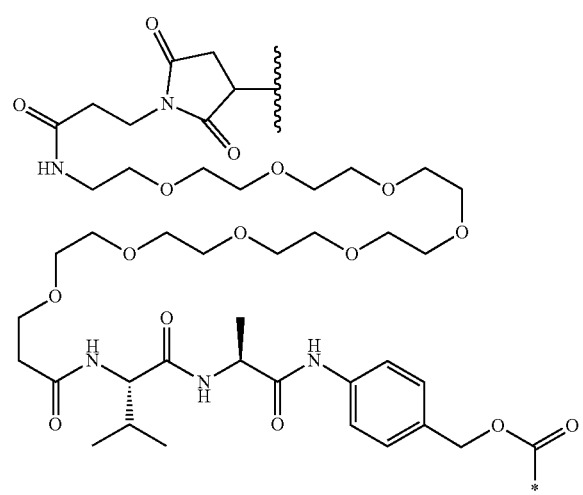 [SMILES: *C(=O)OCc1ccc(NC(=O)[C@H](C)NC(=O)[C@@H](NC(=O)CCOCCOCCOCCOCCOCCOCCOCCOCCNC(=O)CCN2C(=O)CC(*)C2=O)C(C)C)cc1]

wherein the wavy line indicates the point of attachment to the Ab and the asterisk indicates the point of attachment to the nitrogen in Formula (I);
(b) (i) $R^{20}$ and $R^{21}$ either together form a double bond between the nitrogen and carbon atoms to which they are bound; or (ii) $R^{20}$ is a capping group $R^C$, and $R^{21}$ is OH;
(c) m is 0 or 1; and
(d) when there is a double bond between C2 and C3, $R^2$ is methyl;

when there is a single bond between C2 and C3, $R^2$ is either H or
when there is a double bond between C2' and C3', $R^{12}$ is methyl;
when there is a single bond between C2' and C3', $R^{12}$ is H or

2. The method of claim 1, wherein the antibody comprises a VH domain having the amino acid sequence of SEQ ID NO.2 and a VL domain having the amino acid sequence of SEQ ID NO. 8.

3. The method of claim 1, wherein the PBD is:

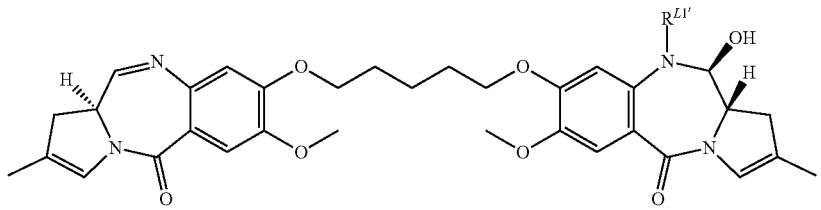

wherein $R^{L1'}$ is a linker for connection to Ab.

4. The method of claim 1, wherein the CD19-ADC has the following structure:

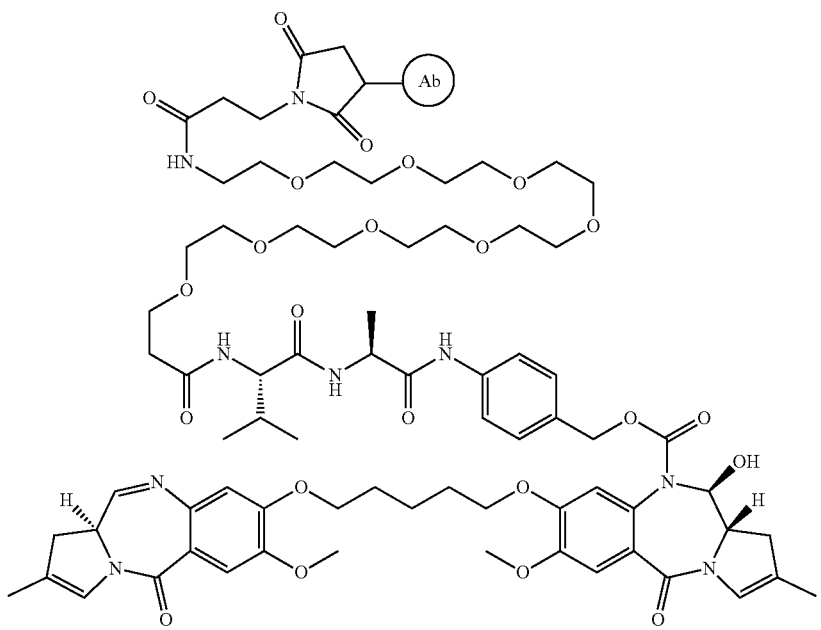

wherein Ab comprises a VH domain having the amino acid sequence of SEQ ID NO.2 and a VL domain having the amino acid sequence of SEQ ID NO. 8.

5. The method according to claim 1, wherein each treatment cycle is about 3 weeks or about 6 weeks.

6. The method according to claim 1, wherein the dose of CD19-ADC is reduced following the second treatment cycle by at least 50%, at least 55%, at least 60% at least 65%, at least 70%, at least 75%, at least 80%, at least 90%, or at least 95%.

7. The method according to claim 1, wherein the starting dose of CD19-ADC is from about 121 µg/kg to about 180 µg/kg.

8. The method according to claim 7, wherein the starting dose of CD19-ADC is from about 140 µg/kg to about 160 µg/kg.

9. The method according to claim 1, wherein the CD19-ADC is administered in combination with a steroid.

10. The method according to claim 1, wherein the CD19$^+$ cancer is a leukemia or a lymphoma.

11. A method of treating a subject suffering from a proliferative disease, said method comprising:
administering to a subject suffering from a proliferative disease an effective amount of a CD19-antibody drug conjugate (ADC), wherein the CD19-ADC has the chemical structure:

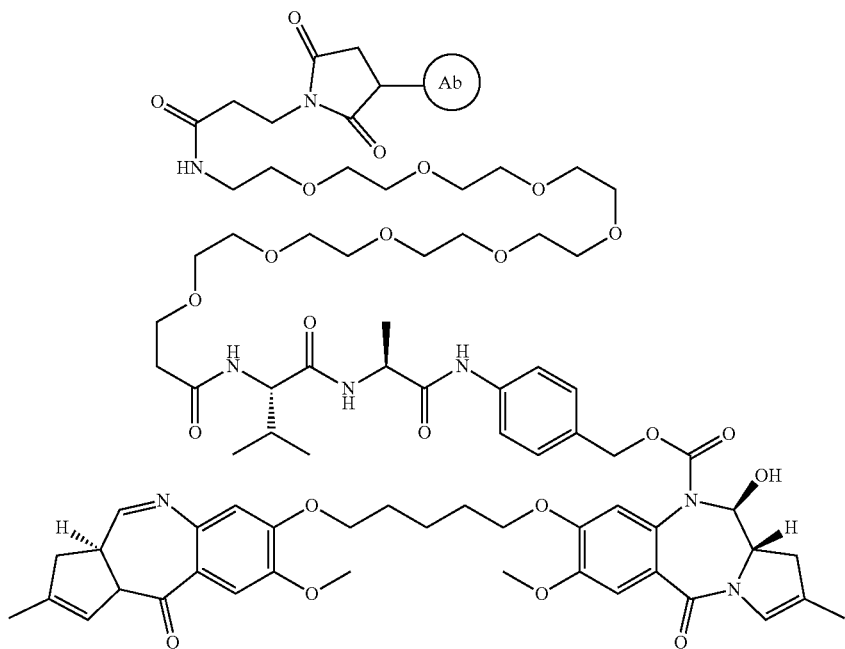

and the Ab is a CD19 antibody comprising a VH domain having the amino acid sequence of SEQ ID NO.2 and a VL domain having the amino acid sequence of SEQ ID NO. 8, and the drug to antibody ratio (DAR) is between 1 and 8;
wherein (i) the CD19-ADC is administered to the subject in a dosage regime comprising at least two treatment cycles; and (ii) the dose of CD19-ADC is reduced following the second treatment cycle; and
wherein the proliferative disease is CD19+.

12. The method according to claim 11, wherein each treatment cycle is about 3 weeks or about 6 weeks.

13. The method according to claim 11, wherein the dose of CD19-ADC is reduced following the second treatment cycle by at least 50%, at least 55%, at least 60% at least 65%, at least 70%, at least 75%, at least 80%, at least 90%, or at least 95%.

14. The method according to claim 11, wherein the starting dose of CD19-ADC is from about 121 µg/kg to about 180 µg/kg.

15. The method according to claim 11, wherein the starting dose of CD19-ADC is from about 140 µg/kg to about 160 µg/kg.

16. The method according to claim 11, wherein the CD19-ADC is administered in combination with a steroid.

17. The method according to claim 11, wherein the CD19+ proliferative disease is a leukemia or a lymphoma.

18. The method according to claim 11, wherein the CD19+ proliferative disease is a CD19+ overexpressing cancer.

19. The method according to claim 13, wherein the CD19-ADC is administered at about 150 µg/kg for two 3-week treatment cycles followed by about 75 µg/kg for every subsequent 3-week treatment cycle.

* * * * *

UNITED STATES PATENT AND TRADEMARK OFFICE
CERTIFICATE OF CORRECTION

| | | |
|---|---|---|
| PATENT NO. | : 11,938,192 B2 | |
| APPLICATION NO. | : 17/699065 | |
| DATED | : March 26, 2024 | |
| INVENTOR(S) | : Jay Marshall Feingold and David Rodney Ungar | |

It is certified that error appears in the above-identified patent and that said Letters Patent is hereby corrected as shown below:

In the Claims

Claim 1, Column 107, Line 24 reads:
"wherein (i) the CD19-ADC comprises as the a pyr-"
Whereas it should read:
-- wherein (i) the CD19-ADC comprises as a drug, a pyr- --;

Claim 1, Column 108, Line 17 reads:
"(a) $R^{L1'}$ is a linker for connection to Ab, wherein $R^{L1'}$ is"
Whereas it should read:
-- (a) $R^{L1'}$ is a linker for connection to the antibody, wherein $R^{L1'}$ is --.

Signed and Sealed this
Fourth Day of June, 2024

Katherine Kelly Vidal
*Director of the United States Patent and Trademark Office*